United States Patent
Dye et al.

(10) Patent No.: US 10,357,592 B2
(45) Date of Patent: Jul. 23, 2019

(54) EXTRACELLULAR MATRIX—SYNTHETIC SKIN SCAFFOLD

(71) Applicant: SMART MATRIX INTELLECTUAL PROPERTY LIMITED, Northwood, Middlesex (GB)

(72) Inventors: Julian F. Dye, Middlesex (GB); Vaibhav Sharma, Northwood (GB); Elena Garcia-Gareta, London (GB); Keith Alan Blackwood, Channel Islands (GB)

(73) Assignee: SMART MATRIX INTELLECTUAL PROPERTY LIMITED, Northwood, Middlesex (GB)

( * ) Notice: Subject to any disclaimer, the term of this patent is extended or adjusted under 35 U.S.C. 154(b) by 56 days.

(21) Appl. No.: 14/398,630

(22) PCT Filed: May 3, 2013

(86) PCT No.: PCT/GB2013/051158
§ 371 (c)(1),
(2) Date: Nov. 3, 2014

(87) PCT Pub. No.: WO2013/164635
PCT Pub. Date: Nov. 7, 2013

(65) Prior Publication Data
US 2015/0118308 A1    Apr. 30, 2015

(30) Foreign Application Priority Data

May 3, 2012 (GB) .................................. 1207781.4

(51) Int. Cl.
| | |
|---|---|
| *A61L 27/22* | (2006.01) |
| *A61L 27/56* | (2006.01) |
| *A61L 27/60* | (2006.01) |
| *C12N 5/00* | (2006.01) |
| *C12N 5/071* | (2010.01) |
| *C12N 5/077* | (2010.01) |

(52) U.S. Cl.
CPC ............. *A61L 27/225* (2013.01); *A61L 27/56* (2013.01); *A61L 27/60* (2013.01); *C12N 5/0068* (2013.01); *C12N 5/069* (2013.01); *C12N 5/0656* (2013.01); *A61L 2300/412* (2013.01); *C12N 2533/56* (2013.01); *C12N 2537/10* (2013.01)

(58) Field of Classification Search
None
See application file for complete search history.

(56) References Cited

U.S. PATENT DOCUMENTS

| | | | | |
|---|---|---|---|---|
| 8,697,118 B2* | 4/2014 | Olson | ..................... | A61L 15/44 424/443 |
| 2009/0028949 A1 | 1/2009 | Leonard et al. | | |

FOREIGN PATENT DOCUMENTS

| | | |
|---|---|---|
| JP | 9506612 A | 6/1997 |
| JP | 2006-206610 A | 8/2006 |
| JP | 2007-526298 A | 9/2007 |
| JP | 2010-537977 A | 12/2010 |
| JP | 2012-503524 A | 2/2012 |
| WO | 2007/144644 A2 | 12/2007 |

OTHER PUBLICATIONS

Balzar, D. 1997 Specialist Surfactants, Alkyl polyglucosides: 169-207.*
Jain, N.K. 2010 Current Protocols in Protein Science: 4.9.1-4.9.12.*
PanReac Appli Chem Detergents reference sheets 2010: 7 pages total. (retrieved from the internet Aug. 4, 2016).*
Blackwood, K.A. et al., "Optimising the production criteria of 'smart matrix' fibrin based scaffold" European Cells and Materials (Jan. 2011) pp. 35, vol. 22, No. Suppl. 2.
International Search Report dated Jul. 30, 2013 issued in International Application No. PCT/GB2013/051158.
Japanese Office Action dated Jan. 31, 2017 issued in Japanese Patent Application No. 2015-509501.

* cited by examiner

*Primary Examiner* — Marsha Tsay
(74) *Attorney, Agent, or Firm* — Scully Scott Murphy & Presser

(57) ABSTRACT

The present invention provides a process or preparing an extracellular matrix composition which comprises: (a) mixing an aqueous solution of fibrinogen with a coagulating agent and a bulking agent and a foaming agent; (b) causing the mixture to foam and coagulate; (c) incubating the mixture obtained in step (b) with a cross-linking agent; and (d) washing the cross-linked composition obtained in step (c) to remove the cross-linking agent. Wherein the foaming agent consists of or comprises one or more surfactant agent(s) from the class of sugar-surfactants. The invention also relates to the formulation mixture as such, and to the products of the process.

38 Claims, 28 Drawing Sheets

SMOF2 scaffolds

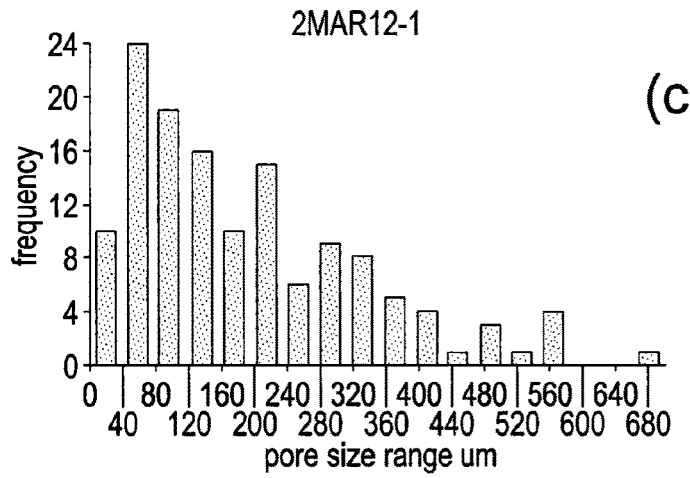
Fig. 21 (continued)
DdSuc scaffolds
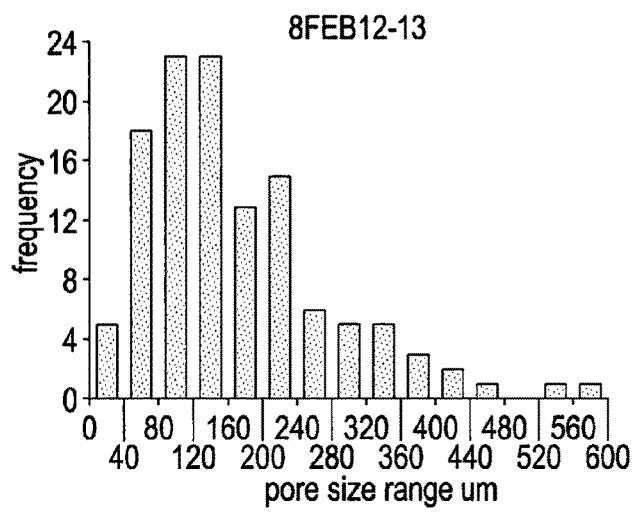
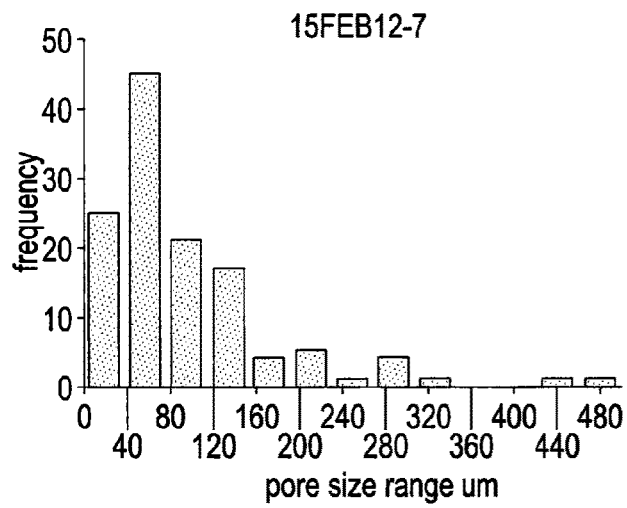

EXTRACELLULAR MATRIX—SYNTHETIC SKIN SCAFFOLD

INTRODUCTION

Smart Matrix™ (synthetic skin scaffold; synthetic dermal replacement (SDR)) is an intrinsically pro-angiogenic biomaterial synthetic dermal replacement scaffold, designed to overcome the problem of delayed or compromised integration into a wound site. It is an Extracellular Matrix (ECM) in the form of a composite of fibrin with alginate (or other suitable bulking agent), stabilised by glutaraldehyde cross linking, resulting in a porous resorbable and biocompatible cytoadhesive material that facilitates rapid cellular infiltration. The basic formulation to make the Smart Matrix™ involves an enzymatic reaction with fibrinogen protein and clotting agent (Thrombin). In order to provide bulking and support to the scaffold a bulking agent (Alginate) is used (Dye, WO2007/144644-A, 2007). Initially, it had been anticipated that the use of calcium ions in the manufacture formulation would function to support the alginate bulking effect through gellation, in addition to a colligative interaction with fibrin. However, although a stable and functional scaffold could be formed in vitro which supported rapid cellular ingress this formulation was observed to generate an unacceptable inflammatory response in a full thickness wound bed in vivo (porcine model), which increased between day 7 and day 14. It was found that this response was attenuated by decreasing the calcium concentration used in the manufacture formulation (Edwards et al, 2011).

However, limiting the calcium ion concentration to 2 mM in the manufacture step is insufficient to cause the gellation of alginate, which is unable to holding a foam structure for long enough for fibrinogen coagulation to occur and bind the whole mixture. This presented a manufacture problem which was tackled through the use of surfactants and stabilising agents.

Surfactants are compounds that reduce surface tension between liquids, acting as detergents, emulsifiers or foaming agents.

"Span" are also known as Sorbitan esters and are a family of lipophilic non ionic sugar-acyl surfactants used as emulsifying agents in the preparation of emulsions, creams and ointments.

OGP is in another family of sugar-acyl surfactants. OGP is already known in the art as a detergent used to dissolve integral membrane proteins. It is widely used with proteins because it can readily be removed from final protein extract. Other members of the class of sugar-acyl surfactants are, Hexyl β-D-glucopyranoside (HGP), Octyl β-D-1-thioglucopyranoside (TGP), Decyl-β-D-glucopyranoside (DGP), Dodecyl-β-D-glucopyranoside (DdGP)N-Octyl β-D-Maltoside (ODM) and Decyl β-D-maltopyranoside (DMP). Further members include cyclohexyl-ethanoyl-maltoside, n-decyl- and n-dodecyl-sucrose.

The Pluronic family of surfactants, including F127, F-68, L101 are non-ionic block co-polymers of ethylene and propylene oxide, well known for their surfactant properties.

The initial surfactant investigated was Pluronic F127, a block copolymer with high biocompatibility and medical use, and the property in high concentration of spontaneously gelling at around 37° C. This yielded a porous scaffold which was found to integrate well. By contrast, scaffold made with Pluronic L101 (antifoam) yielded a homogenously dense scaffold. There was a marked difference on integration rates, with the porous scaffold integrating rapidly and vascularising over 1 week, with blood flow being detected at day 3, and visible peach-pink colouration indicative of 'take'. The Pluronic F127 result was repeated with Pluronic F68, which has slightly greater foaming property than F127. However, increasing porosity with these surfactants resulted in a surprising degree of inflammation increasing to day 14, despite low calcium levels in the formulation mixture. This was associated with relatively large (in the approximate range of 20-100 μm in length) dense plates of scaffold within the scaffold structure, which appeared to be eliciting a foreign body response.

PRIOR ART

The basic formulation to make the Smart Matrix™ is described in WO2007/144644-A, 2007. Where legally permissible, the content of this document is incorporated herein by reference.

US 2002/0131933-A describes a biopolymer membrane and methods for its preparation. The membrane is intended to be dried and compressed. In its dry form it has a thickness less than about 75 microns, a solvent content less than about 5% by weight of the membrane, a density greater than about 1 g/cm$^3$ and a maximum pore size of about 20 microns.

WO20041067704-A describes freeze-dried fibrin matrices ("sponges") and methods for preparation thereof. Glycosamino-glycans and bioactive agents are incorporated in the matrix during the formation of the sponge.

U.S. Pat. No. 4,442,655 describes Fibrinogen-containing dry preparations and the manufacture and use thereof. The products have a foam-like/fleece-like structure obtained by freeze-drying. The dry preparations are provided for use as a wound toilet material, as a filling material for bone cavities and/or as a supporting material for further active substances.

The Table below compares and contrasts the prior art disclosures:

Points of difference between the ECM Composition of WO2007/144644 Dye and the disclosures of US2002-0131933 Delmotte D1, WO2004/067704 Yayon D2 & U.S. Pat. No. 4,442,655 Stroetmann D3

| D1 Features | ECM |
|---|---|
| pore size >20 um | porosity <20 um-up to 250 um (FIG. 29) |
| dense aggregated microscale structure | interconnected fibrous microstructure (FIG. 29) |
| anti-adhesive function | density approx 10 ug/cm3 - no data given |
| no pore interconnectivity/cell conductivity | pro-adhesive function (FIG. 2-5) |
| no surfactant use | cell conductivity (FIG. 4, 42) |
| no reductant or detoxification use | surfactant use |
| no biocompatibility data | reductant or detoxification use |
| no vascularisation data | in vivo cellular integration/vascularisation (FIG. 42) |

-continued

Points of difference between the ECM Composition of WO2007/144644
Dye and the disclosures of US2002-0131933 Delmotte D1, WO2004/067704
Yayon D2 & U.S. Pat. No. 4,442,655 Stroetmann D3

| | ECM |
|---|---|
| Advantages | |
| | ECM functionality |
| | pro-adhesive function |
| | low density foam formation |
| | coagulation to create porous material |
| | cross-linking to stabilise structure |
| | cross linking to improve adhesive function |
| | biocompatibility improved with reduction step |
| | surfactant compatible with fibrinogen coagulation |
| | use of material as an ECM/scaffold |
| | in vivo cellular integration |
| D2 Features | |
| low stability in proteolytic solution | fibrous microstructure (FIG. 29) |
| no cross-linking of fibrin | long-term stability in proteolytic solution |
| no foaming step to increase porosity | pro-adhesive function (Fig |
| no surfactant or foaming agent | cell conductivity (Fig |
| no cell-adhesion data | surfactant use |
| | reductant or detoxification use |
| Advantages | |
| | ECM functionality |
| | pro-adhesive function |
| | low density foam formation |
| | coagulation to create porous material |
| | cross-linking to stabilise structure |
| | cross linking to improve adhesive function |
| | biocompatibility improved with reduction step |
| | surfactant compatible with fibrinogen coagulation |
| | cell use of material as an ECM/scaffold |
| | in vivo cellular integration |
| D3 Features | |
| mixed fibrinogen/fibrin product | pro-adhesive function (FIG. 2-5) |
| occlusive material due to free fibrinogen | cell conductive function (FIG. 4, 42) |
| no biocompatibility | surfactant use |
| no cell adhesion | reductant or detoxification use |
| no cell conductivity | |
| Advantages | |
| wound toilet material | ECM functionality |
| anti-coagulant/occlusive dressing | pro-adhesive function |
| depot material | cross linking to improve adhesive function |
| no evidence supportive of ECM scaffold functionality | biocompatibility improved with reduction step |
| | surfactant compatible with fibrinogen coagulation |
| | cell use of material as an ECM/scaffold |
| | in vivo cellular integration |

BRIEF DESCRIPTION OF THE PRESENT INVENTION

The original formulation provided an ECM, but there remained the problem that, in use, there was a tendency for there to be a degree of inflammation. Inflammation can be caused by a number of factors which constitute, separately or in combination, a "foreign body response".

In the context of the ECMs evaluated, potential inflammatory factors include endotoxin alginate; cytotoxic cross-link adducts; phagocytic particles (such as calcium phosphate particles).

In seeking to provide the present invention, a formulation was used in which a surfactant is used to control porosity of the matrix product. However, a major problem with this approach is the formation of dense micro-aggregates or plates within the scaffold structure, which appeared to elicit a foreign body response.

We have investigated the effect that altering the surfactant composition has upon the structure of the formed Smart Matrix scaffold. Specifically, coagulation studies, which measure the onset and rate of coagulation and also the resultant gel quality, define the biochemical compatibility of the surfactant mix. Standard foam stability tests, which measure duration and porosity, establish a criterion for effectiveness of the surfactant. Visual descriptions of the foaming effect will establish the degrees of foam stability during and at the end of the manufacture process, and histological analysis is used to measure the micro-porosity, pore size and homogeneity of the scaffolds.

The present invention provides a formulation, and the process for producing an ECM of fibrin combined with a colligative bulking agent such as alginate from this formulation, which will avoid the formation of the dense aggregates and provide an homogenous porous structure resulting in a pro-angiogenic scaffold which integrates without excessive inflammation.

It was speculated that aggregates may arise from protein precipitation, distinct from coagulation, formed during the manufacture step as a consequence of adding surfactant. We identified evidence of protein precipitation in the reaction mixture not associated with enzymatic activity, but due to the combination of other reagents.

The invention now provides a formulation, and its use, to minimise precipitation and maximise coagulation.

In a first aspect, the invention provides Smart Matrix™ Optimised Formulation #1 or SMOF #1 referred to herein, and variants thereof, and its use to produce an ECM. This includes the introduction of the "sugar surfactant" component Octyl β-D-glucopyranoside (OGP) with a Pluronic such as F68 "poloxamer" foaming type surfactant, to form and stabilise a foam structure to determine the ultimate structure of the coagulated fibrin scaffold.

This invention also includes a protein stabilising agent, such as trehalose (D-trehalose).

The SMOF #1 scaffolds demonstrated a close-to-ideal pore structure and porosity as assessed by cellularisation of prototypes engrafted onto full thickness wounds. This formula has been shown to be efficient in in vitro models and in vivo (porcine full thickness wound healing). There was a marked reduction in occurrence of dense plates in the scaffold compared to scaffolds in which porosity was controlled by simple addition of a surfactant (such as a foam-forming Pluronic, Triton X100 or Tween 20). Compared to Pluronic scaffolds, reduction in the inflammatory response was observed in vivo at day 14.

Despite an improvement in reducing the inflammatory response, the result was higher than ideal. Light microscopic analysis of the structures show non-homogenous microstructure with dense micro aggregates and pore size over the depth of the scaffold. Additionally, the resultant pore structure of the scaffold is on the larger side of the range which has been observed to result in organised tissue ingrowth. Extraneous factors appeared to result in the formation of dense aggregates of scaffold material in vivo although before application an open pore structure was apparent. It seems reasonable to conclude that wherever dense aggregated scaffold material is present in vivo, it will elicit an inflammatory response, which is undesired, concomitant with new tissue ingrowth.

The initial results according to the first aspect of the invention did appear to be still sub-optimal.

In a second aspect, the invention provides further improved formulations, and their use to produce ECMs. This aspect further optimises the pore structure and homogeneity of Smart Matrix™ Optimised Formulation #1 (SMOF-1). To achieve this, the invention provides for the use of at least two different sugar surfactants in the formulation.

These formulations also include a protein stabilising agent, such as trehalose. We have also investigated protein stabilising agents, which can stabilise the fibrinogen prior to coagulation. Small carbohydrates, poly-ols, such as glycerol, sorbitol, glucose and sucrose trehalose and raffinose have been tested. From this work, the preferred sugar stabiliser is trehalose.

Trehalose—Concentration Range for Use as a Protein Stabilising Agent:

A useful concentration range of trehalose as a stabilising agent is broadly between 2.5-20%. More specifically the range 5-11% (before and after alginate and surfactant addition) has been established as effective in scaffold manufacture, as explained below. This can be achieved by using a saturated stock solution.

The stock trehalose solution is a saturated solution at about 60-66% at 30-37° C. There is a temperature effect on the saturation, leading to different values at different temperatures. There is supersaturation phenomenon which introduces variation around what is saturated at around 37° C. The range between 60 & 66% mass:vol does cover this. 66% can be achieved by supersaturation at elevated temperature (e.g. using a microwave to heat the solution during preparation) but slow crystallisation occurs on cooling. Using a slower dissolution at 37° C. leads to an equilibrium value of about 61%.

Solutions of fibrinogen, trehalose, and alginate are preferably warmed in a waterbath at 37° C., but the mixing is performed in ambient conditions (20° C. air) so the actual temperature at time of mixing is about 25-30° C.

After casting, the foamed mixture is placed in a humidified 37° C. incubator, so the temperature will approach 37° C. after about 10 minutes. Maintaining the solutions at ambient temp (20° C.) will still work, but with less foam, and coagulation will also still occur at room temperature, but some collapse of foam is anticipated during the longer time required for coagulation.

The initial dilution of trehalose with the fibrinogen component gives approx ×5 dilution. For example the initial trehalose concentration of stock solution is subsequently about 11% in the Fibrinogen solution by ×5 dilution of 0.6 ml stock into 3 ml Fbg. There is then a further ×2 dilution using 3 ml Alginic Acid to give around 5.5%. [See table entitled Table of concentrations of key components of Smart Matrix optimised formulae]

Alternatively, trehalose could be added into the mixture by dissolving it in the prepared fibrinogen solution, or with the alginate or other bulking agent. Particularly if a higher concentrations of trehalose were desired this could also be achieved by varying the starting concentrations of stock reagent solutions. For example, alginate at 4% or 5% would achieve a useful volume range to add a greater volume of trehalose.

The variation of the stock trehalose solution concentration in the range 60-66% results in the initial dilution giving a range of approximately 10-11% after mixing with Fibrinogen, and a concentration in the range approximately 5-5.5% after alginate addition. The potential concentration range in the mixture broadens after alginate addition (e.g. 4.9-6.8% for 1.5 or 3 ml equivalents), and after surfactant addition (e.g. 4.7-6.3% for the same 1.5 or 3 ml equivalents).

Consequently, the trehalose content should be in the range 10-11% before thrombin addition; then after thrombin/alginate/surfactant addition the trehalose content should be in the range 4-7.5%.

We have shown that trehalose addition to a standard fibrinogen coagulation assay caused an increased lag time before onset of coagulation. However, over the trehalose concentration range 3-13% in the manufacture mixture, the profile of coagulation and the maximum rate of coagulation were little affected.

Importantly, above a trehalose concentration of 13% (i.e. at 19%) coagulation is very substantially inhibited. This demonstrates that there is an upper limit of trehalose concentration when trehalose is to be used as a protein stabilising agent.

Fibrinogen, a surfactant, a stabilising agent and a bulking agent could be combined as dry powders, powders a pre-lyophilised mixture or a pre-prepared solution of these in a suitable buffer such as MES/NaCl. Alginate might be less suitable as a bulking agent (because it is fairly slow to dissolve), and could be replaced by a methyl cellulose or hydroxy-ethyl starch. This, reconstituted, would just require addition of thrombin to coagulate.

A dry mixture with coagulating agent (thrombin) in could be reconstituted in the container in which it was intended to be cast.

Defining the Characteristics of the Invention

The invention is a type of fibrinogen mixture with allows:
1. Stabilisation of the solution before coagulation;
2. Compatible surfactant(s) with high foam stability;
3. Compatible colligative bulking agent(s);
4. Enzymatic coagulation by addition of thrombin or other fibrinogen-selective protease.

Scaffolds produced by the process of the invention, using formulations of the invention, have well defined density, porosity, micro-scale structural homogeneity, and are very hydrophilic. These features are all very important in terms of how the product functions and how it achieves its end results. The characteristics of the product must be controllable and reproducible in order for it to be useful as a commercial product (for example for wound healing).

Extracellular matrix compositions (dermal scaffold compositions) of the invention are able to support cellular adhesion in vitro and neovascularisation in vivo; are rigid enough to resist collapse caused by in-growing cells and are sufficiently resistant to proteolytic degradation so as to survive in a wound environment for fibro-proliferation to occur. These properties can be achieved by the product of the process of the present invention.

The object of the invention is to provide a stable homogenous open pore extracellular matrix composition that actively interacts with cells particularly to promote endothelial cell adhesion. In this context, the term "extracellular matrix" is stated to refer to a structure to which cells can adhere and multiply without causing toxicity or inhibition of cell replication.

In this invention, the process requires the use of a coagulating agent which ensures the formation of a stable gel. It also requires a compatible foaming agent, and a colligative bulking agent which controls the microstructure. The preferred formulations also contain a protein stabilising agent (most preferably trehalose).

The fibrinogen used in this invention may be essentially pure, or may contain a trace of one or more other components. It is currently preferred that the fibrinogen should not contain a significant amount of other protein(s). For example, one commercially available fibrinogen preparation (intended for use as an i.v. infusion) contains about 35% albumin and is not preferred (although the additional protein could be removed by dialysis to leave a useable fibrinogen product).

INDUSTRIAL APPLICABILITY

Smart Matrix Synthetic Dermal Replacement

One embodiment of the scaffold type of the invention is a dermal replacement scaffold. The Smart Matrix Synthetic Dermal Replacement (SDR) is a tissue repair scaffold intended for the treatment of large, full thickness skin loss wounds, which cannot heal by primary intention. There are three generic categories of such wounds:
1. acutely traumatic tissue loss, e.g. burns, blast wounds, de-gloving injury.
2. surgical resection wounds, e.g. large squamous cell carcinoma/melanoma.
3. chronic wounds, e.g. venous leg ulcers, diabetic foot ulcers and pressure sores.

There are products currently on the market that are used to treat these wounds many of which also require subsequent treatment by split thickness skin grafting. The SDR is a biomaterial that is intended to improve on the performance of currently available products. It provides the conditions for more rapid vascularisation and cellular integration to occur and thus enables a more reliable 'take' of the graft on these difficult wounds thus improving the rate and quality of wound healing. It may be used with disaggregated skin cells or other means of reconstituting the epidermis. The SDR may also be used to assist the healing of wounds without application of a graft.

It may also be beneficial for other uses, for example partial thickness wounds and donor-site wounds, as a cell delivery scaffold for tissue reconstruction, and tissue engineering applications.

Product Description

In one embodiment the SDR is a white, freeze-dried, foam-like material, between 1-5 mm in thickness and available in a number of sizes, suitable for wounds of different areas. It may be cut to the appropriate size.

Mode of Action

The SDR is a micro-porous synthetic matrix. It is a well established principle that the physical structure of micro-porous synthetic matrices provides a supportive environment for cell growth (e.g. Dagalakis et al, 1980, O'Brian, 2005). The SDR allows the rapid ingress of cells that are instrumental in tissue regeneration leading to rapid cellularisation and neovascularisation of its structure. The SDR is resorbable (being susceptible to enzymatic proteolytic degradation) and by the time cellularisation is complete, the SDR has been substantially degraded.

Characteristics of the SDR in Use

Assists wound healing in full-thickness skin loss
Functions as a regeneration scaffold
Supports rapid revascularisation and cell growth
Results in stable neodermis ready for split thickness skin grafting Indications Use in full-thickness skin loss from acute trauma, surgical resection or chronic ulceration.

The product is intended to aid skin reconstruction as an adjunct to the recognised clinical treatment for full-thickness wounds. For chronic ulcers, the underlying cause of the ulceration will require appropriate clinical management.

Instructions for Use

Wounds must be surgically debrided or otherwise cleared of necrotic and infected tissue debris prior to treatment with the SDR under sterile conditions.

The SDR may be hydrated, for example, in sterile saline solution prior to application. The procedure is to soak the product in a tray of saline for at least 5 minutes prior to use, verifying that hydration is complete by the change in appearance from opaque white to translucent white.

The SDR may be used in combination with a transparent dressing material (e.g. Mepitel or Mepiform) as a bilayer. This protects the SDR and allows a period of integration with the wound prior to application of a skin graft as a delayed procedure. After verification of take, as evidenced by a change in colour of the SDR from white to pink, the material may then be grafted with a split thickness skin graft.

Alternatively, the SDR may also be used as a single-stage reconstruction, by applying it to the wound (without a backing material), and immediately placing a split-thickness skin graft over it. A standard dressing should then be applied (e.g. Mepitel™, Jelonet™) or an absorbent dressing such as a foam dressing (e.g. Mepilex, Mepilex Border or Alevyn). Gentle continuous pressure may be applied by the use of a bolster dressing.

The product may be applied to the wound by lifting it out of the saline soaking tray onto a sterile gauze swab to transfer it. Alternatively it may be handled directly, using appropriate care to avoid tearing the product. It may be cut to size dry or wet (e.g. supported by a gauze pad for cutting to a template).

The product may be secured in place by sutures or staples. This will be more secure when a backing sheet is used over dressings, bolster dressings and splinting should be considered according to clinical need.

How the Product Will be Presented to the Market

The SDR will be presented sterile, individually packed in a foil-sealed tray within a peel-apart pouch.

REFERENCES

Dagalakis, N., J. Flink, P. Stasikelis, J. F. Burke and I. V. Yannas (1980). "Design of an artificial skin. Part III. Control of pore structure." *J Biomed Mater Res* 14(4): 511-28.

O'Brien, F. J., B. A. Harley, I. V. Yannas and L. J. Gibson (2005). "The effect of pore size on cell adhesion in collagen-GAG scaffolds." *Biomaterials* 26(4): 433-41.

METHODS

Coagulation

Figure 1:
FIG. 1. Eosin staining histological section of the optimised Smart Matrix™ formula #1.

Candidate mixtures were prepared in 1 ml optical cuvettes and monitored at 425 nm. Mixtures were prepared first without thrombin, and baseline absorbance data was measured against a water blank. Thrombin was then added, mixture mixed by inversion (parafilm) and absorbance was measured every minute until coagulation was complete. Data for lag time and maximum coagulation rate were derived from each profile. At the end of coagulation, scaffolds were manually assessed for gel stiffness and scored subjectively on a percentage scale, comparing fibrin clot without surfactant as a 100% gel.

Coagulation Experiments

Method:

Mixing test constituents with fibrinogen and measuring Optical Density (OD) at 425 nm over time to measure solution turbidity ie cloudiness (similar results would be obtained by measuring at any wavelength over a broad range).

The sequence of mixing is:

Calcium ($CaCl_2$ 2 mM unless stated), from a concentrated stock solution (e.g. 1M CaCl2)

fibrinogen (human or bovine: hFbg/bFbg), (Fybex is hFbg, Bioproducts Laboratories, Dagger Lane, Elstree, Herts, UK).

diluent (Typically HEPES/NaCl; HEPES 25 mM, NaCl 150 mM pH 7.4),

Table of concentrations of key components of Smart Matrix optimised formulae.

| | Pluronic SM formula 1 | | SM-OF1 | | SM-OF2 | | SM-OF3 (DMP or DSuc alternatives) | |
|---|---|---|---|---|---|---|---|---|
| | reagent conc | final mix conc | reagent conc | final mix conc | reagent conc | final mix conc | reagent conc | final mix conc |
| Fbg | 2% | 0.87% | 2% | 0.8% | 2% | 0.9% | 2% | 0.9% |
| CaCl$_2$ | 1M | 2 mM | 1M | 2 mM | 1M | 2 mM | 1M | 2 mM |
| Trehalose (Tre) | — | — | 66% | [11% with Fbg] | 66% | [11% with Fbg] | 66% | [11% with Fbg] |
| Thrombin (Thm) | 10 U/ml | 0.0625-0.125 IU/mg Fbg | 10 U/ml | 0.125 IU/mg Fbg | 10 U/ml | 0.125 IU/mg Fbg | 10 U/ml | 0.125 IU/mg Fbg |
| AA | 2% | 0.87% | 2% | 0.8% | 2% | 0.46% | 2% | 0.46% |
| Surfactant | Pluronic F68 20% | 0.7-1.5% | OGP 20% Pluronic F68 20% | 0.93-1.86% 0.24-0.475% | DMP 20% DdGP 20% ODM 20% Pluronic F68 20% | 0.48% 0.24% 0.24% 0.24% | DMP 20% nDSuc 20% | 0.53% 0.53% | stabiliser (preferably trehalose, added from a saturated stock solution),
bulking agents (typically alginic acid (AA) dissolved in HEPES/NaCl),
surfactant
   then mix and make pre-coagulation measurements,
   then add thrombin at coagulation t=0
   measure OD every minute until coagulation is complete, or the OD is off scale (>2.5).
The main variables studied are:
ionic strength (25-400 mM NaCl)
anion and cation effects ($K^+$ substitution for $Na^+/SO_4$ or HEPES substitution for $Cl^-$)
ionic environment (effect of buffer pKa with MES, HEPES, TRIS)
pH (6.7-7.4)
effect of bulking agent, alginic acid
effect of small carbohydrates (glycerol, sorbitol, glucose, sucrose, trehalose)
effect of non-ionic surfactants (Pluronic series F127 & F68) Tween 20, Triton X100 and OGP.

| Code | Experimental conditions | Summary result |
|---|---|---|
| A | Thrombin 0.25-1.5 U/1% hFbg (Fybex)/ml ($CaCl_2$ 10 mM) | thrombin increases coagulation |
| | Calcium ($CaCl_2$ 2-10 mM) (thrombin 0.25-1.5 U/1% hFbg (Fybex)/ml | calcium increases coagulation |
| | Pluronic F68 (3%) or high NaCl (0.45M) | pluronic causes Fbg precipitation high NaCl inhibits coagulation |
| B | high NaCl (0.45M)/ ($CaCl_2$ 2-10 mM) thrombin (0.25-0.75 U) | high NaCl profoundly inhibits coagulation, independently of calcium and thrombin. |
| C (3 runs) | Calcium ($CaCl_2$ 10-50 mM) Thrombin (0.25-0.75 U)/1% hFbg (Fybex)/ml F68 (0.5-1.5%) (Thrombin 0.1 U/ml) | 25 mM Ca approx optimal for coagulation. F68 at 0.5% does not cause Fbg precipitation, but does at 1.5%. F68 accelerates coagulation but decreases gel strength. At 1.5% F68, clotting inhibited although coagulation v. rapid |
| | F68 (0.5-1.5%) + AA (0.78%) | AA addition with F68 accelerates coagulation with partial clotting |
| D (2 runs) | HEPES NaCl (80-150 mM) F68 (0.5-1.5%) | ionic strength 80 mM NaCl increases coagulation rate F68 0.5% addition in 80 mM NaCl increases Fbg precipitation and coagulation rate. F68 1.5% addition in 80 mM NaCl increases Fbg precipitation and coagulation rate. |
| (6 runs) | HEPES NaCl (50-150 mM) F68 (0.5%) | ionic strength <80 mM inhibits coagulation ionic strength c.40 mM causes some Fbg precipitation |
| E 2 runs | HEPES (20-150 mM) (NaCl 25 mM) | HEPES >60 mM needed to maintain Fbg solubility |
| | HEPES/NaCl (150-750 µl) Fbg (0.5%, 84 mM NaCl) 250 µl | c100 mM NaCl/15 mM HEPES needed to keep Fbg in solution when Fbg precipitation formed initially, solution failed to clot |
| F | substitution of HEPES NaCl (150 mM) by HEPES (150 mM) | small effect on coagulation dynamics More HEPES causes slight Fbg precipitation. |
| G | F68 (0.12-0.5%) HEPES NaCl (75-150 mM) (Fbg 0.5%, 37' C. pre-warming) | F68 up to 0.5% increases coagulation rate. Reduction of ionic strength has little effect at 0.5% F68 but slight precipitation. |
| H | F68 (0.1 2-0.5%) HEPES NaCl (150 mM) (Fbg 0.5%, 4', 10' 20' 37' C. incubation) | precipitation observed none at 37' C., v slight at 20' C., slightly at 10' C., very large at 4' C. - F68 slightly amplifies these effects. Re-warming reverses effects Coagulation faster with F68 |
| | As above with lower ionic strength | F68 0.5% causes precipitation with c 100 mM HEPES NaCl, compared to 150 mM |
| | As above, with Pluronic F68 vs F127 at 0.5% | F127 causes less precipitation than F68 in 100 mM HEPES NaCl |
| | F127 (0.12-0.5%), (HEPES NaCl 150 mM, 0.5% Fbg) | F127 slightly accelerates coagulation w/o initial precipitation |
| I | F68 or F127 (0.25-0.5%), (HEPES/NaCl c.100 mM, 0.5% hFbg) | warming from RT to 37' C. clears precipitation - rapid coagulation |
| | 0.5% F68, AA in 75 mM NaCl/HEPES or AA in 150 mM NaCl/HEPES, 0.5% hFbg | 0.5% F68 increases Fbg precipitation in AA/Fbg mixture - elevated NaCl counteracts to reduce precipitation. |
| J | 0.5% F68 and 75 or 150 mM NaCl 0.5% hFbg | F68 0.12-0.5% progressively increases Fbg precipitation, but higher NaCl counteracts this. Elevation of temp from 20 to 37' C. prior to F68 addition prevents precipitation. Cooling to 4' C. increases precipitation, reversed on re-warming. F68 |

| Code | Experimental conditions | Summary result |
| --- | --- | --- |
| | | increases coagulation rate, also faster in F68 with 150 mM NaCl than 75 mM NaCl. |
| K | F68 or F127 in 75 mM NaCl 0.5% hFbg | F68 F127 have very similar effects on coagulation rate, and similar effects with temperature of hFbg precipitation. |
| | 0.12-0.5% AA in 75 mM NaCl/HEPES, 0.5% hFbg, 20' C. or 37' C. | 0.25% AA is threshold for causing hFbg precipitation, 0.5% causes this, but the effect is reduced by 37' C. pre-warming. AA addition progressively accelerates coagulation |
| | 0.5% AA, 0.5% hFbg, 75 or 150 mM NaCl/HEPES | 0.5% AA causes hFbg precipitation in 75 but not 150 mM NaCl. Coagulation is accelerated by AA. |
| L | 0.5% F68, 0.5% AA, 0.5% hFbg, 75 or 175 (up to 200) mM NaCl/HEPES | Combination of F68 and AA cause some precipitation at up to 200 mM NaCl even after 37' C. incubation. AA accelerates coagulation more than F68, but F68 gives stronger gel. |
| M | NaCl, KCl, HEPES, TRIS, in 25 mM NaCl/HEPES 0.5% hFbg, 0.5% AA, 0.5% F68 | KCl causes more hFbg precipitation than NaCl, HEPES causes more than TRIS. |
| N | NaSO4 (60-240 mM), 0.5% hFbg, 0.5% AA, 0.5% F68 | NaSO4 increases Fbg precipitation progressively over 60-240 mM. |
| O | NaCl up to 300 mM 0.5% hFbg, 0.5% AA, 0.5% F68 | high hFbg precipitation but slightly reduced with increased NaCl |
| P | 400 mM NaCl 0.5-1% hFbg, 0.5% AA, 0.5 or 1.5% F68. | high hFbg precipitation |
| Q | 0.25-1% AA in 150 mM NaCl/HEPES, 0.5% hFbg, warming to 37' C. | 0.7% AA is threshold mix for 0.5% hFbg before precipitation (in absence of F68) |
| | 0.25-1% AA in 150 mM NaCl/HEPES, 0.5% hFbg, 0.125-0.25% F68, warming to 37' C. | At 0.5% AA/0.5% hFbg mix, 0.125 is the limit before precipitation. |
| R | 0.25-1% AA, 1% hFbg in 150 mM NaCl/HEPES, warming to 37' C. | All mixtures stable, AA progressively accelerates coagulation |
| | 1-1.25% AA, 1% hFbg, 0.125-0.5% F68 in 150 mM NaCl/HEPES, warning to 37' C. | 0.125% F68 is threshold for precipitation |
| S | 1% AA 1% hFbg, 0.125-2% F68, 20% glycerol | Glycerol prevents precipitation of mix up to 1% F68 addition to 1% AA: 1% hFbg. However, coagulation completely inhibited by glycerol. |
| | 1% Tween 20 or 1% Tx100 or 0.25% F68, with 1% AA 1% hFbg, warming to 37' C. | 1% Tween20 on threshold of precipitation and inhibits coagulation. 1% Triton X100 causes some Fbg precipitation but slightly accelerates coagulation. 0.25% F68 cause similar precipitation but accelerates coagulation most. |
| T | 1% AA 1% hFbg, 2.5-5% glycerol ± 0.5-1% F68 | Glycerol progressively inhibits coagulation (5% doubles time to clot). 5% glycerol does not prevent precipitation with 0.5% F68. |
| U | hFbg 1%, AA 1%-2.5%, glycerol 5-10% | Glycerol partially but not completely prevents precipitation at AA at 1.75% or more. |
| V | Sorbitol 32%, or glycine 50-200 mM, with glycerol 5% F68 0.5%, hFbg 1%, AA 0.5-1% | Sorbitol addition inhibited coagulation. Glycine increased initial precipitation and accelerated coagulation. |
| | TRIS NaCl pH 7.4 or MES NaCl pH 6.8 compared with HEPES NaCl pH 7.4, glycerol 5% F68 0.5%, hFbg 1%, AA 0 or 1% | MES increased coagulation rate with AA, compared to HEPES, TRIS inhibited. Coagulation inhibited (by glycerol) in absence of AA with any buffer. |
| W | Sucrose 10-20%, hFbg 1%, AA 1%, HEPES/NaCl | 10% & 20% sucrose reduced precipitation, but profoundly inhibited coagulation - formed clear transparent gels. |
| | Sucrose 20%, hFbg 1%, AA 1%, HEPES/NaCl, F68 0.5-3% | addition of up to 3% F68 to mixture does not cause precipitation. Coagulation without intact gel formation occurred at 3% F68. |
| X | Sucrose 10-20%, hFbg 1%, AA 1%, HEPES/NaCl, F68 0.5% | 10 & 20% sucrose prevent precipitation by F68 addition to hFbg/AA mix. |
| Y | AA1%-2.5%, bFbg, 1%, glycerol 10%, bFbg 1% | AA at 1%-2.5% caused progressive precipitation. This was reduced by glycerol addition. Coagulation & gel formation occurred with AA at 1.75% and above. Ie AA overcame glycerol inhibition effect. |
| | AA + 10% glycerol (0.5-1%), bFbg 1%,, bFbg 1%, F68 0.5-2% (additional glycerol 5%) | Coagulation inhibited without F68 (due to glycerol). >0.5% F68 caused progressive |

| Code | Experimental conditions | Summary result |
|---|---|---|
|  | AA 0.5%, bFbg 1%, glycerol 5%, F68 0.5-2% | precipitation, and accelerated coagulation. 1% AA/5% glycerol with 0.5% F68 cleared at 37' C. and coagulated normally. F68 at 1% is threshold for precipitation, but gives normal coagulation. F68 at 0.5% gives inhibited coagulation. Ie ratio of glycerol, F68 and AA together determine precipitation. |
| Z | Sucrose 4.7-23.5%, hFbg 1%, AA 1%, HEPES/NaCl, ±F68 0.5% | Sucrose w/o stabilises Fbg in mix by warming at 37' C., but inhibits coagulation, and results in eventual clear gel formation. F68 addition w/o sucrose causes Fbg precipitation (partially reversed on warming to 37' C., and very rapid coagulation. Sucrose plus F68 pre-warmed prevents Fbg precipitation, and coagulation proceeds normally. |
| A2 | AA (0, 0.5%, 1%), F68 (0.5-1%) bFbg 1%, MES pH 7.4, | 0.5% AA with 1% Fbg and up to 1% F68 is limit for precipitation formation after warming to 37' C. |
| B2 | OGP (0.25-2%), bFbg 1% HEPES/NaCl | OGP up to 2% does not cause precipitation of bFbg. However it inhibits coagulation but results in transparent gel formation. |
|  | OGP (0.25-2%) ± F68 (0.5-1%), bFbg 1% HEPES/NaCl | OGP 0.5% + F68 0.5% do not cause precipitation, but at 1% mix does. The 0.5% mix accelerates coagulation over control, but slightly less that F68 alone at 0.5%. |
|  | OGP (0.25-2%), AA 1%, bFbg 1% HEPES/NaCl | OGP addition reduced precipitation progressively up to 1.5% and was stable up to 2%. Coagulation of the mix was inhibited at 0.5% or less, and increased at 1% but less than control at 1.5 or 2%. |
|  | OGP (0.25-2%) ± F68 (0.5-1%), AA 1%, bFbg 1% HEPES/NaCl | High initial precipitation in all samples in this run. However, at 1% OGP + 0.5% F68 accelerated coagulation seen |
|  | OGP (0.1-3.3%) ± Trehalose (6%), AA 1%, bFbg 1% HEPES/NaCl | High initial ppt in all samples in this run but warming 10°, 37° C. reduced turbidity. Increasing OGP to 2% reduced from 0.426 (no OGP) to 0.153 (3.3% OGP). 1.8% OGP + 6.6% Trehalose reduced OD to 0.099. Effect on coagulation - increasing OGP inhibited coagulation (complete by 5 min control to 15 min with 2% OGP, and OGP/Trehalose 16 min. |
| C2 | Trehalose (3.3-19.8%), Fbg 1%, HEPES/NaCl | no initial precipitation over range. Progressive inhibition of coagulation over range. 6.6% trehalose gives approx 0.5X time to coagulate. |
|  | Trehalose (3.3-6.6%), OGP 1%, F68 0.5%, Fbg 1% AA 1% | Trehalose 3 & 6% slight inhibition of coagulation. With 3.3% trehalose, OGP + F68 is slightly inhibited, but with 6.6% trehalose, coagulation is less inhibited than without surfactants. |
| D2 | hFbg 1%, HEPES pH 7.4, MES 6.7, &.05, 7.4 in NaCl | Coagulation rate: MES 6.7 > 7.05 > 7.4 > HEPES 7.4 |
|  | OGP (1-5%), 1% hFbg, HEPES pH 7.4 | OGP gives no Fbg precipitation, progressively inhibits coagulation - but gives transparent gels |
|  | OGP (2-4%), F68 (0.5-1%) 1% hFbg, HEPES pH 7.4 | 3% OGP + 1% F68 gives faster than control coagulation. Increased ratio of F68 causes initial precipitation & further accelerates coagulation (partially reversed on warming to 37' C.) |
|  | OGP (2%), F68 (0.5-1%) AA 1%, 1% hFbg, HEPES pH 7.4 | AA greatly increases coagulation compared to previous control. With 2% OGP this is slightly inhibited. With 2% OGP + 0.5% F68 it is greater than the AA control, but with initial precipitation on warming to 37' C. |
|  | OGP (2%), F68 (0.5-1%) AA 1%, trehalose 6.6% 1% hFbg, HEPES pH 7.4 | Trehalose reduces precipitation due to 2% OGP + 0.5% F68 (more on warming to 37' C.) |

Discussion:

These studies evaluate factors (potential components of Smart Matrix manufacture mix) which influence the solubility and enzymic (thrombin-catalysed) coagulation of fibrinogen.

The principle of this experimental system is to measure precipitation and coagulation by increase in turbidity in a 1 ml volume in a cuvette. A caveat is that fibrinogen coagulation in some conditions develops with reduced turbidity, and increased turbidity does not necessarily indicate physical gellation. However, inspection of the reaction mixes can readily establish these exceptions.

The complexity of the Smart Matrix manufacture mixture results in problems for the optimisation process. A primary consideration is that while physicochemical factors which influence solubility of protein in an aqueous buffered solution are relatively easy to understand (eg ionic strength, pH), the addition of a second component, in this case alginic acid, introduces potential competing physicochemical interactions between the two macromolecular species, and hence complexity into predicting the outcome (eg precipitation). The sequence of experiments presented here was influenced by an expedient search for significant effects among several potential variables.

Summary & Conclusion from the Experiments
Effects on Fibrinogen Precipitation and Coagulation
Ionic Strength Elevated ionic strength causes proportionate inhibition of coagulation rate, and low ionic strength causes precipitation. Increasing ionic strength to around 60 mM has a salting-in effect on fibrinogen solubility.

NaCl maintains Fbg solution with surfactant (e.g. decrease from 150-100 mM results in Fbg precipitation caused by 1% F68).
Anion and Cation Environment Substitution of potassium for sodium increases Fbg precipitation.

Substitution of chloride by HEPES, TRIS or sulphate increases Fbg precipitation.

Glycine (up to 0.2M) increased Fbg precipitation and accelerated coagulation.
pH Coagulation is faster at 6.7 than 7.4, but varies with buffer system: MES>HEPES>TRIS (ie the buffer with lower pKa gives faster coagulation in the Fbg/AA mixture).
Bulking Agent Alginic acid (AA) causes Fbg precipitation and accelerates coagulation, around equi-mass/volume as Fbg (1%). Effect reduced by warming to 37° C.
Small Carbohydrates and Poly-Ols Glycerol (5-10%), sorbitol (22-32%), sucrose (15-50%), raffinose, and trehalose (10-66%) reduce Fbg precipitation and inhibit coagulation.

These also reduce the Fbg precipitation on addition of alginate and/or surfactants.
Non-Ionic Surfactants Pluronic F127 or F68 cause Fbg precipitation above 0.5%, and accelerate coagulation
  decreased by increasing ionic strength, warming to 37° C., small carbohydrates (glycerol, sorbitol, sucrose, trehalose)
  increased by alginic acid, cooling to 4° C.

Tween 20 causes some Fbg precipitation in Fbg/AA mix, inhibits coagulation (Addition of small fraction of F68 increases Fbg precipitation).

Triton X100 at 1% causes Fbg precipitation in Fbg/AA mix, slightly increases coagulation (Addition of small fraction of F68 increases Fbg precipitation).

OGP does not cause Fbg precipitation up to 2% but inhibits coagulation progressively with concentration.

OGP mixture with Pluronic F68 has a balancing effect, resulting in a balance, where Fbg precipitation is prevented while coagulation rate is normalised (rather than inhibited).

The Pluronic surfactants are non-classical, block copolymers. The basis of the solution interactions with these dissolved macromolecules is not known. It is possible that there is a rapid competitive interaction between pluronic, protein and alginate. Pluronic may interact with protein initially due to hydrophobic aggregation and precipitation. This may be thermally reversed due to increase in the entropy of the solution. Also, a long-term shift in solubility of complex mixtures has been seen, with initial precipitate gradually re-dissolving, a process which is accelerated by warming to 37° C.

le;2qWhether this secondary effect is due to chemical changes, perhaps non-enzymic hydrolysis of fibrinogen peptides, or due to establishing of semi-stable non-covalent interactions between macromolecules, is not known. Pluronic and other surfactants do not precipitate alginate. The combination of alginate with different surfactants gives differences in solubility of admixed fibrinogen. The effect of small sugars is likely to increase the entropy of the free aqueous phase by substituting for water of hydration around protein molecules. These interactions are complex, and predicting the outcomes of various changes on theoretical grounds (eg Flory-Huggins theory) based on specific thermodynamic data (which is not available) probably would be successful in the absence of a comprehensive and accurate computational model of the system.

General Conclusions:

One general conclusion from these experiments is that certain factors have an effect which tends to increase protein solution stability and also to inhibit enzymic coagulation (e.g. NaCl, glycerol, sucrose, trehalose, OGP).

Certain other factors have an effect which tends to increase precipitation of Fbg and also to accelerate enzymatic coagulation (e.g. alginate, Pluronic F68, F127).

This is not an obvious result, since protein solubility might be thought to be a prerequisite for free diffusion of enzyme and substrate molecules.

A corollary result is that several agents combinations have overlapping concentration ranges in which they may have an effect of either (i) solution stabilisation and inhibition of coagulation, or (ii) acceleration of coagulation and causing precipitation. This limits their utility.

Another surprising element of these results is the finding that, while increasing fibrinogen solubility, small carbohydrates and poly-ols are potent inhibitors of coagulation. Although known for stabilising protein structures on freeze drying, their solution effects on fibrinogen coagulation, or other similar enzymatic systems in vitro, has not been reported in the literature.

A more specific surprising element of the results is that the effect of non-ionic surfactants varies widely between (i) maintaining fibrinogen in solution in the presence of alginate (e.g. OGP), and (ii) causing precipitation of fibrinogen (e.g. Pluronic F68, F127, Tween20, Triton X100).

These are non-obvious results since non-ionic detergent solutions are generally known for dissolving proteins.

These data alone are not sufficient to completely derive a successful scaffold manufacturing formulation. In addition, foam stability data is needed, since the surfactant used in the mixes must be able to create dense foam and support it for sufficient time to allow fibrinogen coagulation. Even the best candidate formulations from combined control of coagulation and precipitation will require to control of the foam in order to achieve a scaffold with an optimal structure and biological efficacy. The simultaneous control of the three key processes of foam formation, coagulation and precipitation is not trivial, and the way to achieve it is not obvious from known scaffold formulations and known matrix production processes.

Scaffold Manufacture Experiments

Scaffolds were manufactured according to a standardised procedure. Briefly, this involves:
1. Preparation of all reagents
2. Sequential addition of reagents to a mixing chamber (Inverted open-ended syringe). Calcium chloride, fibrinogen, trehalose, thrombin, then after 10 seconds of gentle swirling, alginate, then vigorous mixing (whisk, 6000 rpm) is started and continued for 30 s, with surfactant added at 15 s;
3. Casting and incubating at 37° C. in a humidified incubator;
4. Cross-linking with 0.2% glutaraldehyde in 0.1 M MES pH 7.4, 80% ethanol (4 h);
5. Reduction with 0.1% sodium borohydride (aq), 1 hr followed by 4×10 minute washes;
6. Washing with water, 5×10 min washes;
7. Lyophilisation.

N.B. Calcium chloride, fibrinogen and trehalose can be pre-combined. Addition of thrombin started the coagulation process.

Microscopy & Imaging

Samples were cut from prepared scaffolds with a scalpel, and wax-embedded for 'histological' processing. Sections were cut (5 um) and stained with eosin using standard histological method, and mounted in DPX for microscopy. Serial micrographs were recorded of sections at 10× using a LeicaDC200 digital camera and LC50 Image software interface. Serial images were digitally 'stitched' together (ICE software) for assessment.

Scaffold Assessments (i) Image-Analysis (Pore Size Distribution)

Individual pore sizes in micrograph sections of scaffolds were measured with ImageJ software.

(ii) Microstructure and Homogeneity

Images were assessed for pore size, lamella density and homogeneity of pore size and top-bottom distribution.

(iii) SEM

Some scaffold formulations in this series of experiments were evaluated:
(i) in vitro, for ingress of fibroblasts.
(ii) in vivo, for integration in a porcine full-thickness wound healing model.

Some scaffolds were imaged by SEM for corroboration of LM analysis.

Table of Sugar Surfactants tested

| DETERGENT | ABBR | CRITICAL MICELLE CONC (CMC) (mM) | HYDROPHILE-LIPHOPHILE BAL (HLB) | MW (g/mol) |
|---|---|---|---|---|
| Octyl β-D-glucopyranoside | OGP | 20-25 | 11.1 | 292 |
| Sorbitan - laurate | SPAN-20 | 2.1-2.4 | 8.6 | 346.46 |
| Sorbitan - palmitate | SPAN-40 | 1.6-1.9 | 6.7 | 402.57 |
| Sorbitan stearate | SPAN-60 | 1.6-1.9 | 4.7 | 430.62 |
| Sorbitan oleate | SPAN-80 | 1.6-1.9 | 4.3 | 428.61 |
| n-Octyl β-D-maltoside | ODM | 19.5 | 14.3 | 454.51 |
| Decyl β-D-glucopyranoside | DGP | 2.2 | 10.2 | 320.42 |
| Octyl β-D-thioglucopyranoside | TGP | 9 | 10.6 | 308.44 |
| Hexyl β-D-glucopyranoside | HGP | 250 | 12.3 | 264.31 |
| n-Dodecyl β-D-glucopyranoside | DdGP | 0.19 | 9.4 | 348.5 |
| n-Decyl β-D-maltoside | DMP | 1.8 | 13.5 | 482.6 |

*HLB = MW (hydrophilic group)/MW × 20

A3—Smart Matrix™ Optimized Formulation SMOF #1

OGP is a detergent used to dissolve integral membrane proteins and it can readily be removed from final protein extract. OGP is dissolved in dH$_2$O at a concentration of 20% wt and is used as a surfactant in the current formulation because it forms a relatively stable foam and also has a relatively high compatibility with fibrinogen solubility in coagulation studies. OGP is used along with a Pluronic (F-68) in the ratio 4:1 because this ratio was found to be most effective in stabilizing the foam. This formula was effective at producing sizeable stable foam as confirmed by visual, histological, and coagulation assay analysis. Trehalose was selected as a "poly-ol" with solution stabilising effects but less potent inhibition of thrombin coagulation than other poly-ols. This formulation has been termed 'Smart Matrix™ Optimized Formulation #1'. The specific formula is:—

Smart Matrix™ Optimised Formulation #1 (in Order of Addition)

1. 1M CaCl$_2$ stock soln. prepared in dH$_2$O (16.2 μl—resulting in about 2 mM in the mix)
2. 2% wt. Fibrinogen protein prepared in Mes/NaCl (3 ml)
3. 66% wt. saturated stock soln. Trehalose prepared in dH$_2$O (600 μl)
4. Thrombin (750 μl) 10 IU/ml stock
5. 2% wt. Alginic Acid prepared in Mes/NaCl (1.5-3 ml)
6. 20% wt. OGP prepared in dH$_2$O and mixed with 20% wt. F-68 in the ratio 4:1 (750 μl)

This formula was used in the subsequent experiments to investigate different surfactants (p29-41) except the surfactant component in 6 of the above mixtures was varied.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| 20% OGP/20% F-68 (4:1) (750 µl) | Foamed well (50 ml) | Large bubbles on the top of scaffold when compared to the base | Collapsed a lot on addition of cross linking agent | Few large bubbles persistent in the scaffold top to bottom differences persisted |

Summary of Results

Production of a scaffold via 'SMOF #1' exhibited good foaming, completely filling up the 60 ml mixing vessel. Coagulation studies showed a slight inhibition of onset of coagulation, but good protein solution stability and the resulting gel was firm and solid. After mixing, the foam exhibited fluid characteristics and was easy to tap down to an even level following casting. After one hour of coagulation period, there was a noticeable difference in the size of the bubble formed from the top of the foam compared to the base, with larger bubbles observed on top of the scaffold. This difference was maintained by cross linking. Histological analysis showed that bubble lamella present at the top of the scaffold were thicker than those at the bottom. In addition there was a minor, but observable difference in the pore size at the top of the scaffold compared to the base. This leads to a reduction in homogeneity of the scaffold, even though it is better than previous experiments FIG. 1. Eosin staining histological section of the optimised Smart Matrix™ formula #1.

Figure 2:
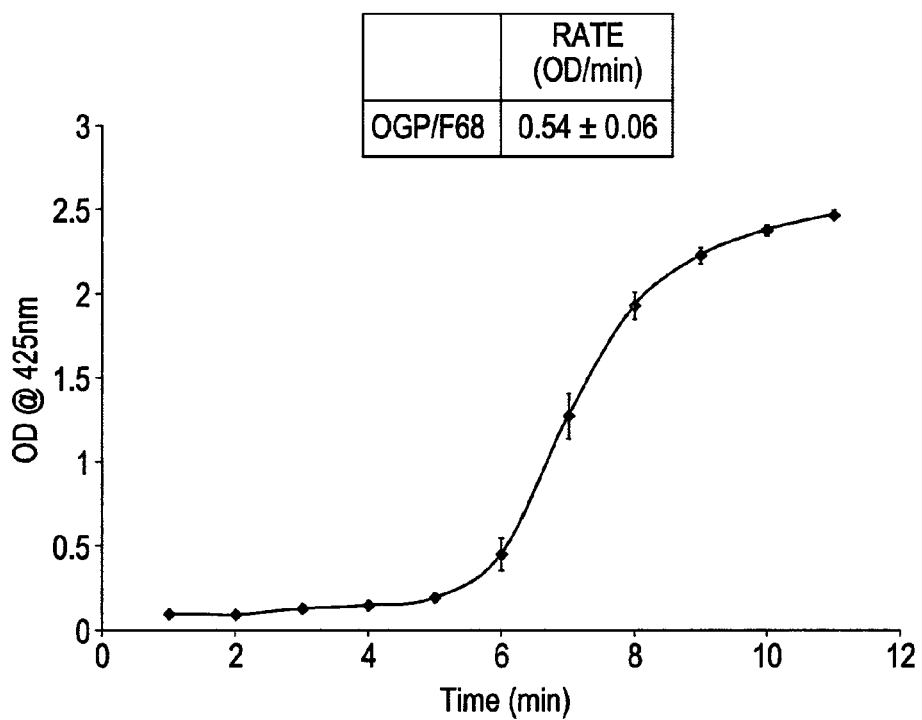
FIG. 2. Coagulation results using surfactant OGP/F-68.

FIG. 2. Coagulation results using surfactant OGP/F-68.

B3—Investigation of Sorbitan Esters (Spans)

Spans are also known as Sorbitan esters and are lipophilic non ionic surfactants used as emulsifying agents in the preparation of emulsions, creams and ointments. A series of Sorbitan monoesters (Span 20, 40, 60 and 80) was studied to observe the formation of pores in the Smart Matrix™. Span 20 (S-20) and Span 80 (S-80) were available in viscous liquids whereas Span 40 (S-40) and Span 60 (S-60) were available in powder.

Attempts to dissolve Spans in $dH_2O$ were made. A 10% v. solution of S-20 and S-80 was prepared which formed a thick creamy emulsion unsuitable for our needs. Dissolving Spans in 100% ethanol resulted in a soluble mix but the span mix did not produce foam at all in the alcoholic medium. A mixture of ethanol and $H_2O$ was also prepared to dissolve the Spans but there was phase separation observed which was not suitable for our needs. Spans were dissolved in OGP (20% wt.) and F-68 (20% wt.) mix in the ratio 4:1 (standard mix used in SMOF #1) at a concentration of 1% wt/v. S-20 and S-80 dissolved and initially foamed well in this detergent mixture. However, S-40 and S-60 needed to be heated in a microwave for 5 seconds and placed in 37° C. water bath during the experiment to dissolve and form a clear solution.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| Spans (S20/40/60/80) in 20% OGP/20% F-68 (4:1) (750 µl) | Foamed well (50 ml) | Large bubbles on the top of scaffold when compared to the base | Collapsed a lot on addition of cross linking agent | Smaller bubbles but not very homogenous |

Summary of Results

The scaffold cast using the 1% wt/v Span in (OGP+F68). All Spans foamed well but completely collapsed after an hour of incubation at 37° C. Production of a scaffold via SMOF #1+ 0.0106 Span (20/40/60/80)' exhibited good foaming, completely filling up the 60 ml mixing vessel. After mixing, the foam exhibited fluid characteristics and was easy to tap down to an even level following casting. Scaffolds cast using S-80 had the least noticeable difference in the size of the bubble formed from the top of the foam to the base, when compared to the scaffolds cast using the other spans. On visual comparison to the scaffolds cast using Spans, the bubble size on top of the scaffold was smaller when compared to the scaffolds produced via SMOF #1.

Figure 3:
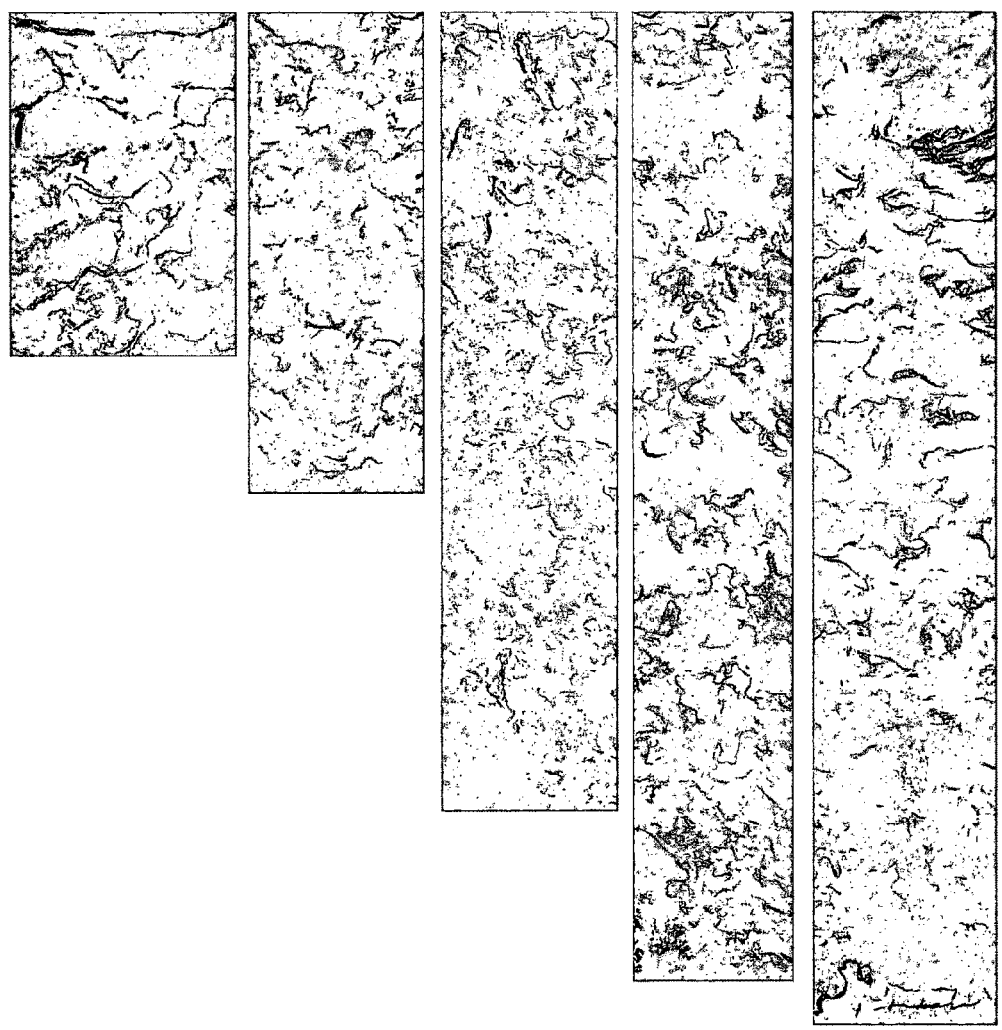
FIG. 3. Scaffolds cast using Spans.

However, importantly the microstructural homogeneity was not improved over SMOF1. In FIG. 3, dense aggregates are visable for each Span combination.

FIG. 3. Scaffolds cast using Spans.

C3—Investigation of N-Octyl β-D-Maltoside (ODM)

ODM is a water soluble non-ionic detergent closely related to OGP and is also used for solubilisation and isolation of membrane proteins. ODM has an extra 6-carbon pyranose ring due to which it has a higher HLB than OGP.

ODM was used to replace to OGP at a concentration of 20% wt. in $dH_2O$. Scaffolds produced via ODM foamed well when visually analyzed.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| 20% ODM/20% F-68 (4:1) (750 μl) | Foamed well (60 ml) | Small bubbles on the top of scaffold and to the base | Collapsed a lot on addition of cross linking agent | Smaller bubbles but not very homogenous |

Summary of Results

Production of a scaffold via 'SMOF #1+ ODM' exhibited good foaming, completely filling up the 60 ml mixing vessel. To observe the foaming ability of ODM the solution mix was prepared in a 100 ml mixing vessel and foamed up to 60% of the total volume. After mixing, the foam exhibited fluid characteristics and was easy to tap down to an even level following casting. There was considerable reduction in bubble size when compared to the scaffolds prepared via 'SMOF #1'.

Figure 4:
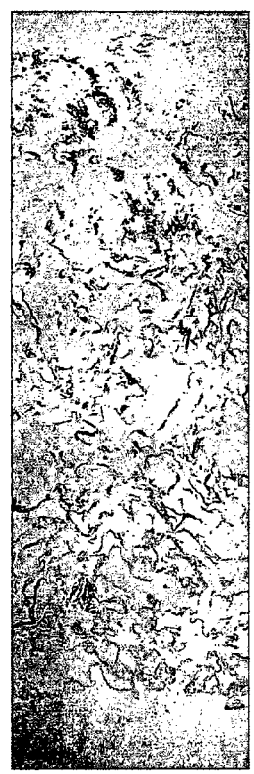
FIG. 4. Eosin staining histological section of the optimised Smart Matrix™ formula #1 +ODM.
Figure 5:
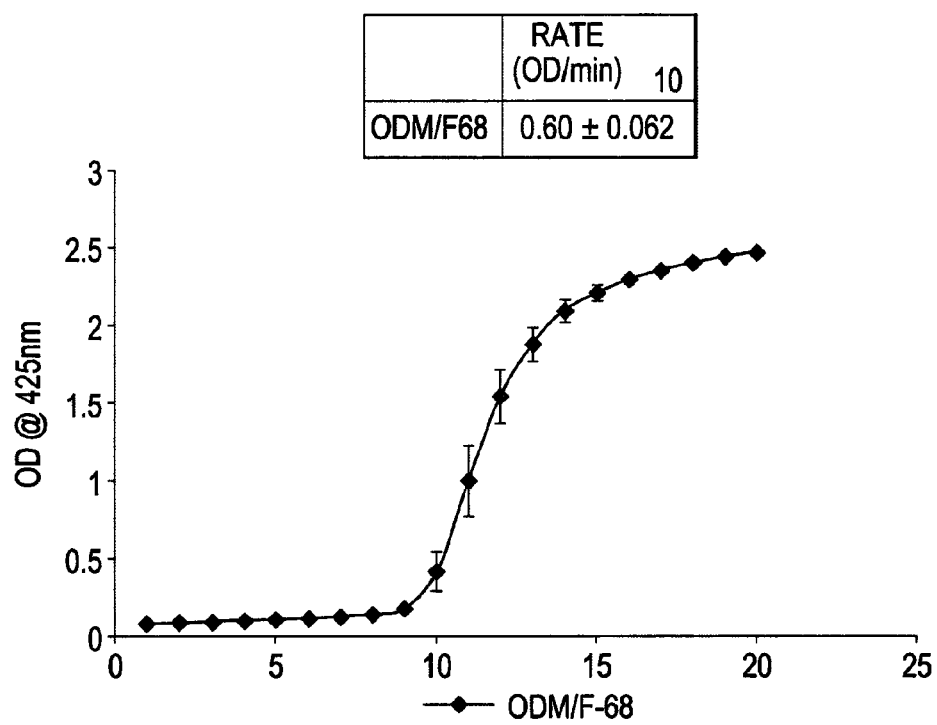
FIG. 5. Coagulation results using surfactant ODM/F-68.

FIG. 4. Eosin staining histological section of the optimised Smart Matrix™ formula #1 +ODM FIG. 5. Coagulation results using surfactant ODM/F-68.

D3—Investigation of Decyl β-D-Glucopyranoside (DGP)

DGP is a detergent of the glucopyranoside family greater lipophillicity than OGP. It is not readily water soluble and was therefore heated for five seconds in a microwave to dissolve it in dH$_2$O to make a 20% wt. solution.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| 20% DGP/20% F-68 (4:1) (750 μl) | Foamed well (40 ml) | Small bubbles on the top of scaffold and to the base | Collapsed a lot on addition of cross linking agent | Smaller bubbles but not very homogenous |

Summary of Results

Scaffolds prepared via 'SMOF #1+ DGP' were mixed in a 100 ml mixing vessel. The solution mix foamed up to 50% of the total volume of the mixing vessel and the foam exhibited more solid characteristics making it difficult to tap after casting. There was considerable reduction in bubble size when compared to the scaffolds prepared via 'SMOF #1'.

Figure 6:
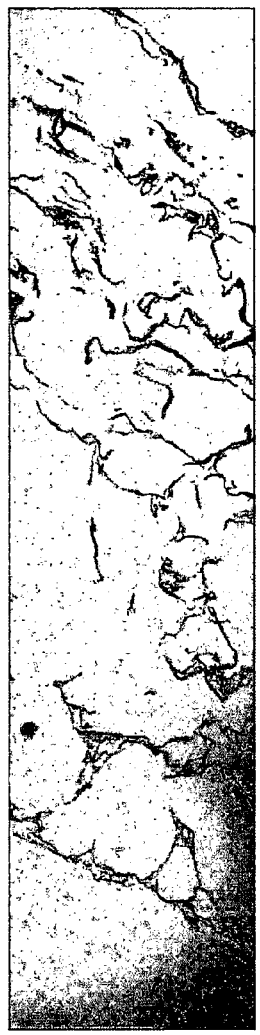
FIG. 6. Eosin staining histological section of the optimised Smart Matrix™ formula #1 +DGP.

FIG. 6. Eosin staining histological section of the optimised Smart Matrix™ formula #1 +DGP E3—Investigation of Decyl β-D-Glucopyranoside (DGP)+ OGP DGP was used at a concentration of 20% wt in dH$_2$O. It was dissolved by the addition of F-68 in the ratio 4:1 (DGP:F-68) and then heated for 15 seconds in a microwave and placed in 37° C. water bath to form a clear solution. DGP by itself does not foam up particularly well as already established in our labs, and therefore it was mixed with OGP at ratio of 3:1 to increase the foaming effect.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| (20% DGP + 20% OGP)/20% F-68 (3:1:1) (375 μl) | Foamed well (70 ml) | Small bubbles on the top of scaffold and to the base | Collapsed a lot on addition of cross linking agent | Smaller bubbles but not very homogenous |

Summary of Results

Scaffolds prepared via 'SMOF #1+ DGP/OGP' were mixed in a 100 ml mixing vessel. The solution mix foamed up to 80% of the total volume of the mixing vessel. After mixing, the foam exhibited solid characteristics and was difficult to tap down to an even level. Following casting, the foam was homogenous over the depth of the scaffold. Moreover, after incubating the scaffolds for an hour at 37° C., the bubble and pore size was considerably smaller when compared to the scaffolds prepared via 'SMOF #1'.

Figure 7:
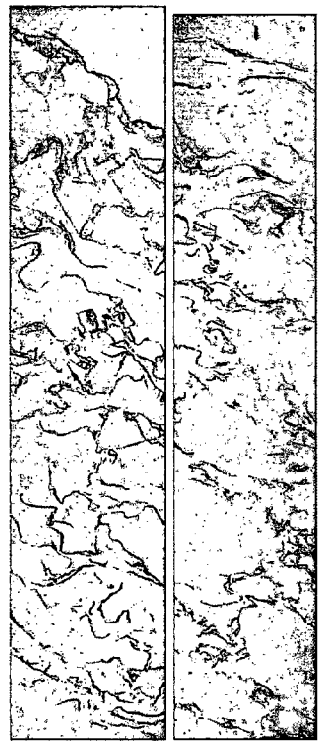
FIG. 7. Eosin staining histological section of the optimised Smart Matrix™ formula #1 +DGP/OGP.
Figure 8:
FIG. 8. Eosin staining histological section of the optimised Smart Matrix™ formula #1 +DGP/ODM.

FIG. 7. Eosin staining histological section of the optimised Smart Matrix™ formula #1 +DGP/OGP F3—Investigation of Decyl β-D-Glucopyranoside (DGP)+ODM DGP was used at a concentration of 20% wt in $dH_2O$. It was dissolved by the addition of F-68 in the ratio 4:1 (DGP:F-68) and then heated for 15 seconds in a microwave and placed in 37° C. water bath to form a clear solution. As DGP by itself does not foam up particularly well it was again mixed with ODM at ratio of 3:1 to increase the foaming effect.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| (20% DGP + 20% OGP)/20% F-68 (3:1:1) (375 μl) | Foamed well (70 ml) | Small bubbles on the top of scaffold and to the base | Collapsed a lot on addition of cross linking agent | Smaller bubbles but not very homogenous |

Summary of Results

Scaffolds prepared via 'SMOF #1+ DGP/ODM' were mixed in a 100 ml mixing vessel. The solution mix foamed up to 80% of the total volume of the mixing vessel. After mixing, the foam exhibited solid characteristics and was difficult to tap down to an even level. Following casting, the foam was homogenous over the depth of the scaffold. Moreover, after incubating the scaffolds for an hour at 37° C., the bubble and pore size was considerably smaller when compared to the scaffolds prepared via 'SMOF #1'.

G3—Investigation of Octyl β-D-1-Thioglucopyranoside (TGP)

TGP is a water soluble non-ionic detergent closely related to OGP and is also used for solubilisation and isolation of membrane proteins. It is stable in aqueous solution and easily removed by dialysis. TGP was used to replace OGP at a concentration of 20% wt. in $dH_2O$ and heated for five seconds in a microwave and placed in 37° C. water bath to form a clear solution.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| 20% TGP/20% F-68 (375 μl) | Foamed well (60 ml) | Small bubbles on the top of scaffold and to the base | Did not collapse much on addition of cross linking agent | Smaller bubbles but not very homogenous |

Summary of Results

Scaffolds prepared via 'SMOF #1+ TGP' were mixed in a 100 ml mixing vessel. The solution mix foamed up to 60% of the total volume of the mixing vessel. After mixing, the foam exhibited fluid characteristics and was easy to tap down to an even level following casting. There was a noticeable difference in the size of the bubble formed from the top of the foam compared to the base, as observed visually with larger bubbles were observed on top of the scaffold when compared to scaffolds prepared via 'SMOF #1'.

Figure 9:
FIG. 9. Eosin staining histological section of the optimised Smart Matrix™ formula #1 +TGP.
Figure 10:
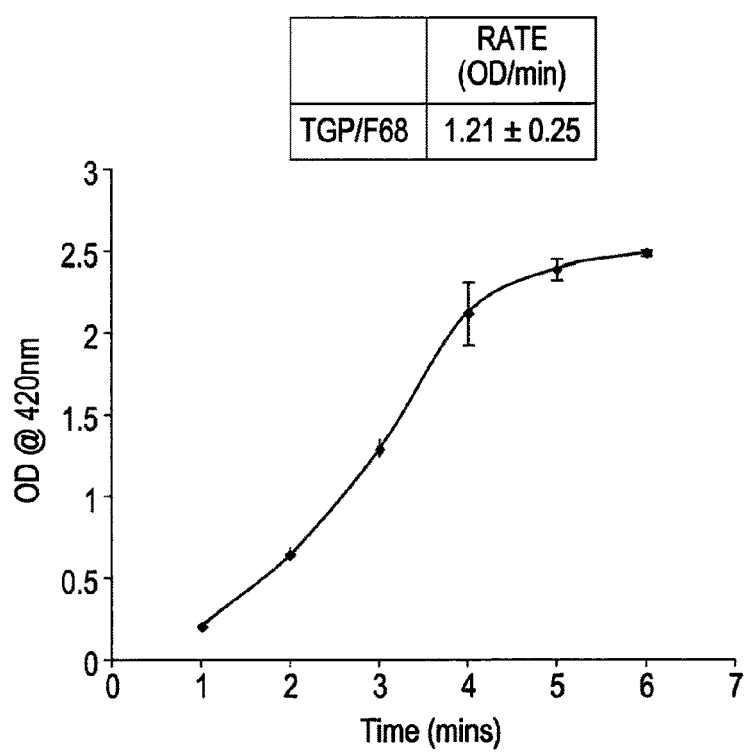
FIG. 10. Coagulation results using surfactant TGP/F-68.

FIG. 9. Eosin staining histological section of the optimised Smart Matrix™ formula #1 +TGP FIG. 10. Coagulation results using surfactant TGP/F-68.

H3—Investigation of Hexyl β-D-Glucopyranoside (HGP)

HGP is a mild ionic detergent with greater hydrophillicity than OGP. HGP was used to replace OGP at a concentration of 20% wt in $dH_2O$ and heated for five seconds in a microwave and placed in 37° C. water bath to form a clear solution.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| 20% HGP/20% F-68 (4:1) (375 µl) | Foamed well (40 ml) | Small bubbles on the top of scaffold and to the base | Did not collapse much on addition of cross linking agent | Smaller bubbles but not very homogenous |

Summary of Results

Scaffolds prepared via 'SMOF #1+ HGP' were mixed in a 100 ml mixing vessel. The solution mix foamed up to 20% of the total volume of the mixing vessel. After mixing, the foam exhibited liquid characteristics and was easy to tap down to an even level following casting. On visual analysis, there was considerable reduction in the bubble size and also there was not much noticeable difference between the top and bottom layer of the scaffold when compared to the scaffolds prepared via 'SMOF #1'.

Figure 11:
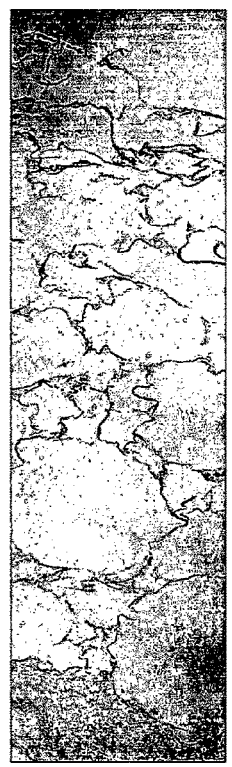
FIG. 11. Eosin staining histological section of the optimised Smart Matrix™ formula #1 +HGP.
Figure 12:
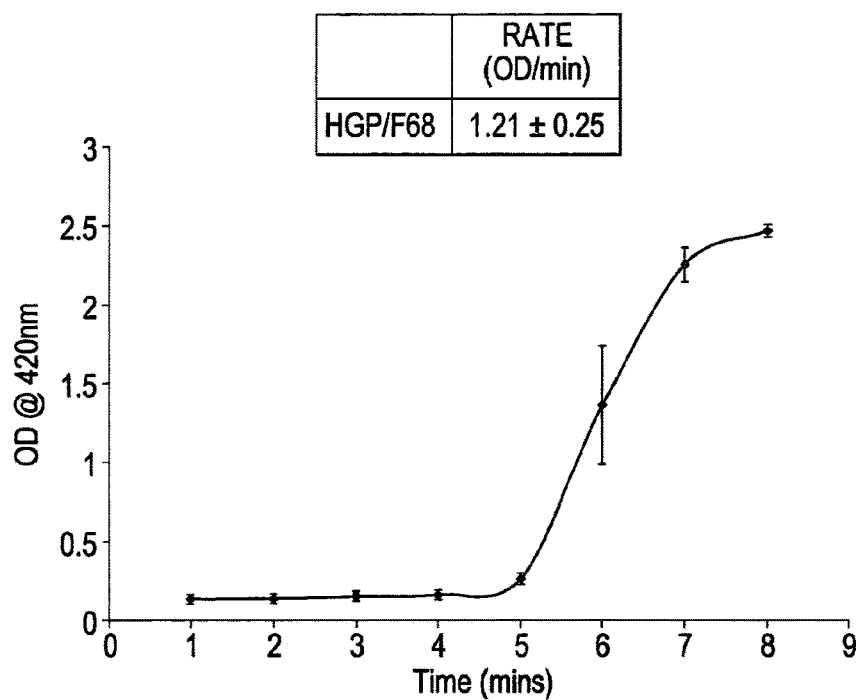
FIG. 12. Coagulation results using surfactant HGP/F-68.

FIG. 11. Eosin staining histological section of the optimised Smart Matrix™ formula #1 +HGP FIG. 12. Coagulation results using surfactant HGP/F-68. Investigation of Dodecyl β-D-Glucopyranoside (DdGp)

DdGP is known as a detergent used to dissolve integral membrane proteins in their native state. DdGP is similar to OGP but with greater lipophilicity.

I3—Investigation of Dodecyl β-D-Glucopyranoside (DdGp)+OGP

DdGP was used at a concentration of 20% wt in $dH_2O$. It was dissolved by the addition of F-68 in the ratio 4:1 (DdGP:F-68) and then heated for 15 seconds in a microwave and placed in 37° C. water bath to form a clear solution. As it was found that DdGP by itself does not foam very well it was therefore mixed with OGP at ratio of 3:1 to increase foam formation. To prevent precipitation of this surfactant it was placed in water bath throughout the experiment.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| 20% DdGP/20% OGP/20% F-68 (3:1:1) (375 µl) | Foamed well (70 ml) | Small bubbles on the top of scaffold and to the base | Collapsed a lot on addition of cross linking agent | Smaller bubbles but not very homogenous |

Summary of Results

Scaffolds prepared via 'SMOF #1+ DdGP/OGP' were mixed in a 100 ml mixing vessel. The solution mix foamed up to 80% of the total volume of the mixing vessel. After mixing, the foam exhibited solid characteristics and was difficult to tap down to an even level. Following casting, the foam was homogenous over the depth of the scaffold. Moreover, after incubating the scaffolds for an hour at 37° C., the bubble and pore size was considerably smaller when compared to the scaffolds prepared via 'SMOF #1'.

J3—Investigation of Dodecyl β-D-Glucopyranoside (DdGp)+ODM

DdGP was used at a concentration of 20% wt in $dH_2O$, dissolved by the addition of F-68 in the ratio 4:1 (DdGP:F-68) and then heated for 15 seconds in a microwave and placed in 37° C. water bath to form a clear solution. As previously explained, DdGP was mixed with ODM at ratio of 3:1 to increase foam formation. It was incubated in a 37° C. waterbath throughout the experiment to prevent precipitation of this surfactant.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| 20% DdGP + 20% ODM/20% F-68 (3:1:1) (375 µl) | Foamed well (75 ml) | Small bubbles on the top of scaffold and to the base | Collapsed a lot on addition of cross linking agent | Smaller bubbles with consistent homogeneity |

Summary of Results

Scaffolds prepared via 'SMOF #1+ DdGP/ODM' were mixed in a 100 ml mixing vessel. The solution mix foamed up to 80% of the total volume of the mixing vessel. After mixing, the foam exhibited solid characteristics and was difficult to tap down to an even level. Following casting, the foam was homogenous over the depth of the scaffold. Moreover, after incubating the scaffolds for an hour at 37° C., the bubble and pore size was considerably smaller when compared to the scaffolds prepared via 'SMOF #1'.

Investigation of Decyl β-D-Maltopyranoside (DMP)

DMP is an ionic detergent with a 12 carbon atom chain attached to two carbon rings.

K3—Investigation of Decyl β-D-Maltopyranoside (DMP)+ OGP

DMP was used at a concentration of 20% wt in dH$_2$O. It was dissolved by the addition of F-68 in the ratio 4:1 (DMP: F-68) to form a clear solution. It was found that DMP by itself does not foam very well so therefore it was mixed with OGP at ratio of 3:1 to increase foam formation.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| 20% DMP/20% OGP/20% F-68 (3:1:1) (375 µl) | Foamed well (70 ml) | Small bubbles on the top of scaffold and to the base | Collapsed a lot on addition of cross linking agent | Smaller bubbles with consistent homogeneity |

Summary of Results

Scaffolds prepared via 'SMOF #1+ DMP/OGP' were mixed in a 100 ml mixing vessel. The solution mix foamed up to 75% of the total volume of the mixing vessel. After mixing, the foam exhibited fluid characteristics and was easy to tap down to an even level. Following casting, the foam was homogenous over the depth of the scaffold. Moreover, after incubating the scaffolds for an hour at 37° C., the bubble and pore size was considerably smaller when compared to the scaffolds prepared via 'SMOF #1'.

L3—Investigation of Decyl β-D-Maltopyranoside (DMP)+ ODM

DMP was used at a concentration of 20% wt in dH$_2$O. It was dissolved by the addition of F-68 in the ratio 4:1 (DMP: F-68) to form a clear solution. As DMP by itself does not form as much foam as OGP it was therefore mixed with ODM at ratio of 3:1 to increase the foaming effect.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| 20% DMP/20% ODM/20% F-68 (3:1:1) (375 µl) | Foamed well (75 ml) | Small bubbles on the top of scaffold and to the base | Collapsed a lot on addition of cross linking agent | Smaller bubbles with consistent homogeneity |

Summary of Results

Scaffolds prepared via 'SMOF #1+ DMP/ODM' were mixed in a 100 ml mixing vessel. The solution mix foamed up to 75% of the total volume of the mixing vessel. After mixing, the foam exhibited fluid characteristics and was easy to tap down to an even level. Following casting, the foam was homogenous over the depth of the scaffold. Moreover, after incubating the scaffolds for an hour at 37° C., the bubble and pore size was considerably smaller when compared to the scaffolds prepared via 'SMOF #1'.

Figure 13:
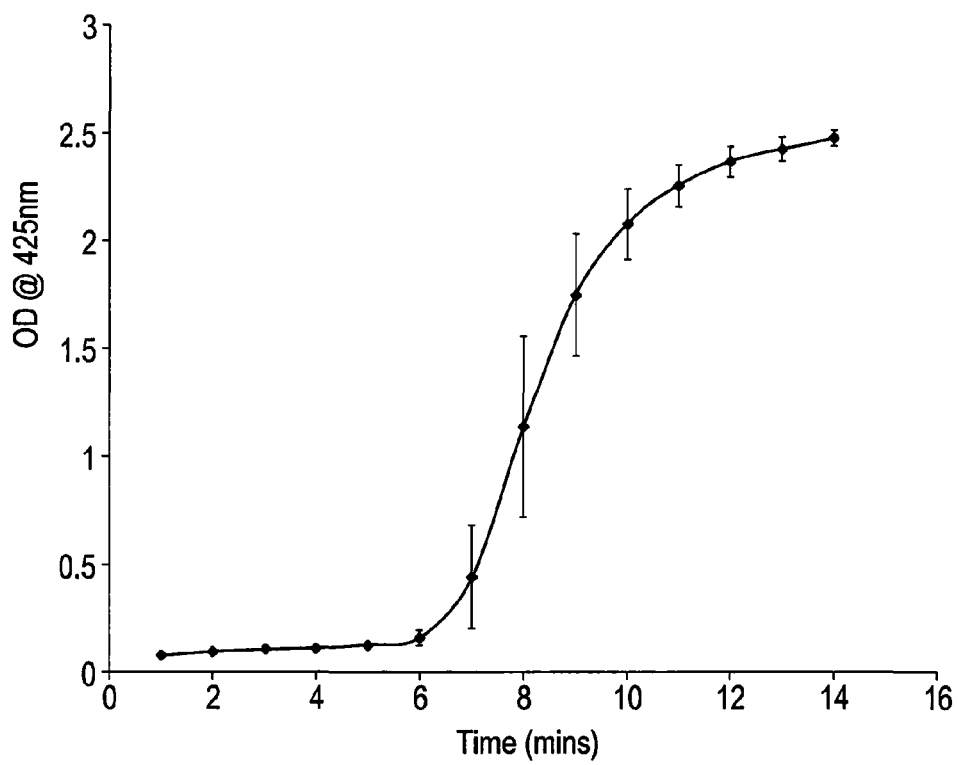
FIG. 13. Coagulation results using surfactant DMP/ODM/F-68.

FIG. 13. Coagulation results using surfactant DMP/ODM/F-68.

M3—Investigation of Decyl β-D-Maltopyranoside (DMP)+ DdGP+ODM

DMP, DdGP and ODM were used at a concentration of 20% wt in dH$_2$O. Each surfactant was dissolved by the addition of F-68 in the ratio 4:1 (DMP: F-68) to form a clear solution. DMP/F-68 by itself does not foam up very well and therefore it was mixed with DdGP/F-68 at ratio of 2:1 to increase the foaming effect. ODM/F-68 was mixed in this solution (DMP/F68+DdGP/F-68) at a ratio of 1:3.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| 20% DMP/20% DdGP/20% ODM/20% F-68 (2:2:1:1) (375 µl)DdGP | Foamed well (90 ml) | Small bubbles on the top of scaffold and to the base | Did not collapse much on addition of cross linking agent | Smaller bubbles with consistent homogeneity |

Summary of Results

Scaffolds prepared via 'SMOF #1+ DMP/ODM' were mixed in a 100 ml mixing vessel. The solution mix foamed up to 90% of the total volume of the mixing vessel. After mixing, the foam exhibited fluid characteristics and was easy to tap down to an even level. Following casting, the foam was homogenous over the depth of the scaffold. Moreover, after incubating the scaffolds for an hour at 37° C., the bubble and pore size was considerably smaller when compared to the scaffolds prepared via 'SMOF #1'.

Figure 14:
FIG. 14. Eosin staining histological section of the optimised Smart Matrix™ formula #1 +(DMP+DdGP): ODM.
Figure 15:
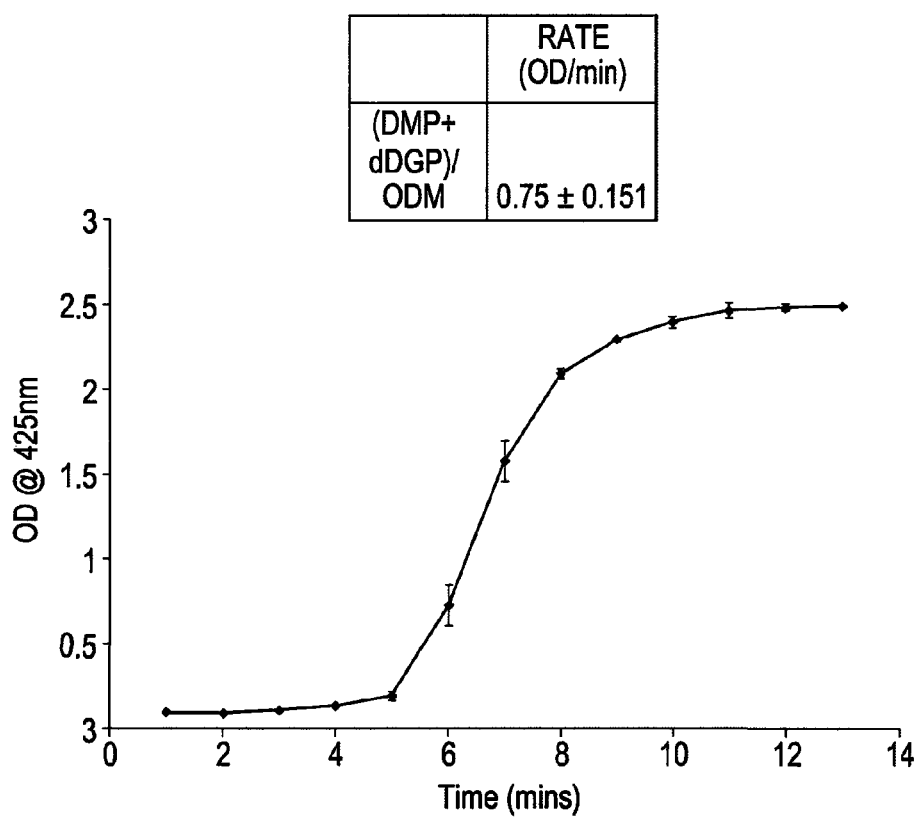
FIG. 15. Coagulation results using surfactant (DMP+DdGP)/ODM.

FIG. 14. Eosin staining histological section of the optimised Smart Matrix™ formula #1 +(DMP+DdGP): ODM FIG. 15. Coagulation results using surfactant (DMP+DdGP)/ODM.

N3—Investigation of Decyl β-D-Maltopyranoside (DMP)+DdGP+OGP

DMP, DdGP and OGP were used at a concentration of 20% wt in $dH_2O$. Each surfactant was dissolved by the addition of F-68 in the ratio 4:1 (DMP: F-68) to form a clear solution. DMP/F-68 by itself does not foam up very well and therefore it was mixed with DdGP/F-68 at ratio of 2:1 to increase the foaming effect. OGP/F-68 was mixed in this solution (DMP/F68+DdGP/F-68) at a ratio of 1:3.

| SURFACTANT | FOAM ON CAST | FOAM AFTER 1 hr COAGULATION | SCAFFOLD ON X-LINKING | SCAFFOLD AFTER X-LINKING |
|---|---|---|---|---|
| 20% DMP/20% DdGP/20% OGP/ 20% F-68 (2:1:1:1) (375 µl) | Foamed well (90 ml) | Small bubbles on the top of scaffold and to the base | Did not collapse much on addition of cross linking agent | Smaller bubbles with consistent homogeneity |

Summary of Results

Scaffolds prepared via 'SMOF #1+ DMP/OGP' were mixed in a 100 ml mixing vessel. The solution mix foamed up to 90% of the total volume of the mixing vessel. After mixing, the foam exhibited fluid characteristics and was easy to tap down to an even level. Following casting, the foam was homogenous over the depth of the scaffold.

Moreover, after incubating the scaffolds for an hour at 37° C., the bubble and pore size was considerably smaller when compared to the scaffolds prepared via 'SMOF #1'.

Figure 16:
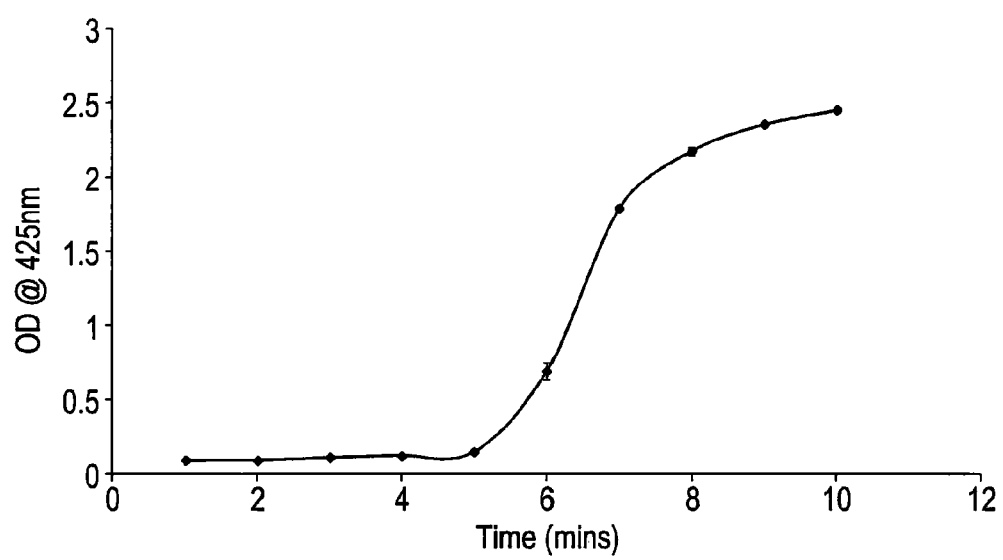
FIG. 16. Coagulation results using surfactant (DMP+DdGP)/OGP.

FIG. 16. Coagulation results using surfactant (DMP+DdGP)/OGP.

| Table summarising surfactant concentration ranges in preceding scaffold formulation | | |
|---|---|---|
| Exp Code | Surfactant (abbreviations as table, p27) [all surfactants made to 20% wt/vol H2O except Spans] | Final Concentration (% wt/vol) in formulation mixture [F-68 range in all mixes is 0.19-0.37] [Total Surfactants range = 0.97-1.84] |
| A3 | OGP [in 20% OGP/20% F-68 (4:1)] | OGP: 077-1.48 |
| B3 | Spans (20, 40, 60, 80) 0.01-1% [in 20% OGP/20% F-68 (4:1) | Span: 0.009-0.09, OGP: 1.48 |
| C3 | ODM [in 20% ODM/20% F-68(4:1)] | ODM: 0.77-1.48 |
| D3 | DGP [in 20% DGP/20% F-68 (4:1)] | DGP: 0.77-1.48 |
| E3 | DGP + OGP [in 20% DGP/20% OGP/20% F-68 (1:1:1, 2:1:1. 3:1:1)] | DGP: 0.32-1.1, OGP: 0.19-0.6 |
| F3 | DGP + ODM [in 20% DGP/20% ODM/20% F-68 (1:1:1, 2:1:1, 3:1:1)] | DGP: 0.32-1.1, ODM: 0.19-0.6 |
| G3 | TGP [in 20% TGP/20% F-68 (4:1)] | TGP: 0.77-1.48 |
| H3 | HGP [in 20% HGP/20% F-68 (4:1)] | HGP: 0.77-1.48 |
| I3 | DdGP + OGP [in 20% DdGP/20% OGP/20% F-68 (1:1:1, 2:1:1, 3:1:1)] | DdGP: 0.32-1.1, OGP: 0.19-0.6 |
| J3 | DdGP + ODM [in 20% DdGP/20% ODM/20% F-68 (1:1:1, 2:1:1, 3:1:1)] | DdGP: 0.32-1.1, ODM: 0.19-0.6 |
| K3 | DMP + OGP [in 20% DMP/20% OGP/20% F-68 (1:1:1, 2:1:1, 3:1:1)] | DMP: 0.6-1.1, OGP: 0.37-0.6 |

Table summarising surfactant concentration ranges in preceding scaffold formulation

| Exp Code | Surfactant (abbreviations as table, p27) [all surfactants made to 20% wt/vol H2O except Spans] | Final Concentration (% wt/vol) in formulation mixture [F-68 range in all mixes is 0.19-0.37] [Total Surfactants range = 0.97-1.84] |
|---|---|---|
| L3 | DMP + ODM [in 20% DMP/20% ODM/20% F-68 (1:1:1, 2:1:1, 3:1:1)] | DGP: 0.32-1.1, ODM: 0.19-0.6 |
| M3 | DMP + DdGP + ODM [in 20% DMP/20% DdGP/20% ODM/20% F-68 (2:1:1:!)] | DMP: 0.39-0.74, DdGP: 0.19-0.37, ODM: 0.19-0.37 |
| N3 | DMP + DdGPP + OGP [in 20% DMP/20% DdGP/20% ODM/20% F-68 (2:1:1:1)] | DMP: 0.39-0.74, DdGP: 0.19-0.37, OGP: 0.19-0.37 |

Table showing coagulation results of all surfactants used during the experiment.
COAGULATION DATA FOR SUGAR SURFACTANTS IN THE ABOVE MANUFACTURE MIXTURES

| # | SURFACTANTS | RATE (OD/min) | STD DEV | ONSET (min) | GEL % |
|---|---|---|---|---|---|
| 1 | (DMP + DdGP)ODM | 0.7535 ± 0.151122 | 0.151122 | 5 | 100 |
| 2 | 1/2 OGP/F68 | 0.540666667 ± 0.060857 | 0.060857 | 5 | 90 |
| 3 | (DMP + DdGP)OGP | 0.54 ± 0.038691 | 0.038691 | 5 | 100 |
| 4 | ODM/F-68 | 0.604666667 ± 0.062164 | 0.062164 | 9 | 80 |
| 5 | DMP/F-68 | 0.62833333 ± 0.153207 | 0.153207 | 5 | 80 |
| 6 | HGP/F-68 | 1.098333333 ± 0.353228 | 0.353228 | 5 | 90 |
| 7 | TGP/F-68 | 1.215333333 ± 0.250388 | 0.250388 | 1 | 90 |
| 8 | DMP + ODM | 0.742 ± 0.118899 | 0.118899 | 6 | 90 |

Additional Matrix/Scaffold Development Experiments:

The main variables which have been tested are in the list below.

Calcium
  2-50 mM in the mix (prepared from 1M stock solution)
Thrombin
  1.5-12 U/120 mg Fbg [6 ml 2% Fbg=120 mg]
Fibrinogen
  2% solution, diluted to approx 1% in final mixture.
Alginate
  (dissolved and neutralised with NaOH, pH 7.4)
  Sigma alginic acid AA,
  Sigma sodium alginate,
  ISP LKX,
  ISP DMB,
  ISP LB (Manucol LB)
  ISP KC (Kelcolloid propylglycol alginate), (K3B426)
  ISP AA (alginic acid H/LDB)
  NovaMatrix High M—NM MVLMW (UP VLVM)
  NovaMatrix High G—NM GVLMW (UP VLVG)
  Made to 2%, used at ratios with fibrinogen approx 0.125:1 to 2:1 (0.1-1.5%)
Stabilisers
  Glycerol 5%
  Trehalose 10-11% in the mix before thrombin addition, and 4-7.5% after thrombin/alginate/surfactant addition. (Prepared from a saturated stock solution at about 60-66% wt.)
Surfactants
  Pluronic L101, L85, F68, F127
  OGP (Octyl-βD glucopyranoside)
  OTP (octyl thioglucopyranoside)
  DGP (decyl-βD-glucopyranoside)
  DdGP (dodecyl-βD-glucopyranoside)
  ODM (Octyl-βD maltoside)
  DMP (decyl-βD-maltopyranoside)

Mostly within 0.1-1% final mixture concentration, with F68 & F127 tested at 0.1 to 5%

Methodology
  Scaffold Manufacture
  Analysis
(I) Structure
  a) by LM: wax-embedding, histological sectioning and eosin staining.
  b) SEM: re-hydration of sample in diH$_2$O (sorbitol removal), lyophilisation, carbon splutter coating, SEM examination.
(II) Cell adhesion/biocompatibility
(III) Integration in porcine full thickness wound model
Structural Characterisation of Matrices:

The physical structure of trial scaffolds was evaluated using 3 visually assessed features:
  1. Macro-scale homogeneity.
  2. Pore structure.
  3. Fine structure especially around pore lamellae.

Figure 17:
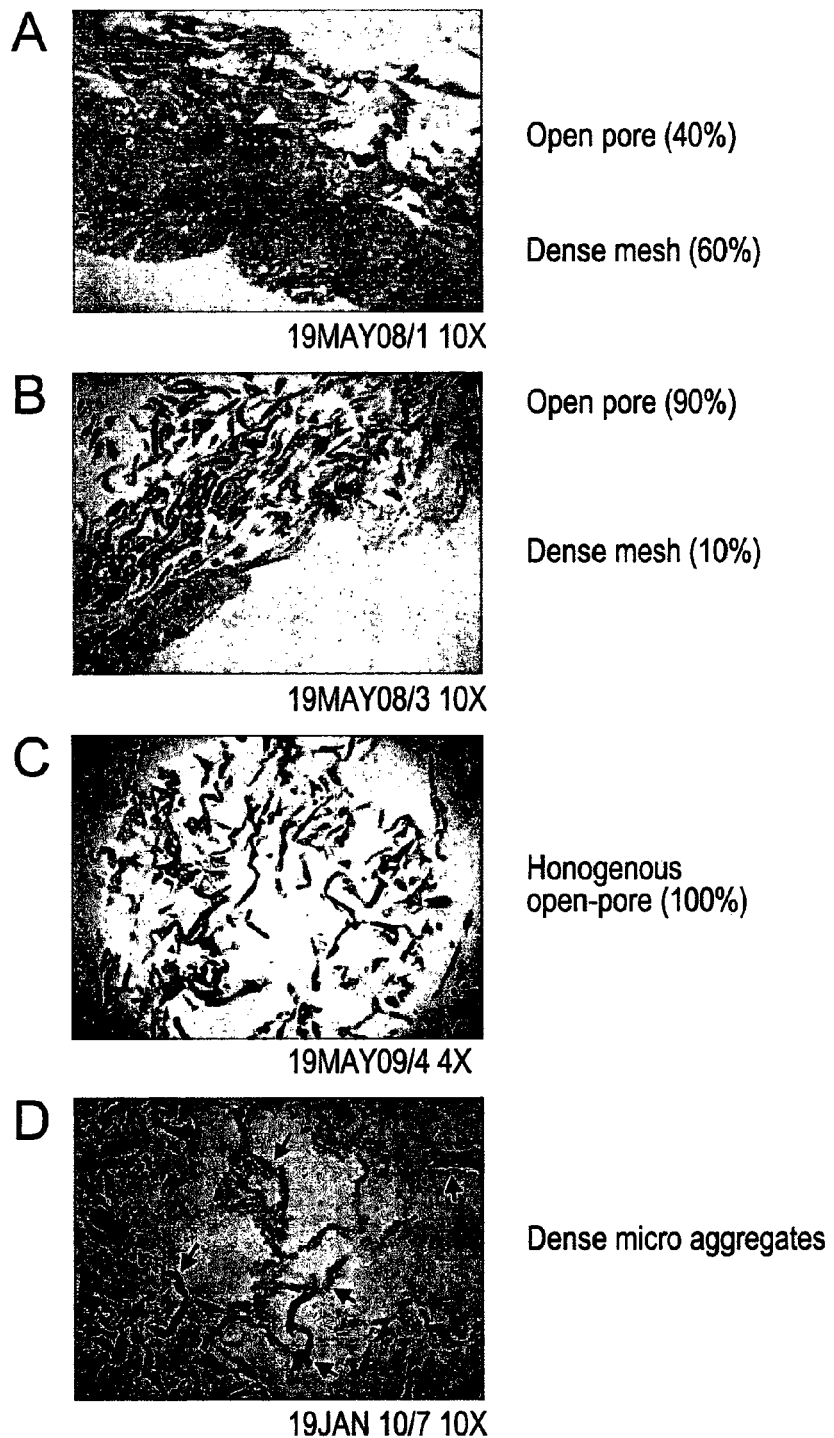
FIG. 17. Physical Structure of Trial Scaffolds.
Figure 18A:
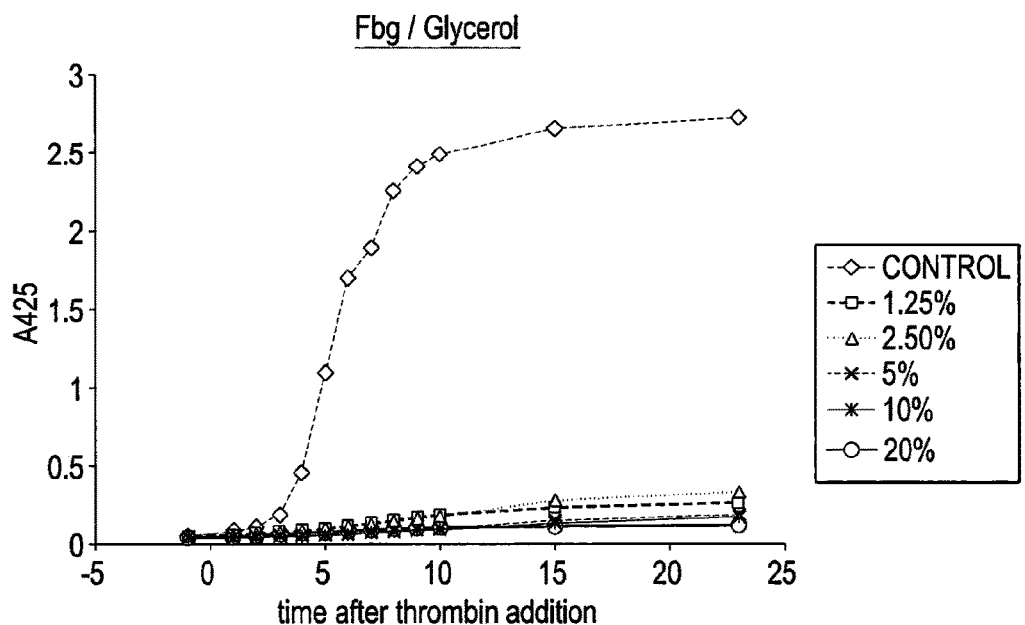
FIGS. 18-20. Further Coagulation Results.
Figure 18B:
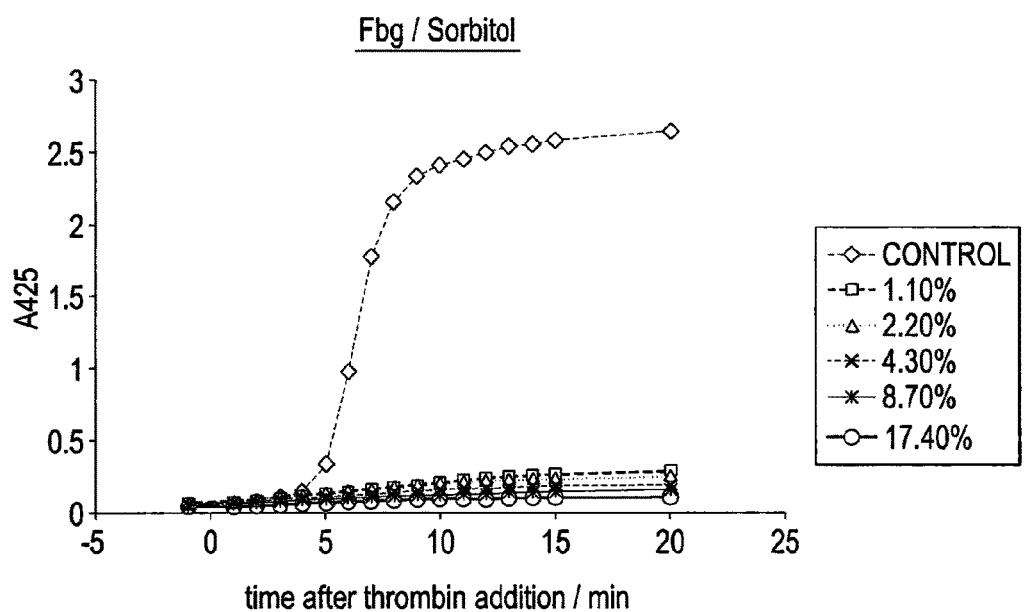
Figure 18C:
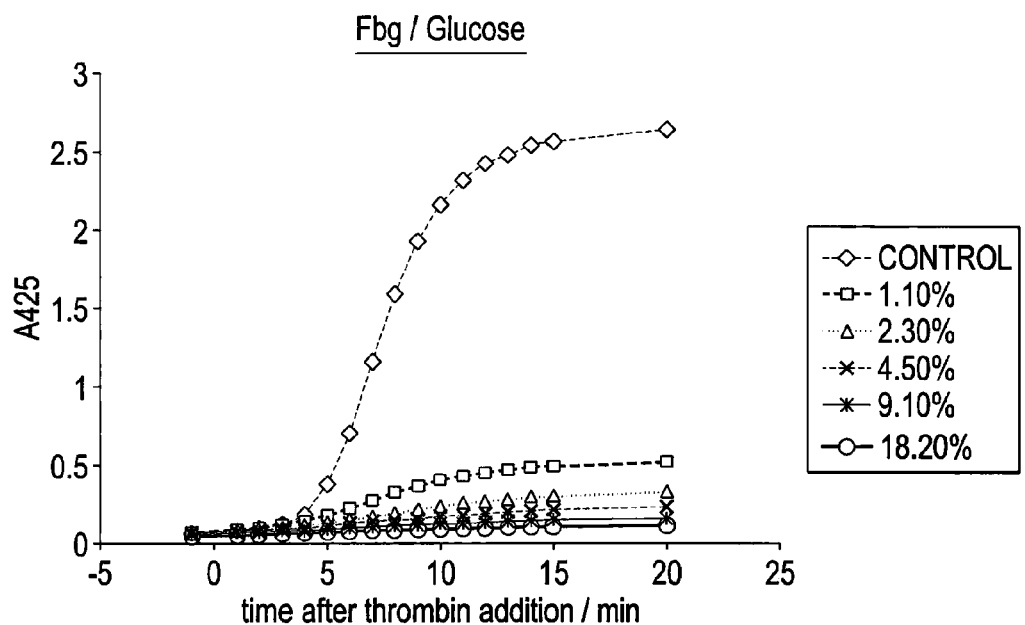
Figure 18D:
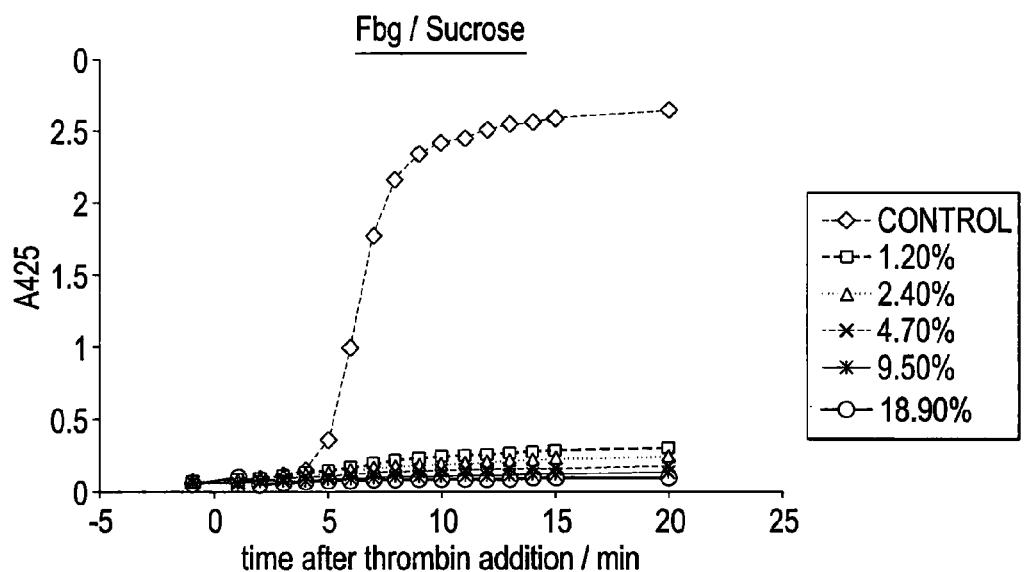
Figure 18E:
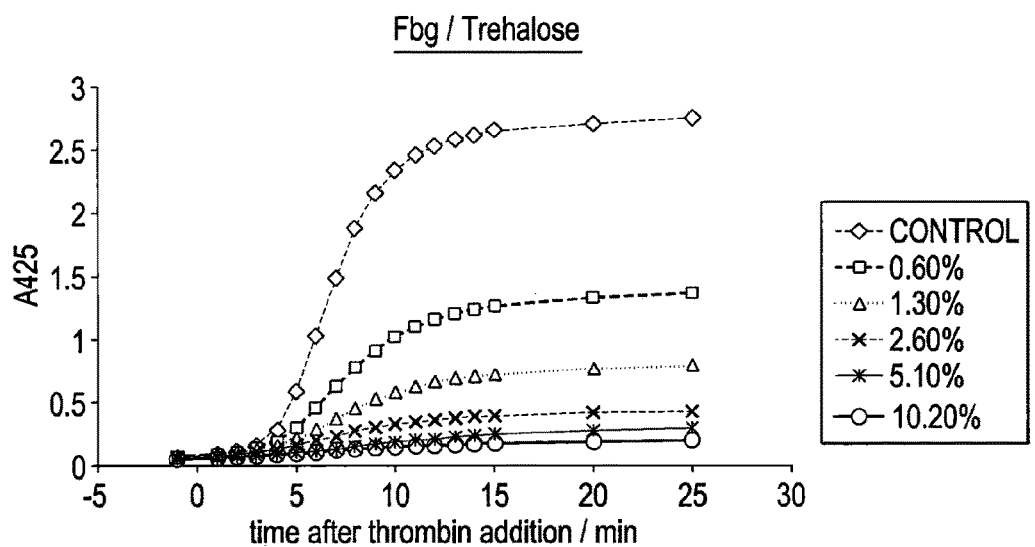
Figure 18F:
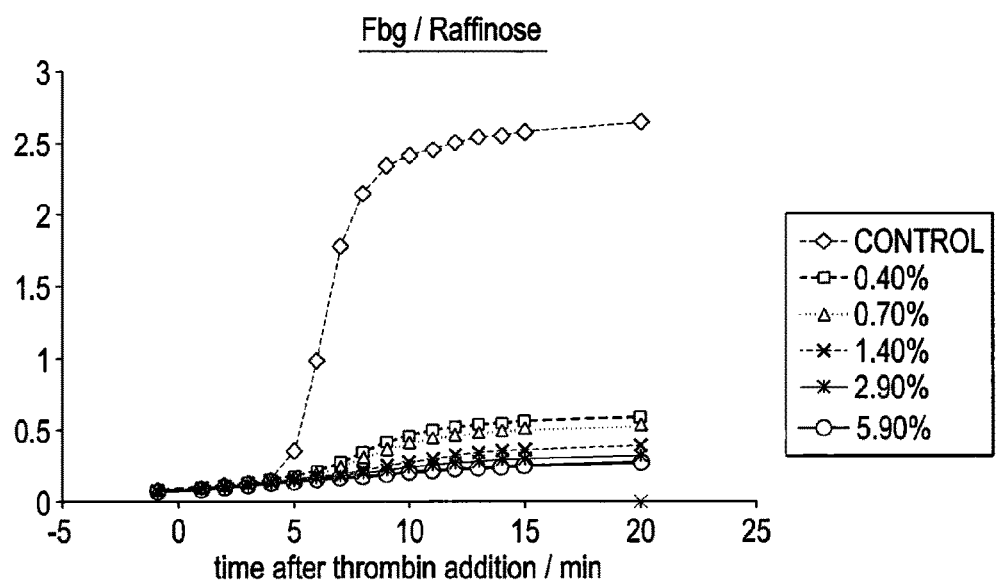
Figure 19A:
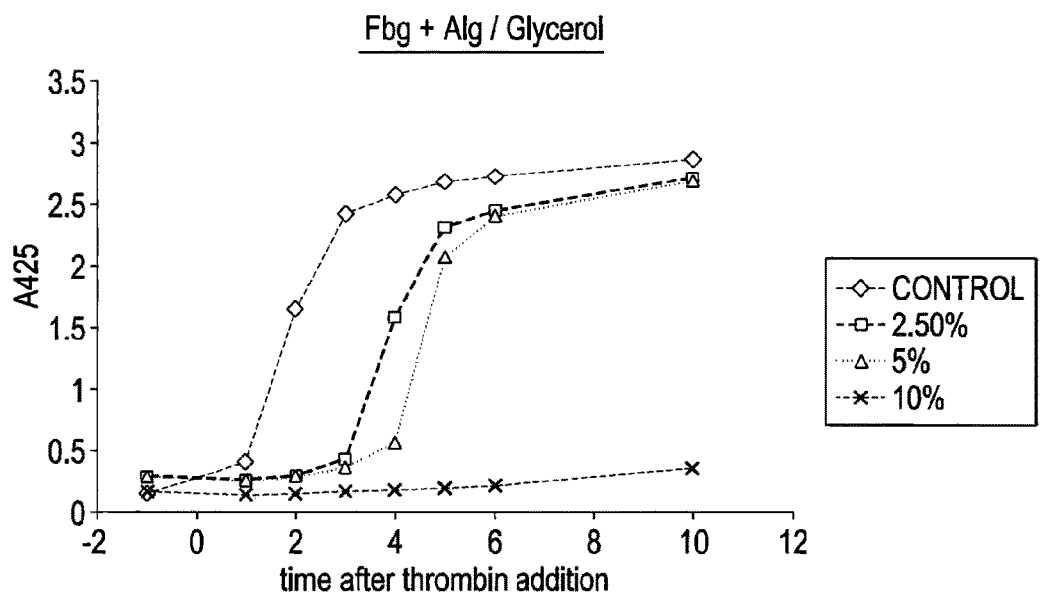
Figure 19B:
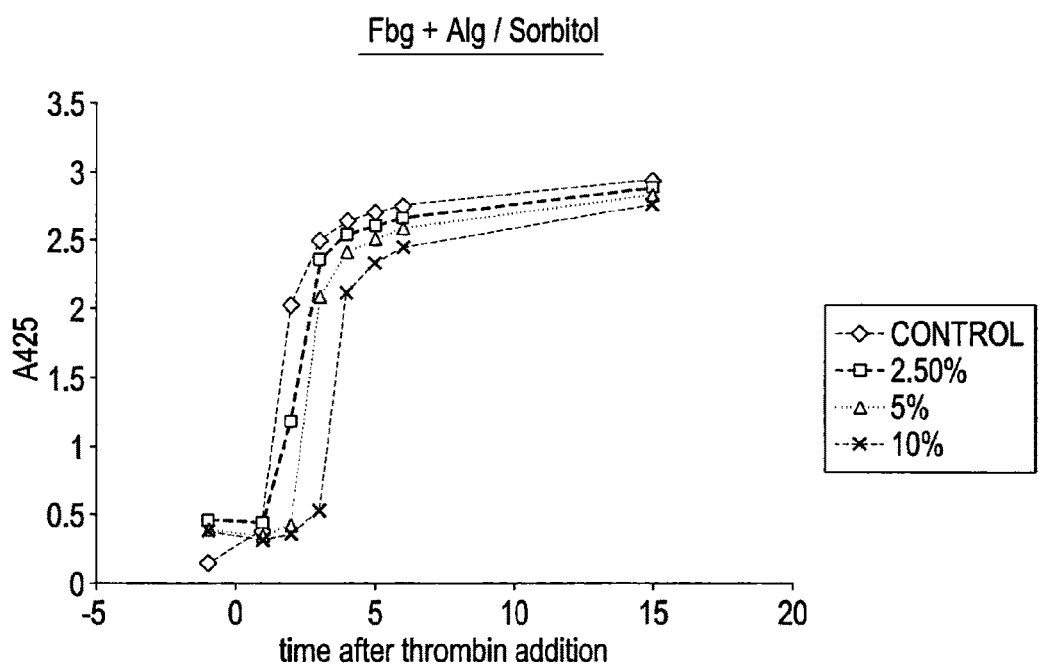
Figure 19C:
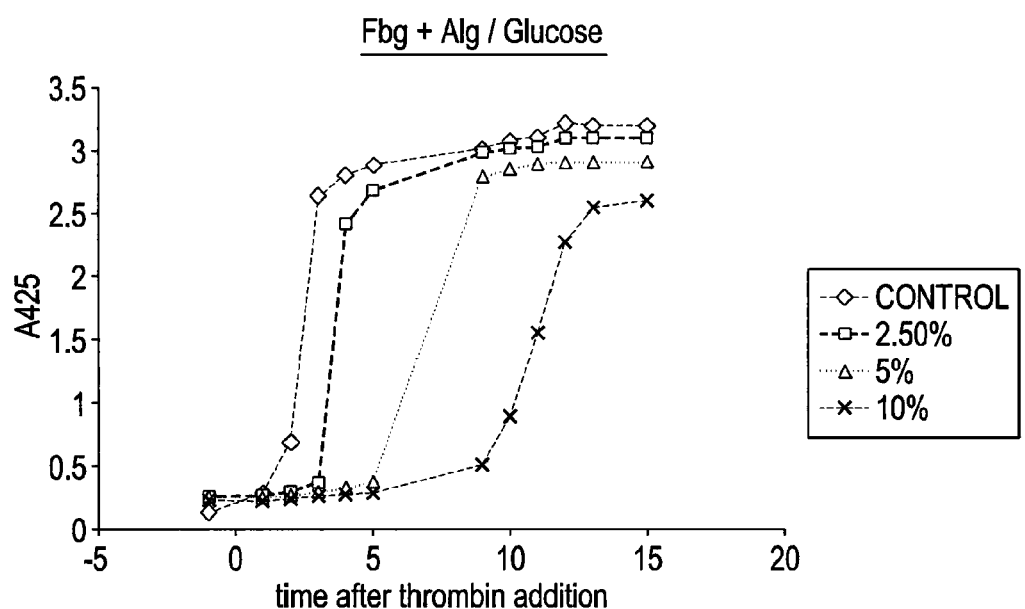
Figure 19D:
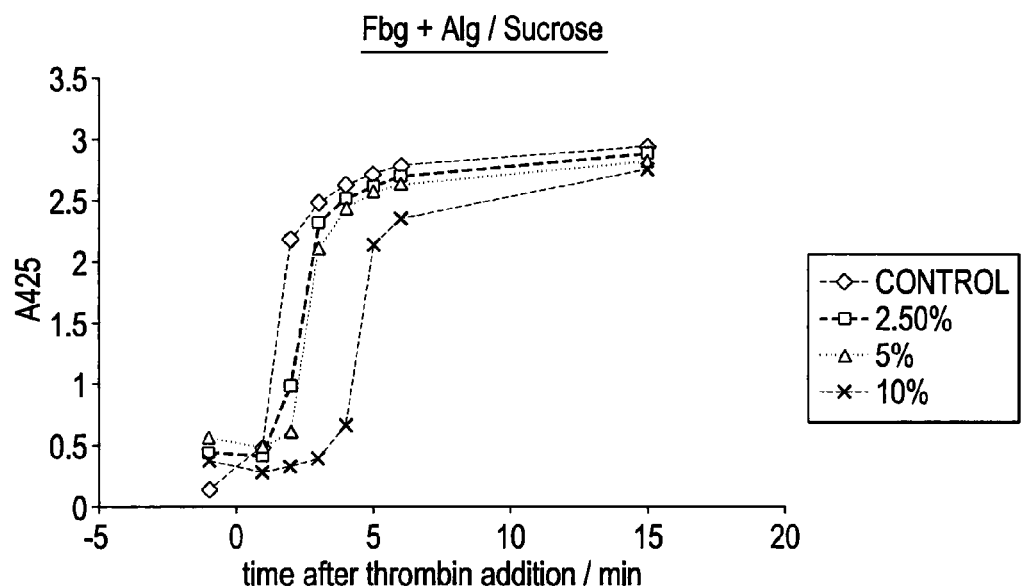
Figure 19E:
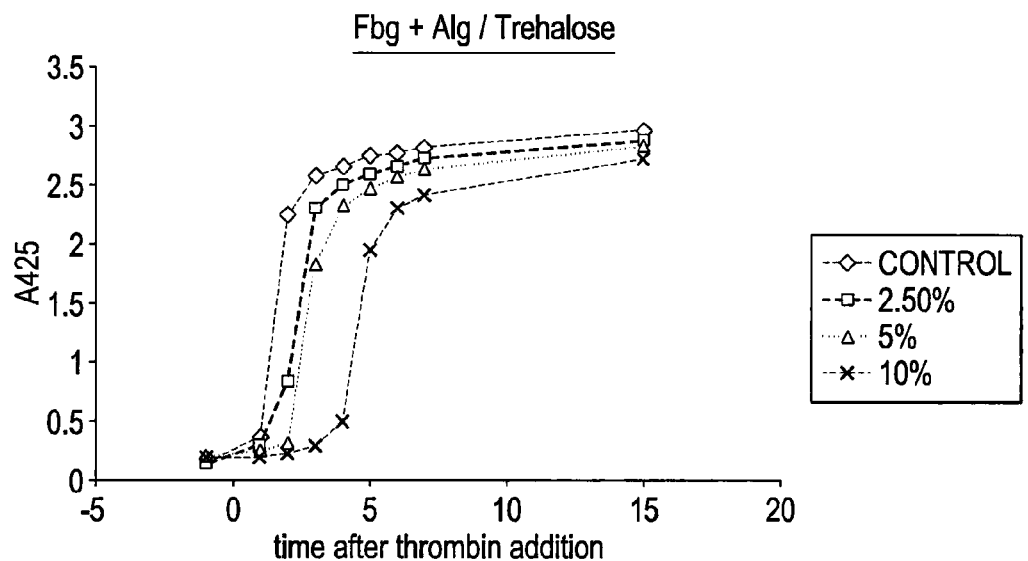
Figure 19F:
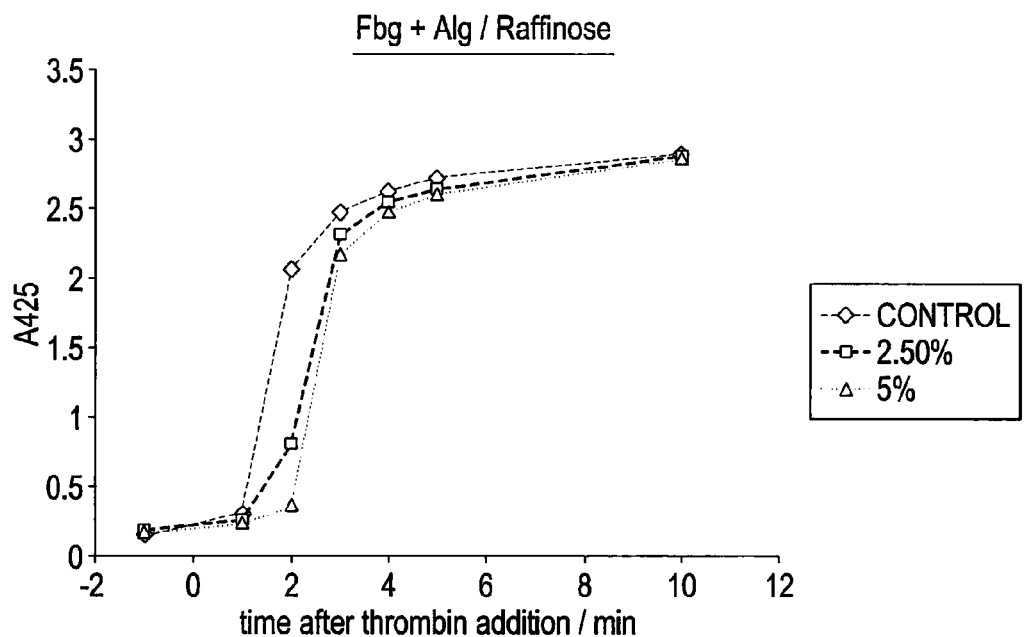

FIG. 17 A shows a typical non-homogenous macro-scale bi-layer structure in a vertical section through a prototype scaffold. The lower portion is described as 'dense mesh' structure; the upper as 'open pore structure'. The dense mesh structure is formed due to partial collapse of the foam coagulum after casting. Another structure formed from collapse of a foam is are dense lamellae. An important aim is to identify conditions which allow a homogeneous open pore structure to be produced without wastage, and without dense mesh or lamellae formation.

17 B shows substantial open pore homogeneity and an intermediate open pore structure, due the compact pellicular appearance of this phase.

17 C shows an entirely homogeneous open-pore structure. This shows regular open-pore lamellae of an intended optimal scaffold, in comparison to B, but some large bubble spaces and also dense spots with the lamellae structure.

17 D shows a close to optimal open pore structure but with dense micro-aggregates.

| Batch | Formulation unless stated: $Ca^{2+}$ = 2 mM Fbg & Alginate = 2% Thrombin = 10 U/ml Surfactant = 20% | Variable | Result |
|---|---|---|---|
| A4 | hFbg 6 ml Thrombin 150 μl Sigma AA 6 ml | | |
| B4 1-9 | hFbg 6 ml Thrombin 1X 150 μl Sigma AA 6 ml | AA Sigma/ISP Thrombin, 1x/4x mixer speed 2000/6000 rpm ± sorbital Ca 2 mM/5 mM | 2000 rpm gave very dense structure 6000 rpm gave open porous structure Dense and open pore mesh layers resulted sorbitol use seen to increase resultant porosity of dense structure region (avoiding collapse) high Thrombin slightly denser lamellae little effect of high Ca Sigma & ISP AA similar |
| C4 | Fbg Thrombin 1X Sorbitol for lyophilisation | Pluronic (0-5%) ± Heparin | Pluronic 127 addition increased the proportion of open porous structure - although this was formed from densely aggregated material in individual lamellae. Addition of heparin also increased density of lamellae |
| D4 1-10 | Fbg 6 ml Sigma AA 6 ml | Thrombin 1X, 4X or 8X (1.5-12 U) No pluronic controls Pluronic F127 1.4% or 4.65% | Increased Thrombin without surfactant increases the density of the resulting material, creating a structure with few millimeter scale pores and very thick lamellae - very unsuitable ECM. Introduction of 1.4% pluronic F127 surfactant at 12 U Thrombin creates a homogenous open pore structure - much better than previous, but lamellae similarly dense as seen in previous batch. Further increase of F68 to 4.5% creates a pellicular foam structure - elliptical beads of fibrin thinly connected along foam lamellae. High open porosity but fairly compact fibrin, unsuitable for ECM. |
| E4 1-28 1-16 Sigma AA 17-20 ISP AA 21-28 ISP KC | Fbg 6 ml | Thrombin 1X, 4X or 8X (1.5-12 U) Pluronic F127 0, 0.1, 0.37, 0.73, 1.4% Sigma AA 0.25-1% ISP AA 1% ISP KC 0.25-1% | Less than 1.4% F127 and less than 12 U Thrombin is insufficient to form an approximately homogenous porous structure. Reducing alginate proportion from 50 to 12% slightly increases the density and ribbon-like structure of lamellae, an effect increased by increasing Thrombin from 1.5 to 12. Open pore structures are formed with 1.4% F127 similarly with 12%, 15% or 50% alginate. ISP AA results in similar fine structure as Sigma AA, but ISP KC (propylglycol alginate) gives truncated non-fibrillar fibrin, although slightly less abnormal with 12 U than 1.5 U Thrombin. |
| F4 | Fbg 6 ml Alginate 1% | Thrombin 1X/8X (1.5/12 U) ± Pluronic127 0.8% ISP LBA ISP LB ISP LF ISP KC | 1X gives more heterogeneity than 8X Thrombin. LBA gives structure similar to Sigma AA. LF & KC give truncated fibrin at low Thrombin. No major structural differences between these alginates, slightly more continuous lamellae LF and KC > LB > LBA ie LBA looks most cell-conductive. Increased porosities with 12 U Thrombin compared to 1.5 U and 0.8% F127 compared to none. However, no formulae gave completely homogenous open pore structures. |
| G4 1-18 | hFbg 6 ml Thrombin 8X (12 U) Alginate 1% (6 ml) | Sigma AA ISP KC ISP LB ISP LF ISP LBA | Porcine study Several alginates gave inflammatory responses, especially KC |
| H4 1-15 | | Mixing times 30-150 sec premix Thrombin | |

| Batch | Formulation unless stated:<br>Ca$^{2+}$ = 2 mM<br>Fbg & Alginate = 2%<br>Thrombin = 10 U/ml<br>Surfactant = 20% | Variable | Result |
|---|---|---|---|
| I4<br>1-13 | bFbg 6 ml | AA sigma or ISP LBA<br>Thrombin 1X-8X (1.5-12 U)<br>Sigma AA 1% or 0.6%<br>"No Heparin controls"<br>Heparin 0.07-0.8% | Definite correlation between 1.5 U Thrombin and low porosity vs 12 U Thrombin and high porosity. 1.5 U Thrombin gives dense mesh structure, 4 U more bulky dense mesh, 12 U gives mainly 'foamy' layered open pore.<br>Definite correlation between amount of heparin added and resultant wt of product with low Thrombin, but counteracted with high Thrombin such that the mass yield is greater with more heparin. Heparin addition slightly increases the open pore formation, but similar lamellar type as without. |
| J4<br>1-10 | bFbg 6 ml<br>Thrombin 8X (12 U)<br>Sigma AA 6 ml | ±Heparin (100 μl 10%) | Mass yield marginally lower but porosity higher with heparin |
| K4<br>1-16 | bFbg 6 ml<br>Thrombin 10X (12 U)<br>HEPES/NaCl diluent | no AA control<br>Sigma AA 0.15-1% (1-6 ml) | |
| L4<br>1-6 | bFbg 6 ml<br>Thrombin 1X (150 μl) | ISP AA 0.5-1% (3-6 ml)<br>CaCl2, 2, 12.5, 25 mM (high Ca followed by citrate post X-link wash | To evaluate ISP AA on structure<br>Also to evaluate high calcium plus chelate buffer wash post cross-link<br>Post cross-link citrate wash did not cause major effect on scaffold structure - so might be an alternative processing step. |
| M4 | Fbg 6 ml<br>Thrombin 1X (150 μl)<br>Sigma 6 ml | Pluronic L101, F77 (0.16-1.5%) | L101 has potent antifoam effect |
| N4 | bFbg 6 ml<br>Thrombin 1X (150 μl)<br>ISP AA 6 ml | control<br>Pluronic F68, P85, L121 (0.16 or 1.5%) | L121 has potent antifoam effect |
| O4<br>1-17 | hFbg 6 ml<br>Thrombin 1X (150 μl)<br>Sigma 6 ml | Sigma AA<br>ISPAA<br>ISP LBA<br>Pluronic L101<br>Pluronic F127 | L101 has potent antifoam effect creating a dense mesh SM.<br>F127 has a foaming effect, creates porous scaffold, but this formulation has a biphasic structure.<br>Each alginate forms macroscopically acceptable scaffold, but LKB provokes more in-vivo inflammation than Sigma AA or ISPAA<br>(Porcine experiments 9&10) |
| P4<br>1-18 | Fbg 6 ml<br>Thrombin 1X (150 μl)<br>Alginate 6 ml | Pluronic L101 (antifoam) 0.016%<br>Pluronic F127 (foam) 1.5%<br>Separately or together<br>ISPAA (±charcoal extraction), LBA or Sigma AA | L101 markedly reducing the foaming of F127. The resultant structure with just L101 is homogenous dense mesh, with combination with 127, dense mesh with some larger pores. |
| Q4<br>1-10 | Fbg 6 ml<br>Thrombin 1X (150 μl)<br>Sigma AA 6 ml<br>Pluronic F127 1.5% | Effect of L101 pre-mixed with AA at 0.015%:2% | Antifoam effect transferred to mixture |
| R4<br>1-8 | Fbg 6 ml<br>Alginate 6 ml<br>Thrombin 1X (150 μl)<br>Pluronic 1.5% | Sigma AA, ISP AA or autoclaved ISP AA<br>Pluronic F127 or F68 | SM structure similar with each alginate. |
| S4<br>1-18 | Fbg 3 ml<br>Ca2+ 1 mM<br>Thrombin 1X | ISPAA 12.5-50%<br>Pluronic F68 0.8-4% | Scaffolds failed to clot - 1 mM too little. |
| T4<br>U4<br>1-19 | Fbg 3 ml<br>Thrombin 1X 3X 4X (1.5, 3, 4.5 U) | Pluronic F68 0.4-2.7%<br>ISP AA - or ISPAA autoclaved | 1.5% F68 gives homogenous porosity, but less gives dense mesh and open mesh zones, but micro-aggregates present.<br>Decreasing Alginate and increasing F68 does |

-continued

| Batch | Formulation unless stated:<br>Ca$^{2+}$ = 2 mM<br>Fbg & Alginate = 2%<br>Thrombin = 10 U/ml<br>Surfactant = 20% | Variable | Result |
|---|---|---|---|
| | | 20% Viastarch instead of alginate | not prevent micro-aggregates. However with >1.5% F68, decreasing alginate from 1 to 0.3% does decrease micro-aggregate density. Substitution of Viastarch for alginate resulted in formation of large granular micro-aggregates. Use of Viastarch as alternative to AA either as 50:50 mixture with, or 100% substitution for alginate. |
| V4 1-13 | hFbg 3 ml<br>ISPAA 3 ml<br>Thrombin 3 U/3 ml Fbg | Pluronic F68 0.4 to 3.9.%<br>ISPAA 0, 12.5, 25 50% | Increasing pluronic increases the depth of open pore layer, until nearly homogeneous at 1.5 but increases formation of micro-aggregates. Thrombin controls the extent to which a dense mesh layer forms, although this is not entirely consistent. This points to the primary importance of surfactant to determine pore structure. |
| W4 1-15 | hFbg 6 ml<br>Thrombin 5X (7.5 U) | ISP AA 6 ml or 1.5 ml<br>Pluronic F68 1.4 or 2.7%<br>Thrombin 3x | |
| X4 1-6 | bFbg 6 ml<br>ISP AA 6 ml<br>Thrombin 4X<br>pluronic F68 1.47% | no variables | |
| Y4 1-15 | Fbg 3 ml<br>ISP AA 3 ml | Thrombin 5X or 10X<br>NaCl 150 or 400 mM<br>Ca$^{2+}$ 2 or 5 mM<br>pluronic F68 1.45 or 2.7% | Combination experiment<br>Elevated NaCl to increase protein solubility |
| Z4 1-20 | hFbg 6 ml<br>ISP AA 6 ml<br>Thrombin 10x<br>pluronic F68 0.7% | Ca$^{2+}$ 2-12.5 mM<br>5x5 or 10x10 sheets | Porcine test scaffolds<br>Inflammation increased with Ca$^{2+}$ > 2 mM |
| AA4 1-8 | Fbg 3 ml<br>ISP AA 3 ml<br>pluronic F68 0.77% | NaCl 75 or 150 mM<br>Thrombin 1X-5X | Effect of reduced NaCl (possible increase in coagulation rate) |
| AB4 1-10 | Fbg 3 ml<br>ISP AA 3 ml (4.5 ml for No10) | Thrombin 1X-5X<br>pluronic F68 0.12 or 0.24% | pluronic reduced to Threshold for protein solubility |
| AC4 1-10 | Fbg 3 ml<br>AA/glycerol premix fbg:AA approx 50:50<br>final glycerol approx 5% | Thrombin 1X-5X | |
| AD4 1-4 | Fbg 3 ml<br>AA/glycerol premix fbg:AA approx 50:50<br>final glycerol approx 10% | Thrombin 5X No1 or 10X No2-4 | aggregates seen in scaffold |

Discussion

This work established that although an open pore could be produced by the use of a foaming Pluronic surfactant (F127 or F68) added into a (low, down to) 2 mM calcium containing fibrinogen alginate coagulation mix. However, no strategy was identified to produce a homogeneous open-pore structure with an open fibrous lamellar microstructure without micro-aggregates.

Calcium

Several in vivo experiments have demonstrated a correlation between the Ca$^{2+}$ concentration in the SM manufacture mix and the resultant inflammatory response (typically peaking around two weeks post engraftment). It has not been definitively proven that Ca$^{2+}$ ions are directly responsible for the inflammatory response, although evidence was found previously which strongly suggested that this could occur through the formation of calcium phosphate precipitate. Another conceivable possibility is that calcium ions result in the incorporation of another factor such as alginate into the resultant scaffold, which causes the inflammation. However, direct exposure of neutrophils to alginate in vitro did not lead in activation, while in the same assay calcium phosphate caused a profound neutrophil cytolytic activation.

An important result from these scaffolds was that even small increases in Ca$^{2+}$ concentration during manufacture resulted in greater inflammation than at 2 mM, although reducing calcium to 1 mM resulted in inadequate coagulation of the scaffold mixture. Consequently the preferred calcium concentration is about 2 mM.

Alginate

Alginate as a bulking and colligative agent has several potentially suitable properties (i) as with polysaccharides generally, it forms highly hydrated molecular complexes in aqueous solutions (ii) the density of hydroxy groups which confers high polarity has potential for interaction with proteins (iii) acidic residues, available for relatively strong (ionic) interactions with surface protein residues. Importantly alginate incorporation was experimentally found to create a bulky fibre mesh or lattice.

Initially, equal mass ratio mixture of fibrinogen protein and alginate was found to form a potentially stable material after Thrombin-catalysed coagulation.

However, it is possible that dependent on other variables of manufacture, the alginate ratio may exceed the potential binding capacity to fibrin protein. Experiments varying the amount of alginate showed a corresponding variation in product mass yield. However the microstructure of product is similar when alginate is added over the range 12 to 100% of protein mass.

The issue of how much alginate is difficult to resolve. While micro-structure seems not to vary much over the range, on the basis of crude mass yield of product, the total amount of alginate appears to depend mainly on the amount in the starting mixture. With concerns over the possibility that alginate may be involved in formation of micro-aggregates and calcium chelation, in addition to its useful bulking function, the use of less than a equal mass mix may be prudent. Conversely, if it can be confirmed that the amount of alginate (within structurally acceptable limits) is independent of the degree of inflammatory response, there is a counter case for maximising its incorporation in order to increase the product bulk, which may improve wound hydration and drainage and physical protection of nascent cellular structures during the initial phase of tissue ingress.

Alginate Types/Grades.

Alginate varies according the proportion of galacturonic and manuronic acid residues, corresponding to high G or high M grades. The molecular weight of polymer also varies, with corresponding variation in standard viscosity. The high G types have properties suitable for fibre extrusion and firm gel formation, whereas the high M types are suited to soft hydrogel formation and aqueous absorption or product dispersion applications. It was not clear at the outset which type might be expected to function best in a Smart Matrix, since reasonable arguments for various grades could be made a priori: the fibre forming potential of high G forms may result in an interlocking mesh of alginate and fibrin fibres in the scaffold product, and contribute to mechanical support of the fibrin; the open hydrogel property of high M may confer swelling and absorption of wound fluid and enhance the physiological milieu for wound healing. High molecular weight forms may endure longer and confer corresponding benefit for longer, low molecular weight forms may be cleared more rapidly and allow wound healing without impediment. Propylglycol-derivatised alginate could conceivably increase the interaction with protein and or surfactant, due to introduction of non-polar groups.

The experience gained over these experiments overall have shown that mostly, there is little microstructural effect of different alginate grades/types to the fibre structure of Smart Matrix scaffolds, with the exception of Kellcoid propylglycol alginate. This material resulted in truncated fibrin rods.

Cell ingress assays also indicate that all grades tested result in biocompatible cytoadhesive scaffolds for fibroblasts in vitro.

However, in vivo assessment differentiates alginate grades on the basis of inflammatory response. The histology of post-engrafted biopsies showed that the inflammatory responses in some cases occurred in zones, while in others occurred in foci centred on aggregated scaffold material which appear as dense, non-porous lumps.

Autoclaving and/or charcoal extraction (to deplete endotoxin) did not eliminate the inflammatory response, although there was a qualitative reduction in the occurrence of dense lumps with low molecular weight material.

Surfactants

Pluronic surfactants were identified initially as being potentially suitable non-detergent non-inflammatory biocompatible substances, unlikely to cause protein denaturation. Initial experiments established that coagulation could proceed in up to 1-2% Pluronic containing buffer solutions. The initially used one Pluronic F127 was similar, but slightly less foaming, that F68. Two others, P77 and P85, were less foaming. L101 and L121 were potently antifoaming.

The possible use of these antifoaming agents, L1 D1 and L121, in even low concentrations (around 0.01%) to increase the homogeneity of foam mixtures, was explored, but the antifoam effects were extremely potent, even in the presence of 100 fold excess of a foaming Pluronic, and did not yield open-pore scaffolds.

Pluronic F68 was used in preference to F127 in later experiments because it seemed to have a slightly increased foam foaming effect, which could stand to increase the open-pore structure of the SM product.

Thrombin

The original ratio of Thrombin to alginate was selected on the basis of the activity required to fully coagulate fibrinogen over 60 minutes, as was first used in our lab to prepare fibrin-degradation products by plasmin digestion (Walker & Nesheim, 1999, J Biol Chem 274 p 5201-12). This level of Thrombin was found effective to create a scaffold structure, and has been defined for SM manufacture as 1× (1×=0.0125 IU/mg fibrinogen). The realisation that partial collapse of foam structure during the fibrinogen coagulation incubation step created a two layered structure (dense and porous) prompted investigation of increasing thrombin concentration to prevent this collapse. Experiments were performed to increase the amount used several fold, extending in one experiment to 15×, although more commonly comparing 1, 4 and 8×. The amount required for an optimal open-mesh microstructure appeared to depend on the presence and concentration of surfactants. In subsequent formulations the concentration 10× has been used to obtain macro homogeneous structures using an optimal surfactant mix (such as SMOF1).

The Manufacturing Problem

The initial problem addressed in this phase of work was to identify an optimal physical scaffold structure and develop a reliable way of manufacturing to achieve this. It was recognised that inhomogeneity of the product was problematic for the host response. Dense mesh structure is cellularised progressively and functions well as a tissue scaffold. However, it was clear that an open pore structure could result in a greater rate of cellular ingress, and still retain scaffold functionality (organisation of cells, vascularisation, control of inflammation).

The persistent problem from this work was that attempts to introduce open porosity into a fibrin fibre mesh resulted in the formation of dense micro-scale aggregates which appear to act as foci for acute inflammatory response.

Various strategies were explored to overcome this. It was found that combinations of Thrombin, alginate and surfactant could achieve useful scaffold structures, although many attempts were tried before formulae which produced structures approaching an ideal were identified.

| Batch | Formulation unless stated:<br>Ca2+ = 2 mM<br>Fbg & Alginate = 2%<br>ISPAA Thrombin = 10 U/ml<br>1X = 0.0125 U/mg Fbg<br>Surfactant = 20% | Variable | Result |
|---|---|---|---|
| A5 1-10 | bFbg 6 ml<br>Thrombin 5x (7.5 U)<br>ISP AA 1% (6 ml) | OGP 0.9 or 1.7% ±<br>Pluronic F68 0.43% | OGP gives good foam but collapses to form large bubbles (approximately 1-5 mm diameter) rapidly during coagulation. Mixed OGP/pluronic combination gives a more stable bubble structure with less collapse - roughly bubbles are <1 mm dia. |
| B5 1-12 | hFbg 3 ml<br>Thrombin 5X (3.75 U)<br>Alginate 1% (3 ml) | ±Trehalose (11% in Fbg - 0.6 into 3 ml Fbg)<br>ISP AA or NM GVLMW<br>OGP 0.9 to 2.18% ±<br>Pluronic F68 0.43% | OGP addition at 0.9% is insufficient to form open pore structure, at 1.5% this forms some dense mesh and open pore, at 2.18% a fully open pore structure is formed.<br>F68 0.4% OGP 0.8% combination has more open pore structure than 1.5% OGP alone, but some dense mesh.<br>Trehalose addition increases the open pore and fibre mesh formation.<br>Increasing Thrombin from 5X to 10X with 2.18% OGP increases open porosity. |
| C5 1-6 | hFbg 3 ml - in MES NaCl pH 7.4<br>Thrombin 5X (3.75 U)<br>ISP AA 1% (3 ml) | ±Trehalose (11% in Fbg - 0.6 into 3 ml Fbg)<br>OGP 0.9 or 1.7% ±<br>Pluronic F68 0.43%<br>some in 10 x 10 cm tray | MES introduced as substitute for HEPES<br>Scaffolds worked efficiently but still not entirely top-bottom homogeneous<br>OGP:F68 0.9:0.4% (2:1) & 1.7:0.4% (4:1) tried - the latter appeared more homogeneously structured |
| D5 1-18 | hFbg 3 ml - in MES NaCl pH 7.4<br>Thrombin 10X (7.5 U)<br>ISP AA 1% (3 ml) | ±Trehalose (11% in Fbg - 0.6 into 3 ml Fbg)<br>ISP AA or NM GVLMW<br>OGP + Pluronic F68 (4:1) in low (0.25%:1%) Med (1.5% 0.4%) & high (0.5%:2%) | |
| E5 1-10 | hFbg 3 ml<br>NM GVLMW AA 3 ml<br>Thrombin 10X<br>Trehalose (11% in Fbg - 0.6 into 3 ml Fbg) | OGP + Pluronic F68 (4:1) in low (0.25%:1%)<br>15 ml 0.4% vs 30 ml 0.2% GTA cross-link buffer | |
| F5 1-22 | hFbg 3 ml<br>NM GVLMW AA 3 ml<br>Thrombin 10X<br>Trehalose (11% in Fbg - 0.6 into 3 ml Fbg) | OGP + Pluronic F68 (4:1) mix 0.5, 0.75, 1 ml | Defining 'SMOF1' |
| G5 1-11 | hFbg 3 ml<br>NM GVLMW AA 3 ml<br>Thrombin 10X<br>Trehalose(11% in Fbg - 0.6 into 3 ml Fbg) | OGP + Pluronic F68 (4:1) mix 0, 0.062-1.06 Fbg 3, 2.5, 2, 1.5 ml at 3 ml AA to reduce Fbg:AA ratio | |
| H5 1-15 hFbg 1-6 bFbg (AS) | bFbg 1 ml<br>Trehalose (11% in Fbg - 0.2 into 1 ml Fbg)<br>NM GVLMW ISP AA 1 ml | Thrombin 10X, 12X, 15X<br>Pluronic L101 (1 02 2.5 ul added to AA, or Fbg premix = 0.007 or 0.017%) | L101 was tried for a possible effect on increasing micro-homogeneity - acts as potent antifoam to the formulation. |
| I5 | SMOF1<br>OGP + Pluronic F68 (4:1) mix 0.75 to 3 ml Fbg + 3 ml AA | Silicone sheets<br>Acrylic acid derivatised Allylamine<br>textured or smooth | |
| J5 1-14 | hFbg<br>SMOF1<br>OGP + Pluronic F68 (4:1)<br>10X Thrombin | 10x10 cm tray<br>5x5 cm tray | 'Standard' batch |

| Batch | Formulation unless stated:<br>Ca2+ = 2 mM<br>Fbg & Alginate = 2%<br>ISPAA Thrombin = 10 U/ml<br>1X = 0.0125 U/mg Fbg<br>Surfactant = 20% | Variable | Result |
|---|---|---|---|
| K51-25 | hFbg 3 ml<br>SMOF1<br>OGP + Pluronic F68 (4:1)<br>10X Thrombin | ISP AA 0.75-3 ml | |

Smart Matrix Scaffold—Further Development

Discussion

Two main modifications were investigated in further development experiments. The first was the use of the sugar surfactant OGP, the second, trehalose as a protein stabilising agent.

Stabilisers

Following on from the glycerol evaluation, coagulation experiments showed that the sugars tested, (glucose, sorbitol, sucrose, and trehalose) decreased fibrinogen precipitation in the presence of alginate and pluronic surfactant, but also markedly inhibited coagulation. However, trehalose was found to have a concentration range in which it could stabilise fibrinogen from precipitation without inhibiting coagulation to a prohibitive degree. In the presence of alginate and surfactant, a coagulation profile was obtained similar to that of a simple fibrinogen solution. The evaluation of trehalose as a stabiliser in the scaffold formulation was found to give a beneficial effect on the porosity of the product, and improve the micro-structure. However, trehalose did not completely prevent the formation of micro-aggregates within the scaffold structure when pluronic surfactant was used.

Surfactant

The effect of a different type of surfactant was also examined. Pluronic (poloxamer) surfactants are well known, and established to be useful in biological systems, due to the 'mild' effects (non-denaturing, low cytotoxicity, low inflammatory potential), and these effects may be related to the surfactant mechanism. The molecules are believed to form rafts which modify surface energy, as distinct from the simple detergent structure (acyl chain and hydrophilic head-group). However, using a relatively high level of pluronic surfactant (>approx 0.9%) was clearly associated with formation of the dense micro-aggregates.

The next surfactant chosen was octyl-βD-glucopyranoside, which was found to give an improved protein stability in the coagulation test. This was found to yield an improved micro-structure, although it gave an unstable foam, resulting in very large bubbles and a heterogeneous structure. If OGP were used without pluronic, over 2% OGP was required to obtain an open pore structure, and associated dense micro-aggregate formation was also seen. The combination of pluronic F68 (or F127) with OGP markedly improved the foam stability. Specifically, a combination of pluronic plus OGP could reduce the total level of surfactant down to around 0.25% pluronic and 1% OGP. The main benefit of this was improved foam stability, pore structure and homogeneity, and an apparent reduction in formation of the dense micro-aggregate.

This led to the SM-OF1 formulation. In spite of markedly improved structure obtained there was still some formation of micro-aggregates within the scaffold product.

| Batch | Formulation unless stated:<br>Ca$^{2+}$ = 2 mM<br>Fibrinogen (Fbg) &<br>Alginate = 2%<br>Thrombin (thm) = 10 U/ml<br>Surfactant = 20% | Variable | Result |
|---|---|---|---|
| A6<br>1-6 | hFbg 3 ml<br>SMOF1<br>OGP + Pluronic F68 (4:1)<br>10X thm | Alginate 0.75-3 ml | |
| B6<br>1-6 | bFbg 2% 3 ml<br>ISP AA 2% 3 ml<br>thm 10 U/ml 10X | 1. SM-OF1 (OGP/F68 4:1)<br>2. 0.01% Span-20, final conc 0.001%<br>3. 1% Span-80, final conc 0.1%<br>4. 0.05% Span20 + 0.5% Span-80<br>5. 0.05% Span20 + 0.05% Span-80<br>6. 0.01% Span-20 | Span series surfactants give improved homogeneity and improved micro-structure over OGP/F68 alone. However low aqueous solubility of spans is a limiting factor in foam formulations. |
| C6 | | F68/OGP (4:1)<br>Span 20, Span40, Span60, Span80 (0.01%) ±<br>post incubation in NaCl (flooding scaffold mix) | Foam casting generally, and especially with OGP, show a collapse of small bubbles into much larger bubbles over a short period of incubation (typically 10-15'). Flooding with buffer after casting did not prove effective in preventing this, causing disruption to the foam structure. |
| D6<br>1-8 | | 1-2. CONTROL (OGP + F68) in Glass Tubes<br>SM-OF1 (OGP + F68) in Polystyrene Tubes<br>5-6. 0.01% S-80 in Glass Tubes<br>7-8. 0.01% S-80 in Polystyrene Tubes | |

-continued

| Batch | Formulation unless stated: $Ca^{2+}$ = 2 mM Fibrinogen (Fbg) & Alginate = 2% Thrombin (thm) = 10 U/ml Surfactant = 20% | Variable | Result |
|---|---|---|---|
| E6 | Evaluation of 100 ml mixing syringe | SM-OF1 (OGP + F68) or OGP/F68 + ODM/F68 1:1 mix or SM-OF1 w/o trehalose | Replacement of 60 ml by 100 ml mixing syringe allows for greater foam formation within 30 seconds of mixing. |
| F6 1-15 | | 1. CONTROL (OGP + F68) 2-4. ½ TRE + ½ AA + ½ (OGP + F68) 5. ½ Fbg + ½ $CaCl_2$ + ½ THR + ¼ TRE + ¼ AA + ½ (OGP + F68) 6-8. ½ TRE + ½ AA + ½ (TGP + F68) 9-11. ½ TRE + ½ AA + ½ (DGP + F68) 12-14. ½ TRE + ½ AA + ½ (OGP/F68 + DGP/F68 mix) in the ratio 1:1 15. ½ TRE + ½ AA + ½ (DGP/F68 + TGP/F68 + ODM/F68 + OGP/F68) | |
| G6 | CONTROL (½ AA + ½{DGP/F68 + OGP/F68}) in the ratio 3:1 | with lid pressed down onto foam after casting. | |
| H6 | CONTROL (½ AA + ½{DGP/F68 + OGP/F68}) (3:1) | with empty lid on top with 37° C. $H_2O$ (20 ml) in lid on top with 60° C. $H_2O$ (20 ml) in lid on top | |
| I6 | with 60° C. $H_2O$ (20 ml) in lid on top. | (½ AA + ½{DGP/F68 + OGP/F68}) (3:1) (½ AA + ½{DGP/F68 + HGP/F68}) (3:1) (½ AA + ½{DGP/F68 + ODM/F68}) (3:1). Doubling up DGP + ODM in bigger tray with 60° C. $H_2O$ (40 ml) in lid on top. | |
| J6 1-12 | | 1-3. CONTROL (½AA + ½{DGP/F68 + OGP/F68}) (3:1) DGP 7-9. (½ AA + ½{dGP/F68 + OGP/F68}) (3:1) dGP 10-12. (½ AA + ½{dGP/F68 + ODM/F68}) (3:1) dGP | |
| K6 1-15 | | 1-3. CONTROL (½ AA + ½{dGP/F68 + ODM/F68}) (3:1) dGP 4-6. (½ AA + ½{DMP/F68 + OGP/F68}) (3:1) 7-9. (½ AA + ½{DMP/F68 + ODM/F68}) (3:1) 10-12. (½ AA + ½(DdGP/F68 + OGP/F68}) (3:1) 13-15. (½ AA + ½(DdGP/F68 + ODM/F68}) (3:1) | |
| L6 | Surfactant mix: DGP + OGP + F68 | Xanthan gum (0.5%) Methyl cellulose (0.5, 0.25%) Agarose (0.25-0.5%) | Reasonable porous structures were obtained with Methyl-cellulose (better at 0.25 > 0.5%) and agarose (good at 0.25%), whereas Xanthan gum (3 ml) yielded a structure with a markedly denser fibrin organisation than seen with alginate. |
| M6 1-15 | hair dryer | 1-3. CONTROL (½ AA + ½{dGP/F68 + OGP/F68})(3:1) dGP 4-6. (6 ml of XG + ½{dGP/F68 + OGP/F68}) (3:1) 7-9. (3 ml of XG + ½{dGP/F68 + OGP/F68}) (3:1) 10-12. (1.5 ml of XG + ½{dGP/F68 + OGP/F68}) (3:1) 13-15. (750 ul of XG + ½{dGP/F68 + OGP/F68}) (3:1) | |
| N6 1-6 | hair dryer | 1-2 CONTROL (½AA + ½(dGP/F68) (100 ml) 4. CONTROL made in 60 ml tube and pushed into universal and pipette tube inserted and placed in 37° C. water bath 5a-5b. CONTROL made in 60 ml tube and pushed into two universals and pipette tube inserted and placed in 37° C. water bath 6a-6b. CONTROL made in 60 ml tube and pushed into two universals and pipette tube inserted and placed in 37° C. water bath | |
| O6 1-16 | hair dryer | 1-3 Optimized Smart Matrix Formulae 1 4-6. (DMP/F68 + DdGP/F68) (2:1): OGP/F68 (3:1) 7-9. (DMP/F68 + DdGP/F68) (2:1): ODM/F68 (3:1) 10-11. 6% Fbg (1 ml) + 6% Alg (0.5 ml) + above surfactant (used in 7-9) 12-13. 6% Fbg (1 ml + 0.5 ml MES/NaCl) + 6% Alg (0.5 ml + 250 ul MES/NaCl) + above surfactant (4%) 14-16. 6% Fbg (1 ml + 2 ml MES/NaCl) + 2% Alg (1.5 ml) + above surfactant (used in 7-9) (2%) | |

-continued

| Batch | Formulation unless stated:<br>$Ca^{2+}$ = 2 mM<br>Fibrinogen (Fbg) &<br>Alginate = 2%<br>Thrombin (thm) = 10 U/ml<br>Surfactant = 20% | Variable | Result |
|---|---|---|---|
| P6<br>1-15 | hair dryer | 1-3. hFbg + ½ Alg (UPVLVM) + ½(DMP/F68 + DdGP/F68) (2:1): ODM/F68 (3:1) 4-5. hFbg + ½ Alg (UPVLVG) + ½(DMP/F68 + DdGP/F68) (2:1): ODM/F68 (3:1) 6-15. bFbg + ½ Alg +½(DMP/F68 + DdGP/F68) (2:1): ODM/F68 (3:1) | All scaffolds flattened out due to improper freeze drying |
| Q6<br>1-15 | hFbg<br>bFbg<br>hair dryer | 1-3. hFbg + AA (UPVLVG) 0.5% + ½(DMP/F68 + DdGP/F68) (2:1): ODM/F68 (3:1)(foam level 55 ml)<br>4-5. hFbg + ½ Alg (UPVLVM) + ½(DMP/F68 + DdGP/F68) (2:1): ODM/F68 (3:1) (foam level 40 ml)<br>6-15. bFbg + ½ Alg +½(DMP/F68 + DdGP/F68) (2:1): ODM/F68 (3:1)(foam level 60 ml) | Freeze-drying without sorbitol in the pilot lyophiliser (−40° C. set shelf temp) resulted in soft pliable product with some toughness. |
| R6<br>1-17 | in presence of hair dryer<br>SMOF 2 | $H_2O$ or sorbitol lyophilisation excipient compared DMP/DdGP/ODM F68 mix 150-750 ul 375 & 750 ul in 10 × 10 | SM-OF2 375 ul to 3 ml Fbg & 1.5 ml AA gives a good balance between open porosity and open mesh fine structure. Some dense aggregates, but improved over SM-OF1<br>no surfactant - 10 ml<br>150 ul - (DMP DdGP ODM F68 mix) - 30 ml<br>250 ul - mix 55 ml<br>375 ul - mix 55 ml<br>750 ul - mix 75 ml |
| S6<br>1-13 | hair dryer | 1-2. SMOF 2 + ½(DMP/F68 + DdGP/F68) (2:1): ODM/F68 (3:1) (250 ul) (10X10)<br>3-4. SMOF 2 + ½(DMP/F68 + D4GP/F68) (2:1): ODM/F68 (3:1) (275 ul) (10X10)<br>5-6. SMOF 2 + ½(DMP/F68 + DdGP/F68) (2:1): ODM/F68 (3:1) (300 ul) (10X10)<br>7-8. SMOF 2 + ½(DMP/F68 + DdGP/F68) (2:1): ODM/F68 (3:1) (325 ul)(10X10)<br>9-10. SMOF 2 + ½(DMP/F68 + DdGP/F68) (2:1): ODM/F68 (3:1) (350 ul) (10X10)<br>11. SMOF 2 + ½(DMP/F68 + DdGP/F68) (2:1): ODM/F68 (3:1) (375 ul) (10x10)<br>12-13. SMOF 2 + M series alginate + surfactant (375 ul) (10X10) | M type AA gave structure with more micro-aggregates than the G type. |
| T6<br>1-14 | hair dryer | 1-2. SMOF 2 + 6 ml AA<br>3-4. SMOF 2 + 3 ml AA<br>5-6. SMOF 2 + 1.5 ml AA<br>7-8. SMOF 2 + 1 ml AA<br>9-10. SMOF 2 + 0.5 ml AA 11-12. SMOF 2 + 1.5 ml AA (M series pharma grade)<br>13-14. SMOF 2 + 1.5 ml AA (G series pharma grade) | The proportion of alginate over a range approx 0.2-1.1% does not have a major effect on the resultant structure. However, here this was repeated using low molecular weight pharma grade material, and evaluating a high M and High G formulation. Although there is little effect of concentration on porosity over this range, there was a decrease in micro-aggregate formation at the lower end of the range, and less with the G than M grade. |
| U6<br>1-11 | SMOF 2<br>hair dryer | foam spreading techniques<br>1-2.(10 × 10) high drop<br>3-4. SMOF 2 (10 × 10) squash<br>5. SMOF 2 (10 × 10) high drop/squash<br>6. SMOF 2 (10 × 10) 3 taps/squash<br>7-9. SMOF 2 (10 × 10) 3 taps and gentle squash<br>10. SMOF 2 (10 × 10) 3 big taps & squash with 1.2 ml of L101 (5%)<br>11. SMOF 2 (10 × 10) 3 big taps & squash in box | |
| V6<br>1-7 | hair dryer | 1. SMOF 2<br>2. ½(DMP/F127 + DdGP/F127) (2:1): OGP/F127 (3:1)<br>3B. ½(DMP/F127 + DdGP/F127) (2:1): OGP/F127 (3:1) (10X10)<br>4. SMOF 2 (2 down impeller)<br>5. SMOF 2 (1 up & 1 down impeller)<br>6B. SMOF 2 (1 up & 1 down impeller) (10x10)<br>7B. SMOF 2 (2 down impeller) (10x0) | |
| W6<br>1-10 | SMOF 2<br>hair dryer | Pharma grade G type Alginate<br>3-4. SMOF 2 with 1 ml G series Alginate<br>5-7. SMOF 2 with F127 G series Alginate<br>8-10. SMOF 2 with F127 &1 ml G series Alginate | |
| X6<br>1-15 | SM-OF2 except variable bulking agent | 1.1% XG (range 0.5-12 ml) (30 ml foam)<br>2.1% XG (6 ml)(32 ml foam)<br>3.1% XG (3 ml)(34 ml foam)<br>4-5. SMOF 2 with 1% XG (2 ml)(35 ml foam) | |

| Batch | Formulation unless stated:<br>$Ca^{2+}$ = 2 mM<br>Fibrinogen (Fbg) &<br>Alginate = 2%<br>Thrombin (thm) = 10 U/ml<br>Surfactant = 20% | Variable | Result |
|---|---|---|---|
| Y6<br>1-11 | SM-OF2<br>hair dryer | 6-7. SMOF 2 with 1% XG (1 ml)(30 ml foam)<br>8. (ml)(30 ml foam)<br>9. SMOF 2 without bulking agent(60 ml foam)<br>10-11. SMOF 2 with 2% MC (3 ml)(30 ml foam)<br>12-13. SMOF 2 with 2% MC (2 ml) (30 ml foam)<br>14-15. SMOF 2 with 2% MC (1 ml)(30 ml foam)<br>1-3. SMOF 2 (10 × 10) 3 taps & squash<br>4-6. SMOF 2 + 50% everything (10 × 10) 3 taps & squash<br>7-11. SMOF 2 tubes with 6% Fbg & 6% Alginate | |
| Z6 | SMOF 2<br>hair dryer | Fibrin fibre (individual or knitted material) | Evidence of intimate contact formed between fibrin fibres (approx 10-20 μm dia) and Smart Matrix filaments (approx 100 nm dia). |

Methodology—Notes:

A. "Hair Dryer"

Blowing warmed air over the coagulation mixture is used to try to minimise the reduction in temperature of 37° C. reagents on aeration with air at room temperature.

B. "Foam Spreading Techniques"—High Drop/Squash/Tap/Big Tap

The basic foam spreading method is several sharp taps of the tray onto the work surface. However, to spread the foam evenly over a 10×10 cm tray, the following alternatives were evaluated:

high drop=emptying the foam into the tray from a height of around 50 cm.

squash=spreading the foam using a plastic sheet (either another tray or Petri dish lid). In this case, the squash must proceed evenly and smoothly from initial contacting the lid at 30-45° on one side and slowly lowering it to achieve complete and even contact without air bubble entrapment of the whole foam, spreading it across the whole tray.

tap=sharp tap, lifting and knocking the tray onto the work surface.

big tap=holding the tray at two corners with both hands, lifting it to about 45° by tilting the wrists, then sharply flicking/slapping it down onto the work surface.

C. "Up/Down Impeller"

The impeller mix consists of two impellers (triple blade propeller design) on one shaft. We found that if they are both mounted on the spindle to thrust down, the liquid recirculates in the mixing chamber very effectively. This was found to increase the foam formation compared to the previously used wire 'bow-tie' whisk.

D. "Lid Pressed Down/Lid on Top (Empty)/Lid with Water"

There idea was to (i) accelerate heat transfer to the foam compared to standard transfer to humidified 37° C. incubator, and (ii) create a level, smooth upper foam surface.

These experiments demonstrated no great benefit. A major problem was difficulty in keeping the lids level, especially when filled with water (a very slight tilt would be increased by the additional weight of water) and minimising ooze of the foam around the sides of the tray.

This led us to use the hair dryer as an alternative means of heat transfer.

Discussion:

In this series, a formulation termed SM-OF2 (Smart Matrix optimised formula 2) was developed from SM-OF1. Scaffolds with this formulation showed a good balance between open pore structure and fibrous micro-structure. The focus of this work was to improve the pore structure homogeneity and investigate potential optimisation steps and manufacture parameters.

Surfactants

OGP appears to have an intrinsic foam instability which might limit its usefulness. Several similar sugar surfactants were investigated. The Span series was found to be of limited use due to low aqueous solubility (the preferred state being in micellar emulsion).

Acyl glucosides (such as HGP, OGP, DGP and DDGP, octyl-thio-glucopyranoside) and the maltosides (such as ODM, DM and DDM) were evaluated. It was found that benefits due to C10 and C12 over C6 or C8 were useful to decrease bubble size and increase stability. The SM-OF2 mixture produced consistent scaffolds with close to ideal open porosity and homogenous micro-structure.

Bulking Agents

Scaffolds were made using bulking agents Methyl cellulose, Xanthan gum and agarose as alternatives to Alginate.

It is interesting that agarose and methyl cellulose yielded similar structures to alginate, although the structures from Xanthan gum appeared to be denser and unlikely to function effectively in vivo. The methyl cellulose gave a structure with larger open pores than the regular alginate structure, although it might be useful at concentrations lower than 0.25-0.5%.

Agarose gave good micro-structures although dense micro-aggregates were formed.

Surfactants

On the basis of foam stability tests and coagulation tests, the sugar-surfactant types emerge as most suitable potential candidates. In spite of this data, it is not completely possible to predict the outcome of a resultant scaffold structure. Thus, cyclohexyl ethyl-βD-maltoside (CHM) appeared to yield a good foam stability, and although its coagulation assay profile was low, it produced the clear gel structure. In casting a scaffold using CHM, the resultant foam collapsed rapidly giving a clear gelatinous scaffold structure. This is robust, but when lyophilised formed a very open mesh with millimeter-scale porosity. However, other surfactants which give stable foams and support coagulation, such as Decyl-maltopyranoside and nDodecyl-sucrose gave excellent scaffolds.

Foam Stability Tests:
Method

20% aqueous agents were diluted into (1) diH$_2$O (2) 1% alginate/Mes/NaCl pH7.4 (3) 1% bFbg/Mes/NaCl pH7.4, to give 1% (50 μl plus 950 μl diluent). Solutions were whisked to an equilibrium foam in a 30 ml conical bottomed universal tube. The height of foam achieved, and time for 100 μl liquid to form in the base of the tube cone was measured. Results are ranked from least to greatest foam stability.

Table of Surfactant agents used in foam stability tests.

| Abbreviation | Type | Name |
|---|---|---|
| PPS | SB | 3-(1-pyrolidino)-1-propane sulphonate |
| TritonX45 | N | 4-(1,1,3,3-Tetramethylbutyl)phenyl-polyethylene glycol |
| DdGP | N | dodecyl glucopyranoside |
| SucO | N | sucrose mon/di-oleate |
| CHAPS | A | 3-[(3-Cholamidopropyl) dimethylammonio]-1-propanesulfonate hydrate |
| HGP | N | Hexyl glucopyranoside |
| DMAB | B | Decyl-trimethylammonium bromide |
| CHM | N | cyclo hexylethyl-βD-maltoside |
| Genapol | N | polyethylene glycol Lauryl ether |
| Tween20 | N | Polyethyleneglycol(20) sorbitan monolaurate |
| THESIT | N | Polyethylene glycol dodecyl ether |
| TritonX100 | N | 4-(1,1,3,3-Tetramethylbutyl)phenyl-polyethylene glycol |
| NP40 | N | (Octylphenoxy)polyethoxyethanol |
| IGEPAL CA630 | N | Octylphenoxy-polyethoxyethanol |
| Brij-35 | N | Polyoxyethylene (23) lauryl ether |
| Empigen | Z | N,N-Dimethyl-N-dodecyl glycine betaine |
| Pluronic F127 | N | polyethoxy-polypropyloxy copolymer |
| Sarkosyl | B | N-lauryl-sarcosine |
| DOC | A | Deoxycholate |
| DMG | N | Decanoyl-N-methylglucamide |
| Pluronic F68 | N | polyethoxy-polypropyloxy copolymer |
| DGP | N | decyl-βD-glucopyranoside |
| SDS | A | sodium dodecyl sulphate |
| SucL | N | sucrose mono/di-laurate |
| OGP | N | octyl-βD-glucopyranoside |
| dDMP | N | dodecyl-βD-maltopyranoside |
| ODM/F68 | N | octyl-βD-maltoside/F68 |
| DdSuc | N | n-dodecylsucrose |
| ODM | N | octyl-βD-maltopyranoside |
| nDSuc | N | n-decylsucrose |
| DMP | N | decyl-βD-maltopyranoside |

Foam Stability Test Results

| | | 1% Aqueous | | | AA/MesNaCl pH 7.4 | | | 1% Fbg/ MesNaCl pH 7.4 | | | 1% Fbg/AA/ MesNaCl pH 7.4 | | |
|---|---|---|---|---|---|---|---|---|---|---|---|---|---|
| Abbreviation | Type | Height/mm | % | Stability | Height/mm | % | Stability | Height/mm | % | Stability | Height/mm | % | Stability |
| PPS | SB | 11 | 0 | none | 11 | 0 | none | 21 | 91 | 2' | | | |
| TritonX45 | N | 11 | 0 | none | 11 | 0 | none | 11 | | None | | | |
| DdGP | N | 12 | 9 | none | 24 | 118 | 29" | 14 | 33 | None | 11 | 0 | 2" |
| SucO | N | 13 | 18 | none | 15 | 36 | 2" | 14 | 33 | 3" | 11 | 0 | None |
| CHAPS | A | 25 | 127 | 5" | 36 | 227 | 1'49" | 33 | 242 | 2'32" | | | |
| HGP | N | 11 | 0 | 5" | 25 | 154 | 5" | 30 | 209 | 4'10" | 27 | 176 | 2" |
| DMAB | B | 11 | 0 | 5" | 20 | 82 | 3" | 30 | 209 | 9'35" | 29 | 198 | 18" |
| CHM | N | 23 | 109 | 10" | 28 | 155 | 8" | 33 | 200 | 14'10" | 27 | 176 | 2'19" |
| Genapol | N | 28 | 155 | 33" | 13 | 18 | 18" | 29 | 164 | 1'20" | | | |
| Tween20 | N | 26 | 136 | 1'5" | 28 | 155 | 1'09" | | | | | | |
| THESIT | N | 29 | 164 | 1'6" | 23 | 109 | 1'10" | 28 | 155 | 1'10" | | | |
| TritonX100 | N | 29 | 164 | 1'07" | 27 | 145 | 1'10" | 26 | 136 | 1'24" | | | |
| NP40 | N | 29 | 164 | 1'10" | 34 | 209 | 1'15" | | | | | | |
| IGEPAL CA630 | N | 36 | 227 | 1'10" | 27 | 145 | 1'38" | 27 | 145 | 1'21 | | | |
| Brij-35 | N | 26 | 136 | 1'26" | 21 | 91 | 57" | | | | | | |
| Empigen | Z | 38 | 245 | 1'30" | 35 | 218 | 1'58" | 32 | 191 | 1'28" | | | |
| Pluronic F127 | N | 27 | 145 | 1'42" | 24 | 118 | 2'05" | 28 | 187 | 2'02" | | | |
| Sarkosyl | B | 33 | 200 | 2'07" | 37 | 236 | 2'35" | 33 | 200 | 2'17" | | | |
| DOC | A | 44 | 300 | 2'20" | 37 | 236 | 1'48" | 38 | 245 | 2'40" | | | |
| DMG | N | 33 | 200 | 2'50" | 29 | 164 | 5' | 40 | 236 | 3'25 | | | |
| Pluronic F68 | N | 29 | 164 | 2'47" | 36 | 227 | 2'37" | 29 | 198 | 2'35" | | | |
| DGP | N | 34 | 209 | 3'2" | 31 | 182 | 2'32" | 34 | 209 | 4'22" | 29 | 198 | 2'54" |
| SDS | A | 40 | 264 | 3'30" | 36 | 227 | 2'02" | | | | | | |
| SucL | N | 24 | 118 | 3'34" | 16 | 45 | 6" | 28 | | 2'45" | 22 | 100 | 1'52" |
| OGP | N | 43 | 291 | 4'27" | 40 | 264 | 3'22" | 33 | 200 | 5'23" | 46 | 385 | 4'48" |
| dDMP | N | 27 | 176 | 6'37" | 30 | 209 | 5'17" | 29 | 198 | 7'55" | 29 | 198 | 5' |
| ODM/F68 | N | 44 | 300 | 6'50' | 35 | 218 | 3'24" | | | | | | |
| DdSuc | N | 34 | 209 | 11'04' | 26 | 136 | 5' | 28 | 187 | 5'29" | 30 | 209 | 5'54" |
| ODM | N | 45 | 309 | 11'25" | 39 | 255 | 5'30" | 33 | 200 | 10'01" | 42 | 341 | 9'35" |
| nDSuc | N | 31 | 182 | 11'36 | 28 | 155 | 5' | 30 | 209 | 6'09" | 25 | 154 | 4'30" |
| DMP | N | 45 | 309 | 17'40" | 29 | 164 | 12'35" | 37 | 236 | 11'07" | 34 | 253 | 8'44" |
| SMOF-2 DdGP/DMP/ODM/F68 | N | 35 | 218 | 5'45" | 35 | 218 | 4'55" | 38 | 297 | 6'45" | 29 | 198 | 4'39" |
| OGP + F68 0.5% each | N | | | | 30 | 209 | 2'08" | | | | | | |
| DMP + F68 0.5% each | N | | | | 29 | 198 | 4'25" | | | | | | |

| Abbreviation | 1% Type | Aqueous Height/mm | % | Stability | AA/MesNaCl pH 7.4 Height/mm | % | Stability | 1% Fbg/ MesNaCl pH 7.4 Height/mm | % | Stability | 1% Fbg/AA/ MesNaCl pH 7.4 Height/mm | % | Stability |
|---|---|---|---|---|---|---|---|---|---|---|---|---|---|
| OGP + F127 0.5% each | N | | | | 26 | 136 | 2'44" | | | | | | |
| DMP + F127 0.5% each | N | | | | 26 | 136 | 4'27" | | | | | | |
| DMP/F127 (4:1) | N | 33 | 200 | 9'20" | | | | 36 | 227 | 8'14" | | | |
| DMP/F68 (4:1) | N | 29 | 163 | 5'30 | | | | 29 | 136 | 4'50" | | | |

Effect of Alternative Surfactants on Fibrinogen Solubility and Coagulation:

Aim

To evaluate the effect of different surfactants on the solubility and enzymatic coagulation of a fibrinogen solution, a coagulation assay, in which solution turbidity at 425 nm was monitored over 20 min, was carried out for each surfactant.

Method

A 1M $CaCl_2$ solution was freshly prepared and sterile filtered before use. Autoclaved MES/NaCl buffer, with 25 mM MES and 150 mM NaCl, was used as diluent to carry out the coagulation assays. Bovine fibrinogen (BFbg) solution was made up to 2% in MES/NaCl buffer. Thrombin solution was 10 U/ml. Finally, a 20% surfactant solution was made in $dH_2O$.

All reagents except thrombin were mixed in a disposable, plastic cuvette and the initial OD value at 425 nm was recorded. Thrombin was then added to the mix and OD at 425 nm was measured every minute until coagulation was complete, showing OD off scale (>2.5), or over 20 min if coagulation did not occur.

For each surfactant, increasing concentrations were tested, with 6 tests carried out per surfactant. Control sample did not contain surfactant.

The sequence of mixing was: $CaCl_2$, BFbg, MES/NaCl, surfactant and, after recording initial OD value, thrombin. The total volume in the cuvette was always 1 ml.

At the end of the assay, the gel quality was checked by comparing each test to the control.

Maximum rate and lag time were calculated for each test.

The table below summarises the reagents used in this study, their concentration and the volumes added per test:

| REAGENT | CONCENTRATION | VOLUME (μl) CONTROL | A | B | C | D | E |
|---|---|---|---|---|---|---|---|
| CaCl2 | 1M | 2.7 | 2.7 | 2.7 | 2.7 | 2.7 | 2.7 |
| BFbg | 2% | 500 | 500 | 500 | 500 | 500 | 500 |
| Surfactant | 20% | 0 | 6.25 | 12.5 | 25 | 50 | 100 |
| MES/NaCl | 25/150 mM | 448 | 442 | 438 | 423 | 398 | 348 |
| Thrombin | 10 U/ml | 50 | 50 | 50 | 50 | 50 | 50 |

Summary of reagents, concentrations and volumes added in the coagulation assays.

Results

Initial Values, Gel Quality, Maximum Rate and Lag Time

The table below summarises the results for all the surfactants (mean of three runs):

| Abbreviation | type | Name | CONC (%) | INITIAL BASE | MAX RATE (OD/min) | LAG TIME (min) | GEL % | Notes |
|---|---|---|---|---|---|---|---|---|
| SDS | A | Sodium dodecyl sulphate | 0 | 0.122 | 1.273 | 3 | 100 | complete |
| | | | 0.125 | 0.181 | n/a | n/a | 0 | inhibition |
| | | | 0.25 | 0.143 | n/a | n/a | 0 | |
| | | | 0.5 | 0.115 | n/a | n/a | 0 | |
| | | | 1 | 0.09 | n/a | n/a | 0 | |
| | | | 2 | 0.074 | n/a | n/a | 0 | |
| nLS | A | n-Lauryl sarcosine | 0 | 0.06 | 1.43 | 3 | 100 | complete |
| | | | 0.125 | 0.055 | 1.018 | 5 | 20 | inhibition |
| | | | 0.25 | 0.052 | n/a | n/a | 0 | |
| | | | 0.5 | 0.038 | n/a | n/a | 0 | |
| | | | 1 | 0.036 | n/a | n/a | 0 | |
| | | | 2 | 0.036 | n/a | n/a | 0 | |
| DOCA | A | Deoxycholic acid | 0 | 0.084 | 1.168 | 2 | 100 | complete |
| | | | 0.125 | 0.118 | 1.306 | 4 | 60 | inhibition |
| | | | 0.25 | 0.121 | 0.0928 | 15 | 20 | |
| | | | 0.5 | 0.073 | n/a | n/a | 0 | |

-continued

| Abbreviation | type | Name | CONC (%) | INTIAL BASE | MAX RATE (OD/min) | LAG TIME (min) | GEL % | Notes |
|---|---|---|---|---|---|---|---|---|
| | | | 1 | 0.052 | n/a | n/a | 0 | |
| | | | 2 | 0.058 | n/a | n/a | 0 | |
| CHAPS | A | 3-[(3-Cholamidopropyl)dimethylammonio]-1-propanesulfonate hydrate | 0 | 0.098 | 0.726 | 3 | 100 | inhibition |
| | | | 0.125 | 0.095 | n/a | n/a | 90 | |
| | | | 0.25 | 0.106 | n/a | n/a | 80 | |
| | | | 0.5 | 0.094 | n/a | n/a | 80 | |
| | | | 1 | 0.099 | n/a | n/a | 70 | |
| | | | 2 | 0.098 | n/a | n/a | 50 | |
| DMAB | B | Decyl-trimethyl-ammonium bromide | 0 | 0.092 | 0.644 | 3 | 100 | inhibition |
| | | | 0.125 | 0.094 | 0.8495 | 2 | 110 | |
| | | | 0.25 | 0.136 | 1.242 | 2 | 80 | |
| | | | 0.5 | 0.143 | 1.556 | 1 | 90 | |
| | | | 1 | 0.276 | 0.109 | 0 | 80 | |
| | | | 2 | 0.146 | 0.217 | 3 | 10 | |
| EMPIGEN | Z | N,N-Dimethyl-N-dodecyl glycine betaine | 0 | 0.066 | 1.108 | 3 | 100 | inhibition |
| | | | 0.125 | 0.066 | 0.083 | 3 | 110 | |
| | | | 0.25 | 0.077 | 0.7805 | 3 | 90 | |
| | | | 0.5 | 0.095 | 0.801 | 2 | 40 | |
| | | | 1 | 0.107 | 0.814 | 2 | 40 | |
| | | | 2 | 0.111 | 0.199 | 3 | 40 | |
| GENAPOL | N | polyethylene glycol Lauryl ether | 0 | 0.111 | 0.597 | 5 | 100 | |
| | | | 0.125 | 0.133 | n/a | n/a | 90 | |
| | | | 0.25 | 0.122 | 0.2745 | 6 | 100 | |
| | | | 0.5 | 0.13 | 0.9505 | 4 | 110 | |
| | | | 1 | 0.142 | 1.77 | 3 | 130 | |
| | | | 2 | 0.14 | 1.688 | 0 | 130 | |
| NP40 | N | (Octylphenoxy)polyethoxyethanol | 0 | 0.147 | 0.927 | 4 | 100 | slight inhibition |
| | | | 0.125 | 0.132 | 1.198 | 4 | 90 | |
| | | | 0.25 | 0.144 | 1.23 | 4 | 100 | |
| | | | 0.5 | 0.154 | 1.45 | 4 | 80 | |
| | | | 1 | 0.154 | 0.874 | 0 | 80 | |
| | | | 2 | 0.161 | 1.282 | 3 | 60 | |
| IGEPAL | N | Octylphenoxy-polyethoxyethanol | 0 | 0.09 | 0.72 | 4 | 100 | |
| | | | 0.125 | 0.077 | 0.447 | 4 | 110 | |
| | | | 0.25 | 0.072 | 0.776 | 4 | 130 | |
| | | | 0.5 | 0.068 | 0.756 | 1 | 140 | |
| | | | 1 | 0.085 | 0.99 | 3 | 120 | |
| | | | 2 | 0.107 | 0.9695 | 2 | 120 | |
| MEGA-10 | N | Decanoyl-N-methylglucamide | 0 | 0.115 | 0.651 | 3 | 100 | slight inhibition |
| | | | 0.125 | 0.132 | 0.635 | 4 | 90 | |
| | | | 0.25 | 0.138 | 0.433 | 4 | 90 | |
| | | | 0.5 | 0.131 | n/a | n/a | 80 | |
| | | | 1 | 0.146 | n/a | n/a | 60 | |
| | | | 2 | 0.152 | n/a | n/a | 60 | |
| BRIJ 35 | N | Polyoxyethylene (23) lauryl ether | 0 | 0.05 | 1.831 | 3 | 100 | |
| | | | 0.125 | 0.058 | 1.25 | 4 | 100 | |
| | | | 0.25 | 0.064 | 1.36 | 4 | 100 | |
| | | | 0.5 | 0.055 | 1.573 | 3 | 95 | |
| | | | 1 | 0.061 | 2.096 | 1 | 90 | |
| | | | 2 | 0.115 | 1.811 | 0 | 80 | |
| Triton X-100 | N | 4-(1,1,3,3-Tetramethylbutyl)phenyl-polyethylene glycol | 0 | 0.158 | 0.772 | 5 | 100 | slight inhibition |
| | | | 0.125 | 0.146 | 0.706 | 4 | 90 | |
| | | | 0.25 | 0.141 | 0.7915 | 4 | 100 | |
| | | | 0.5 | 0.138 | 1.142 | 3 | 80 | |
| | | | 1 | 0.133 | 1.377 | 3 | 80 | |
| | | | 2 | 0.135 | 2.024 | 1 | 60 | |
| TWEEN-20 | N | Polyethyleneglycol(20) sorbitan monolaurate | 0 | 0.153 | 0.686 | 4 | 100 | slight inhibition |
| | | | 0.125 | 0.155 | 0.924 | 4 | 90 | |
| | | | 0.25 | 0.164 | 1.732 | 4 | 100 | |
| | | | 0.5 | 0.183 | 1.813 | 2 | 90 | |
| | | | 1 | 0.285 | 1.685 | 1 | 70 | |
| | | | 2 | 0.149 | 0.7025 | 4 | 80 | |
| THESIT | N | Polyethylene glycol dodecyl ether | 0 | 0.138 | 1.014 | 4 | 100 | |
| | | | 0.125 | 0.13 | 1.59 | 5 | 120 | |
| | | | 0.25 | 0.126 | 1.991 | 3 | 110 | |
| | | | 0.5 | 0.13 | 1.831 | 3 | 120 | |
| | | | 1 | 0.131 | 1.215 | 1 | 120 | |
| | | | 2 | 0.139 | 1.659 | 1 | 120 | |
| F-127 | N | polyethoxy-polypropyloxy copolomer | 0 | 0.12 | 0.824 | 3 | 100 | Fbg ppt at ≥1% |
| | | | 0.125 | 0.117 | 1.492 | 2 | 100 | |
| | | | 0.25 | 0.119 | 2.018 | 1 | 100 | |
| | | | 0.5 | 0.122 | 2.053 | 0 | 100 | |
| | | | 1 | 0.148 | 1.691 | 0 | 100 | |
| | | | 2 | 0.743 | 0.192 | 0 | 100 | |

-continued

| Abbreviation | type | Name | CONC (%) | INTIAL BASE | MAX RATE (OD/min) | LAG TIME (min) | GEL % | Notes |
|---|---|---|---|---|---|---|---|---|
| F-68 | N | polyethoxy-polypropyloxy copolomer | 0 | 0.113 | 0.728 | 3 | 100 | Fbg ppt at ≥1% |
| | | | 0.125 | 0.115 | 1.449 | 1 | 100 | |
| | | | 0.25 | 0.115 | 1.124 | 0 | 100 | |
| | | | 0.5 | 0.122 | 2.039 | 0 | 90 | |
| | | | 1 | 0.172 | 1.099 | 0 | 90 | |
| | | | 2 | 1.62 | 0.189 | 0 | 90 | |
| CHM | N | cyclo hexylethyl-βD-maltoside | 0 | 0.114 | 0.398 | 5 | 100 | Clear gel |
| | | | 0.125 | 0.107 | 0.277 | 5 | 150 | |
| | | | 0.25 | 0.11 | n/a | n/a | 120 | |
| | | | 0.5 | 0.108 | n/a | n/a | 110 | |
| | | | 1 | 0.104 | n/a | n/a | 100 | |
| | | | 2 | 0.114 | n/a | n/a | 70 | |
| DdMP | N | Dodecyl-maltopyranoside | 0 | 0.049 | 1.312 | 3 | 100 | Clear gel at ≥1% |
| | | | 0.125 | 0.052 | 2.063 | 4 | 100 | |
| | | | 0.25 | 0.053 | 2.081 | 4 | 110 | |
| | | | 0.5 | 0.055 | 1.187 | 5 | 120 | |
| | | | 1 | 0.068 | 0.37 | 6 | 100 | |
| | | | 2 | 0.087 | 0.62 | 6 | 100 | |
| nDS | N | n-Decyl-sucrose | 0 | 0.051 | 2.055 | 4 | 100 | slight inhibition, Clear gel at ≥1% |
| | | | 0.125 | 0.051 | 1.588 | 4 | 100 | |
| | | | 0.25 | 0.049 | 2.086 | 4 | 100 | |
| | | | 0.5 | 0.054 | 1.325 | 4 | 90 | |
| | | | 1 | 0.048 | 0.263 | 3 | 80 | |
| | | | 2 | 0.048 | 0.281 | 2 | 80 | |
| DdS | N | n-Dodecyl sucrose | 0 | 0.051 | 2.003 | 4 | 100 | |
| | | | 0.125 | 0.057 | 1.857 | 4 | 100 | |
| | | | 0.25 | 0.052 | 1.264 | 4 | 120 | |
| | | | 0.5 | 0.05 | 0.669 | 5 | 110 | |
| | | | 1 | 0.056 | 0.183 | 2 | 130 | |
| | | | 2 | 0.052 | 1.638 | 3 | 130 | |
| SUC-L | N | sucrose mono/di laurate | 0 | 0.054 | 1.202 | 4 | 100 | slight inhibition |
| | | | 0.125 | 0.114 | 1.335 | 4 | 90 | |
| | | | 0.25 | 0.089 | 1.358 | 4 | 90 | |
| | | | 0.5 | 0.069 | 1.894 | 3 | 90 | |
| | | | 1 | 0.078 | 1.849 | 4 | 80 | |
| | | | 2 | 0.082 | 2 | 3 | 70 | |
| SUC-0 | N | Sucrose mono/di-oleate | 0 | 0.059 | 1.666 | 4 | 100 | Turbidity |
| | | | 0.125 | 0.225 | 1.67 | 4 | 100 | |
| | | | 0.25 | 1.282 | 0.816 | 4 | 100 | |
| | | | 0.5 | 1.485 | 1.027 | 4 | 80 | |
| | | | 1 | 1.534 | 0.808 | 3 | 90 | |
| | | | 2 | 1.38 | 0.941 | 3 | 90 | |
| SMOF-2 | N | 8% DMP 4% DDGP 4% ODM 4% Pluronic F68 (Total Surfactant mass 20%) | 0 | 0.121 | 0.796 | 4 | 100 | |
| | | | 0.125 | 0.121 | 0.786 | 4 | 110 | |
| | | | 0.25 | 0.121 | 0.738 | 4 | 110 | |
| | | | 0.5 | 0.123 | 0.73 | 4 | 120 | |
| | | | 1 | 0.124 | 0.832 | 4 | 120 | |
| | | | 2 | 0.128 | 0.978 | 4 | 110 | |
| PPS | SB | 3-(1-pyrolidino)-1-propane sulphonate | 0 | 0.1 | 0.365 | 5 | 100 | clear gel |
| | | | 0.125 | 0.102 | 0.118 | 6 | 110 | |
| | | | 0.25 | 0.101 | 0.065 | 6 | 110 | |
| | | | 0.5 | 0.101 | 0.402 | 6 | 110 | |
| | | | 1 | 0.12 | n/a | n/a | 100 | |
| | | | 2 | 0.13 | n/a | n/a | 90 | |

Summary of initial values, gel quality, maximum rate and lag time for all the surfactants tested.

Discussion

This study aimed to evaluate the effect of different classes of surfactant on the solubility and enzymatic coagulation of bovine fibrinogen. Coagulation tests were carried out for each surfactant over the range 0.125-2% w/v. An important limitation of this turbidimetric method of measuring coagulation is that some surfactants can result in a clear gel type coagulation. Hence in order to identify inhibited coagulation from clear gel formation, a subjective assessment of gel strength in relation to the control was made.

Anionic Surfactants

All the anionic surfactants studied here caused a potent inhibition of fibrinogen coagulation within the concentration range tested, CHAPS having the least potent effect. SDS is a classic anionic surfactant used as a denaturing agent for proteins in biochemical techniques such as SDS-PAGE electrophoresis, where proteins are denatured and separated according to their size. The fact that coagulation was found to be inhibited is unsurprising. Similar effects of n-lauryl sarcosine, deoxycholate and CHAPS indicate that this type of surfactant is not compatible with Smart Matrix manufacturing.

Basic and Zwitterionic Surfactants

The basic surfactant range is smaller than other types. However, a relatively simple structure, BMAB, was inhibitory at concentrations relevant to foaming. Similarly, zwitterionic surfactants are less numerous than other types, and the one studied here, EMPIGEN, also inhibited coagulation at foaming concentrations.

Non-Ionic Surfactants

There are a large number of non-ionic surfactants in common usage, and of the representative ones tested, most were found to support thrombin-catalysed fbg coagulation. Some well known types, such as the polyoxyethylene types (GENAPOL, THESIT, IGEPAL, BRIJ-35) supported coagulation over the whole testing range. However, other similar surfactants did not (Triton X100, Tween 20). MEGA-10 also proved to be inhibitory, at 1% or more. The polyethoxy/polypropyloxy-block copolymer types (Pluronic F127, Pluronic F68) supported coagulation, although they did increase protein precipitation at 1% or more, which was more marked than with GENAPOL or IGEPAL. This might explain the occurrence of micro-aggregates within scaffolds formed using Pluronic surfactant.

In this series several sugar-based surfactants were tested to extend previous work on other similar compounds. An interesting, and salutatory result, was from Cyclo-hexyl-propyl-maltoside. This caused formation of a clear gel, and thus showed a very low optical kinetic profile, although it may be a suitable surfactant for SM manufacture.

A similar effect was shown by dodecyl-maltoside and n-decyl-sucrose. By contrast to dodecyl-maltoside with strong gels, decyl-sucrose gave weaker gels. A difference in gel formation was found between n-decyl-sucrose which slightly reduced gel strength, and n-dodecyl-sucrose, which gave a good gel strength. The results for SUC-L and SUC-O were also notable, but reflective of the presence of di-acylated as well as mono-acylated sucrose in these preparations. SUC-L gave a noticeably weaker gel than n-dodecylsucrose. SUC-O caused initial turbidity, which might be due to formation of a separate surfactant droplet phase from the oleate chain (18 carbons), or a protein precipitate.

Sulphobetanes

The sulphobetanes are candidate molecules of potential interest for regulating coagulation. The simple sulphobetaines studied here did show a modulation of coagulation with the formation of a clear (non-turbid) gel. The value for manufacture is limited because of a lack of surfactant foaming character.

Implications for Scaffold Manufacture

This work identifies a basic criterion for potential suitability of surfactants for use as agents to manufacture a fibrin-based scaffold using a simple assay method. Anionic, cationic and zwitterionic surfactants inhibit enzymic fibrinogen coagulation, and are therefore unsuitable for further consideration. Several non-ionic surfactants here are also unsuitable because they cause a degree of inhibition of the coagulation process (NP40, MEGA-10, TritonX100, Tween20, n-Decyl-sucrose, Sucrose-mono/di-laurate, or sucrose mono/di oleate). Other non-ionic surfactants do not inhibit coagulation, at up to the 2% w/v tested here (Genapol, IGEPAL, THESIT, Pluronic F68, F127, BRIJ-35, cyclo hexyl-ethyl-βD-maltoside, dodecyl-βD-maltoside, n-dodecyl sucrose), and thus show potential for use in a fibrin scaffold manufacture process.

Coagulation Assay Detailed Results

The coagulation results for each surfactant are means of three runs, for each surfactant concentration (mass/vol), A=0.125%, B=0.5%, C=0.5%, D=1%, E=2%.

2-Cyclohexylethyl β-D Maltoside (CHM)
  Coagulation was seen in test A:
3-(1-Pyridinio)-1-Propanesulfonate (PPS)
  Coagulation was seen in test C:
Polyethylene Glycol Lauryl Ether (GENAPOL C-100)
  Coagulation rate increased with increased concentration of surfactant. Tests C, D and E showed higher coagulation rates than the control. Test A showed no coagulation:
Octylphenoxy-Polyethoxyethanol (IGEPAL CA 630)
  Coagulation was observed at all surfactant concentrations:
N,N-Dimethyl-N-Dodecyl Glycine Betaine (EMPIGEN)
  Complete coagulation was only observed for test B, with a very similar rate to that of the control sample:
Deoxycholic Acid (DOCA)
  Coagulation was only observed at the lowest concentration of surfactant:
3-[(3-Chlolamidopropyl)Dimethylammonio]-1-Propanesulfonate Hydrate (CHAPS)
  Coagulation was not observed at every concentration of surfactant:
Decyltrimethylammonium Bromide (DMAB)
  Coagulation was observed at all concentrations of DMAB except at the highest (test E). For test D initial precipitation of BFbg was seen:
Decanoyl-N-Methylglucamide (DMG)
  Coagulation was observed at the lowest concentrations of DMG (tests A and B):
(Octylphenoxy)Polyethoxyethanol, Nonidet P-40 (NP40)
  Complete coagulation was measured at all surfactant concentrations, with a higher rate than that of the control:
4-(1,1,3,3-Tetramethylbutyl)Phenyl-Polyethylene Glycol (Triton X-100)
  Complete coagulation was measured at all concentrations, with coagulation rate increasing with surfactant concentration:
Polyethyleneglycol (20) Sorbitan Monolaurate (Tween 20)
  As with Triton X-100, complete coagulation was measured at all concentrations, with coagulation rate increasing with surfactant concentration. However, the lowest coagulation rate was observed at the highest concentration of Tween 20:
Pluronic F-68
  Initial precipitation of BFbg was observed with this surfactant, especially at the highest concentrations (tests D and E):
Pluronic F-127
  Same observations as with PLURONIC F-68:
Sodium Dodecyl Sulphate (SDS)
  SDS did not allow coagulation at any concentration:
Smart Matrix Optimised Formula-2 (SMOF-2)
  Coagulation was observed at all concentrations of surfactant, with a very similar rate to that of the control sample:
Polyethylene Glycol Dodecyl Ether (THESIT)
  Coagulation was observed at all concentrations of THESIT. Coagulation rate increased with the surfactant concentration:
N-Decanoylsucrose (nDS)
  Coagulation was observed at the lowest concentrations of nDS (tests A and B). Coagulation rate decreased with increasing concentration of nDS:
N-Dodecanoylsucrose (ndDS)
  For this surfactant, coagulation was observed at the highest (test E) and the lowest (test A) concentrations. Coagulation was also seen in test B, although it was slower than the control, test A and test E:
Dodecyl β-D-Maltopyranoside (dDMP)
  Coagulation was observed at the lowest concentrations of dDMP (tests A and B):
Polyoxyethylene (23) Lauryl Ether (BRIJ-35)
  Coagulation was observed at all concentrations. Coagulation rate increased with surfactant concentration:
N-Lauryl-Sarcosine (nLS)
  Coagulation was observed for test A, lowest concentration, but it was not complete:
Sucrose Mono/Di-Laurate (SUC-L)

Coagulation occurred at all concentrations of surfactant. Coagulation rate for tests A to E was faster than that of control:

Sucrose Mono/Di-Oleate (SUC-O)

As with SUC-L, coagulation occurred at all concentrations of surfactant and coagulation rate for tests A to E was faster than that of control. Initial precipitation of BFbg was seen in tests B to E.

Coagulation Results

Effect of Poly-Hydroxyl Molecules as Stabilising Agents on Coagulation (I): Fibrinogen.

Aim

In order to exploit the coagulation of fibrinogen to manufacture porous scaffolds for biological and therapeutic purposes, it is desirable to control the three-dimensional organisation of the coagulated fibrin. To achieve this it has been found useful to combine bulking agents and surfactants with fibrinogen. However, some precipitation of fibrinogen from such mixed solutions has been found to occur readily, which is undesirable. The aim of this series of experiments is to evaluate the effect of poly-ols (especially sugars and sugar alcohols) as potential stabilising agents, on the solubility and enzymatic coagulation of fibrinogen solutions as used for manufacturing scaffolds. In this first set, effects on a simple buffered fibrinogen/thrombin coagulation mixture are evaluated. In subsequent studies this is extended to mixtures including alginate, and alginate plus surfactant. The basal solution stability and coagulation is measured through turbidity at 425 nm, monitored over 20 min. The poly-ols tested were glycerol, sorbitol, glucose, sucrose, trehalose and raffinose.

Method

A 1M $CaCl_2$ solution was freshly prepared and filtered through a 0.2 μm filter before use. Autoclaved MES/NaCl buffer (25 mM MES, 150 mM NaCl pH 7.4) was used to dissolve fibrinogen, and as a diluent. Bovine fibrinogen (bFbg) solution was made up at 2% in MES/NaCl buffer. Thrombin solution was 10 U/ml in 25 mM HEPES, 150 mM NaCl, pH 7.4, aliquoted and stored at −80° C. Glycerol was used directly. Test sugars were dissolved in $diH_2O$ at approximately saturation at 37° C. (% wt/vol of each was recorded) and tested over a 6 fold dilution range, at the final % wt/vol in the assay given in the results.

$CaCl_2$, bFbg, MES/NaCl and test sugar were added sequentially into a disposable plastic semi-micro cuvette and mixed thoroughly. The initial OD at 425 nm was recorded. Then thrombin was added, and immediately mixed to initiate coagulation and the OD was recorded every minute for 20 min or until coagulation was complete. The total assay volume was 1 ml.

At the end of the assay, the gel quality was manually assessed by comparing each test to the control.

Maximum rate and lag time were calculated for each test.

Results
Summary of Stability & Coagulation Assay Data.

| SUGARS | % wt/vol | vol stock (μl) | INTIAL BASE | MAX RATE (OD/min) | LAG TIME (min) | GEL % |
|---|---|---|---|---|---|---|
| GLYCEROL | 0 | 0 | 0.044 | 1.238 | 3 | 100 |
|  | 1.25 | 12.5 | 0.042 | 0.026 | 6 | 100 |
|  | 2.50 | 25 | 0.043 | 0.108 | 7 | 100 |
|  | 5 | 50 | 0.061 | 0.034 | 6 | 100 |
|  | 10 | 100 | 0.047 | 0.032 | n/a | 90 |
|  | 20 | 200 | 0.045 | 0.010 | n/a | 90 |
| SORBITOL | 0 | 0 | 0.055 | 1.432 | 3 | 100 |
|  | 1.10 | 12.5 | 0.056 | 0.188 | 1 | 100 |
|  | 2.20 | 25 | 0.059 | 0.151 | 1 | 100 |
|  | 4.30 | 50 | 0.051 | 0.109 | 1 | 90 |
|  | 8.70 | 100 | 0.047 | 0.077 | 1 | 90 |
|  | 17.40 | 200 | 0.042 | 0.054 | 1 | 90 |
| GLUCOSE | 0 | 0 | 0.054 | 1.555 | 4 | 100 |
|  | 1.10 | 12.5 | 0.051 | 0.187 | 4 | 90 |
|  | 2.30 | 25 | 0.051 | 0.156 | 3 | 90 |
|  | 4.50 | 50 | 0.048 | 0.129 | 1 | 80 |
|  | 9.10 | 100 | 0.046 | 0.081 | 1 | 80 |
|  | 18.20 | 200 | 0.041 | 0.051 | 1 | 80 |
| SUCROSE | 0 | 0 | 0.055 | 1.432 | 3 | 100 |
|  | 1.20 | 12.5 | 0.056 | 0.099 | 3 | 90 |
|  | 2.40 | 25 | 0.059 | 0.142 | 1 | 90 |
|  | 4.70 | 50 | 0.051 | 0.105 | 1 | 80 |
|  | 9.50 | 100 | 0.047 | 0.058 | 1 | 80 |
|  | 18.90 | 200 | 0.042 | 0.039 | 1 | 85 |
| TREHALOSE | 0 | 0 | 0.061 | 1.294 | 3 | 100 |
|  | 0.60 | 12.5 | 0.057 | 0.827 | 3 | 100 |
|  | 1.30 | 25 | 0.054 | 0.414 | 4 | 100 |
|  | 2.60 | 50 | 0.055 | 0.097 | 2 | 100 |
|  | 5.10 | 100 | 0.049 | 0.164 | 1 | 100 |
|  | 10.20 | 200 | 0.048 | 0.113 | 1 | 100 |
| RAFFINOSE | 0 | 0 | 0.056 | 1.432 | 3 | 100 |
|  | 0.40 | 12.5 | 0.060 | 0.192 | 3 | 100 |
|  | 0.70 | 25 | 0.058 | 0.138 | 4 | 100 |
|  | 1.40 | 50 | 0.062 | 0.085 | 6 | 90 |
|  | 2.90 | 100 | 0.063 | 0.201 | 1 | 90 |
|  | 5.90 | 200 | 0.070 | 0.154 | 1 | 90 |

Summary of initial values, gel quality, maximum rate and lag time for the poly-ols tested.

Discussion

These results are shown in FIG. 18, and demonstrate a marked and potent effect of poly-ols (sugar alcohols) on the coagulation profile of fibrinogen. In general, the absorbance of the gel structure is seen to be reduced to under 0.5 Au by 1% wt/vol of polyol, although the kinetic profile of the coagulation estimated by the $t_{50}$ (time to reach 50% of final OD) is very little effected. Glycerol was slightly exceptional in giving some delay in $t_{50}$. Particularly, the lower turbidity of resultant gels with poly-ols implies a finer, more diffuse distribution of fibrin fibres. Importantly the qualitative assessment of gel strength and integrity at the end of the coagulation period shows a general trend to a weaker gel with increasing concentration of poly-ol, particularly at 5% or more. The distinct exception was trehalose, which did not

| | | VOLUME (μl) | | | | | |
|---|---|---|---|---|---|---|---|
| REAGENT | CONCENTRATION | CONTROL | A | B | C | D | E |
| CaCl2 | 1M | 2.7 | 2.7 | 2.7 | 2.7 | 2.7 | 2.7 |
| BFbg | 2% | 500 | 500 | 500 | 500 | 500 | 500 |
| Sugar | 20% | 0 | 6.25 | 12.5 | 25 | 100 | 200 |
| MES/NaCl | 25/150 mM | 448 | 442 | 438 | 423 | 398 | 348 |
| Thrombin | 10 U/ml | 50 | 50 | 50 | 50 | 50 | 50 |

Summary of reagents, concentrations and volumes added in the coagulation assays.

reduce resultant gel integrity over the entire concentration range tested, up to 10%.

Although this difference in this assay is not large, it does demonstrate a possible advantage of trehalose over the other poly-ols. One caveat of this assay is the qualitative assessment of gel strength and integrity, which was based on assessment of the gel resistance to manual disruption with a blunt probe. This was clearly important to determine, since without assessing this at all, the false conclusion could be reached that the lower absorption profiles with poly-ols is indicative of inhibition of coagulation. This also raises a second caveat, concerning the turbidimetric assay method. This method is widely used, and forms the basis of many commercial coagulometers, but is an indirect assay of enzymatic fibrinogen coagulation, since it is measuring the light scattering of the insoluble product of that reaction. Clearly any differences in the micro-scale organisation of fibrin product will profoundly influence the turbidity profile. Therefore the exact nature of the difference between the structure of control gels, which are turbid, and more transparent gels formed in the presence of poly-ols, should be investigated. The molecular mechanism of the poly-ol effect has not been determined, but it is hypothesised that hydrogen-bond or strong dipole intermolecular interactions between these small poly-ols and the surface influences the higher order organisation of fibrin protofibril and fibril formation. This would be similar to the stabilising effect of poly-ols for proteins in solution.

Despite this, the data provides a useful reference for the effects of these poly-ol molecules on the relatively simple fibrinogen thrombin coagulation system, in the absence of a large molecule bulking agent such as alginate.

Coagulation Results
Effect of Poly-Hydroxyl Molecules as Stabilising Agents on Coagulation (II): Fibrinogen/Alginate Mixture
Aim In this second set, the effect of poly-ols as potential stabilising agents, on the solubility and enzymatic coagulation of mixed fibrinogen and alginate solutions, at concentration used in scaffold manufacture, is evaluated. As previously, stability and coagulation was measured by turbidity at 425 nm. The poly-ols tested were glycerol, sorbitol, glucose, sucrose, trehalose and raffinose.

Method

A 1M $CaCl_2$ solution was freshly prepared and filtered through a 0.2 μm filter before use. Autoclaved MES/NaCl buffer (25 mM MES, 150 mM NaCl pH 7.4) was used to dissolve fibrinogen, alginate and as a diluent. Bovine fibrinogen (bFbg) solution (2%) and alginate solution (4%) were made up in MES/NaCl buffer and the pH was adjusted to 7.4. Thrombin solution was 10 U/ml in 25 mM HEPES, 150 mM NaCl, pH 7.4, aliquoted and stored at −80EC. Glycerol was used directly. Test sugars were dissolved in $diH_2O$ at approximately saturation at 37EC (% wt/vol of each was recorded) and tested at 2.5, 5 and 10% wt/vol final concentration in the assay.

$CaCl_2$, bFbg, MES/NaCl and test sugar were added sequentially into a disposable plastic semi-micro cuvette and mixed thoroughly. The initial OD at 425 nm was recorded. Then thrombin was added, and immediately mixed to initiate coagulation and the OD was recorded every minute for 20 min or until coagulation was complete. The total assay volume was 1 ml.

At the end of the assay, the gel quality was manually assessed by comparing each test to the control.

Maximum rate and lag time were calculated for each test.

| REAGENT | STOCK SOLN CONCENTRATION | VOLUME (μl) | | | |
|---|---|---|---|---|---|
| | | CONTROL | 2.5% | 5% | 10% |
| CaCl2 | 1M | 2.7 | 2.7 | 2.7 | 2.7 |
| BFbg | 2% | 500 | 500 | 500 | 500 |
| Sugars | various | 0 | $x_{2.5}$ | $x_5$ | $x_{10}$ |
| Alginate | 4% | 250 | 250 | 250 | 250 |
| MES/NaCl | 25/150 mM | 197.3 | 197.3 − $x_{2.5}$ | 197.3 − $x_5$ | 197.3 − $x_{10}$ |
| Thrombin | 10 U/ml | 50 | 50 | 50 | 50 |

Summary of reagents, concentrations and volumes added in the coagulation assays.

Results
Summary of Stability & Coagulation Assay Data.
Table below summarises the results for all the sugars in the presence of fibrinogen and alginate:

| SUGARS | % | vol stock x (μl) | INTIAL OD ($A_{425}$) | MAX RATE (OD/min) | LAG TIME (min) | GEL % |
|---|---|---|---|---|---|---|
| GLYCEROL | 0 | 0 | 0.149 | 2.018 | 1 | 100 |
| | 2.50 | 25 | 0.280 | 0.871 | 3 | 90 |
| | 5 | 50 | 0.283 | 1.509 | 3 | 80 |
| | 10 | 100 | 0.167 | 0.067 | 0 | 80 |
| SORBITOL | 0 | 0 | 0.145 | 1.627 | 1 | 100 |
| | 2.50 | 28.75 | 0.450 | 1.175 | 1 | 90 |
| | 5 | 57.5 | 0.381 | 1.664 | 2 | 90 |
| | 10 | 115 | 0.373 | 1.597 | 2 | 80 |
| GLUCOSE | 0 | 0 | 0.139 | 1.948 | 1 | 100 |
| | 2.50 | 27.7 | 0.254 | 2.053 | 3 | 90 |
| | 5 | 55.55 | 0.254 | 2.422 | 4 | 90 |
| | 10 | 111.11 | 0.229 | 1.762 | 5 | 90 |
| SUCROSE | 0 | 0 | 0.145 | 1.692 | 1 | 100 |
| | 2.50 | 26.50 | 0.448 | 1.343 | 1 | 100 |
| | 5 | 53 | 0.577 | 1.488 | 2 | 90 |
| | 10 | 106 | 0.376 | 1.477 | 3 | 100 |
| TREHALOSE | 0 | 0 | 0.145 | 1.875 | 1 | 100 |
| | 2.50 | 48.75 | 0.150 | 1.473 | 1 | 100 |
| | 5 | 97.5 | 0.210 | 1.500 | 2 | 100 |
| | 10 | 195 | 0.195 | 1.450 | 3 | 120 |
| RAFFINOSE | 0 | 0 | 0.145 | 1.754 | 1 | 100 |
| | 2.50 | 85 | 0.189 | 1.511 | 1 | 80 |
| | 5 | 170 | 0.170 | 1.806 | 2 | 80 |

Discussion

These results relate to similar companion data set derived from a simpler assay mixture, in which alginate was not included. The present results are shown in FIG. 19, and demonstrate that the introduction of alginate into the assay mixture changes the nature of the effect of poly-ols. The primary interest in the effect of these poly-ols is as potential stabilising agents of the soluble fibrinogen, prior to coagulation. In these experiments it can be seen that the pre-thrombin OD values 0.1-0.2, whereas without alginate they typically 0.05-0.1. Without alginate, the poly-ols tested had little effect on pre-coagulation turbidity, which is an index of protein aggregation and precipitation. However, in the presence of alginate, most of the poly-ols tested actually increased baseline turbidity, and thus do not demonstrate the desired stabilisation effect. However, trehalose and raffinose caused little or no increase in baseline turbidity.

Whereas without alginate, poly-ol addition results in formation of a clear gel, in the presence of alginate, their effect is different. They instead delay the onset of coagulation without a marked effect on the final turbidity of the product. The potency of these effects is more varied with alginate than without (glycerol and glucose show a marked inhibition of coagulation at 5% wt/vol, whereas sorbitol, sucrose and trehalose have noticeable delay only at 10%).

Importantly, as found in the absence of alginate, qualitative assessment of gel strength and integrity at the end of the coagulation period shows a general trend to a weaker gel with increasing concentration of poly-ol, even as low as 2.5% wt/vol. Trehalose and sucrose were distinct exceptions, which did not reduce resultant gel integrity over the entire concentration range tested, and trehalose even improved the strength at 10% wt/vol.

(The baseline turbidity is temperature sensitive, being greater towards 0° C. and reduced by warming to 37° C. This is also true for the effect of poly-ols in the mixtures).

The results of this data set show that poly-ols and alginate have an interacting effect on fibrinogen coagulation. Most of the poly-ols tested increased the pre-coagulation turbidity of the fibrinogen alginate solution, which is undesirable. Of those tested only trehalose and raffinose are possibly acceptable by this parameter. Also generally, poly-ols in the presence of alginate delay the onset of coagulation. This effect was more variable, but suggests that glycerol and glucose are least useful on this criterion. The result gel strength is another important parameter. Interestingly, sucrose had little effect on this, which suggests potential suitability, but trehalose has no detectable negative effect and even slightly increases the gel strength at 10%. Interestingly, raffinose weakens the gel, making it less suitable on this criterion. Since sucrose is seen to have a less desirable effect on fibrinogen solubility, trehalose emerges as an interesting candidate molecule.

This data is important to appreciate the effect of poly-ol addition to a yet more complex mixture, when a surfactant is added. The mixture of fibrinogen and alginate is relatively stable, as demonstrated in this data set by an absorbance around 0.15 AU against water. 2% Fibrinogen in pH7.4 buffered saline (eg HEPES/NaCl or MES/NaCl) is typically slightly turbid but usually less than 0.1 AU. However, addition of surfactant together with alginate typically increases turbidity, indicative of fibrinogen precipitation. Moreover, turbidity of fibrinogen solutions is found to vary, and a relationship between the turbidity of the starting solution and the extent of the increase upon mixing with alginate may exist. Earlier experiments in the combined presence of alginate and surfactant identified a benefit of poly-ols, especially trehalose, in stabilising or slightly increasing basal fibrinogen solubility (i.e. maintaining or reducing turbidity of such mixtures).

As with the simpler assay system of just fibrinogen and poly-ol interaction, this data set demonstrates an advantage of trehalose over the other poly-ols. The reason for the different effect on gel formation of the poly-ols in the presence of alginate is not known, but it is hypothesised that an interaction between fibrin fibres and alginate, reflects the bulking effect of the alginate, dominates over the effect of poly-ol dispersion of fibrin fibres. These results collectively allow a conclusion that it is possible to use a selective stabilising effect of small poly-ol molecules in the complex macromolecular mixture of fibrinogen protein, a polysaccharide such as alginate, and a surfactant. Trehalose emerges as a molecule with a particularly useful combination of effects in such a mixture.

Coagulation Results

Effect of Poly-Hydroxyl Molecules as Stabilising Agents on Coagulation (III): Fibrinogen/Alginate/SMOF2 Mixture.

Aim

The previous two companion studies characterised the effects of poly-ols on the coagulation of fibrinogen and fibrinogen plus alginate solutions, under conditions similar to those used for manufacture of porous fibrin scaffolds. However, the actual scaffold manufacture mixture includes a surfactant, in addition to fibrinogen and alginate. A particular surfactant mixture used in SMOF2 has been previously found to be particularly effective at producing a porous fibrin scaffold structure. In this third set the effect of the most useful poly-ols from these previous results as potential stabilising agents are evaluated in this more complex coagulation mixture. As in the previous assays, effects on the pre-coagulation solubility, the kinetics of enzymatic coagulation, and the final gel product are required to make a full assessment. The poly-ols selected were the sugars, sucrose, trehalose and raffinose.

Method

A 1M $CaCl_2$ solution was freshly prepared and filtered through a 0.2 µm filter before use. Autoclaved MES/NaCl buffer (25 mM MES, 150 mM NaCl pH 7.4) was used to dissolve fibrinogen, alginate and as a diluent. Bovine fibrinogen (bFbg) solution (2%) and alginate solution (4%) were made up in MES/NaCl buffer and the pH was adjusted to 7.4. Thrombin solution was 10 U/ml in 25 mM HEPES, 150 mM NaCl, pH 7.4, aliquoted and stored at −80EC. SMOF-2 was a mixture of several surfactants: DMP 8%, ODM4%, DdGP4%, Pluronic F68 4% (total surfactant concentration 20%). Test sugars were dissolved in $diH_2O$ at approximately saturation at 37EC (% wt/vol of each was recorded) and tested at 2.5, 5 and 10% wt/vol final concentration in the assay.

$CaCl_2$, bFbg, MES/NaCl and test sugar were added sequentially into a disposable plastic semi-micro cuvette and mixed thoroughly. The initial OD at 425 nm was recorded. Then thrombin was added, and immediately mixed to initiate coagulation and the OD was recorded every minute for 20 min or until coagulation was complete. The total assay volume was 1 ml.

At the end of the assay, the gel quality was manually assessed by comparing each test to the control.

Maximum rate and lag time were calculated for each test.

| | STOCK SOLN | VOLUME (µl) | | | | | |
|---|---|---|---|---|---|---|---|
| REAGENT | CONCENTRATION | CONT | SMOF2 | sugar | 2.5% | 5% | 10% |
| CaCl2 | 1M | 2.7 | 2.7 | 2.7 | 2.7 | 2.7 | 2.7 |
| BFbg | 2% | 500 | 500 | 500 | 500 | 500 | 500 |
| Sugars | various | 0 | 0 | $x_{10}$ | $x_{2.5}$ | $x_5$ | $x_{10}$ |
| Alginate | 4% | 250 | 250 | 250 | 250 | 250 | 250 |

| | STOCK SOLN | VOLUME (µl) | | | | | |
|---|---|---|---|---|---|---|---|
| REAGENT | CONCENTRATION | CONT | SMOF2 | sugar | 2.5% | 5% | 10% |
| SMOF2 Mix | 20% | 0 | 50 | 0 | 50 | 50 | 50 |
| MES/NaCl | 25/150 mM | 197.3 | 147.3 | 197.3-$x_{10}$ | 147.3-$x_{2.5}$ | 147.3-$x_5$ | 147.3-$x_{10}$ |
| Thrombin | 10 U/ml | 50 | 50 | 50 | 50 | 50 | 50 |

Summary of reagents, concentrations and volumes added in the coagulation assays.
Results
Summary of Stability & Coagulation Assay Data.

| SUGARS | % | vol stock x (µl) | INTIAL OD ($A_{425}$) | MAX RATE (OD/min) | LAG TIME (min) | GEL % |
|---|---|---|---|---|---|---|
| SUCROSE | CONT | 0 | 0.281 | 1.64 | 1 | 100 |
| | SMOF2 | 0 | 0.285 | 1.42 | 1 | 100 |
| | 10% | 106 | 0.263 | 1.82 | 4 | 90 |
| | SMOF2 + 2.5% | 26.5 | 0.264 | 1.71 | 2 | 90 |
| | SMOF2 + 5% | 53 | 0.258 | 1.31 | 3 | 80 |
| | SMOF2 + 10% | 106 | 0.255 | 1.90 | 4 | 70 |
| TREHALOSE | 0 | 0 | 0.287 | 1.70 | 1 | 100 |
| | SMOF2 | 0 | 0.303 | 1.52 | 1 | 100 |
| | 10% | 195 | 0.22 | 1.95 | 4 | 100 |
| | SMOF2 + 2.5% | 48.8 | 0.27 | 1.61 | 2 | 100 |
| | SMOF2 + 5% | 97.5 | 0.246 | 1.69 | 2 | 90 |
| | SMOF2 + 10% | 195 | 0.217 | 1.47 | 4 | 110 |
| RAFFINOSE | 0 | 0 | 0.206 | 1.538 | 1 | 100 |
| | SMOF2 | 0 | 0.222 | 1.175 | 1 | 100 |
| | 5% | 170 | 0.234 | 0.157 | 4 | 40 |
| | SMOF2 + 2.5% | 85 | 0.267 | 1.487 | 2 | 60 |
| | SMOF2 + 5% | 170 | 0.266 | 1.595 | 2 | 50 |

Summary of initial values, gel quality, maximum rate and lag time for the sugars tested in the presence of fibrinogen, alginate and the SMOF2 surfactant mixture.

Discussion

Figure 20A:
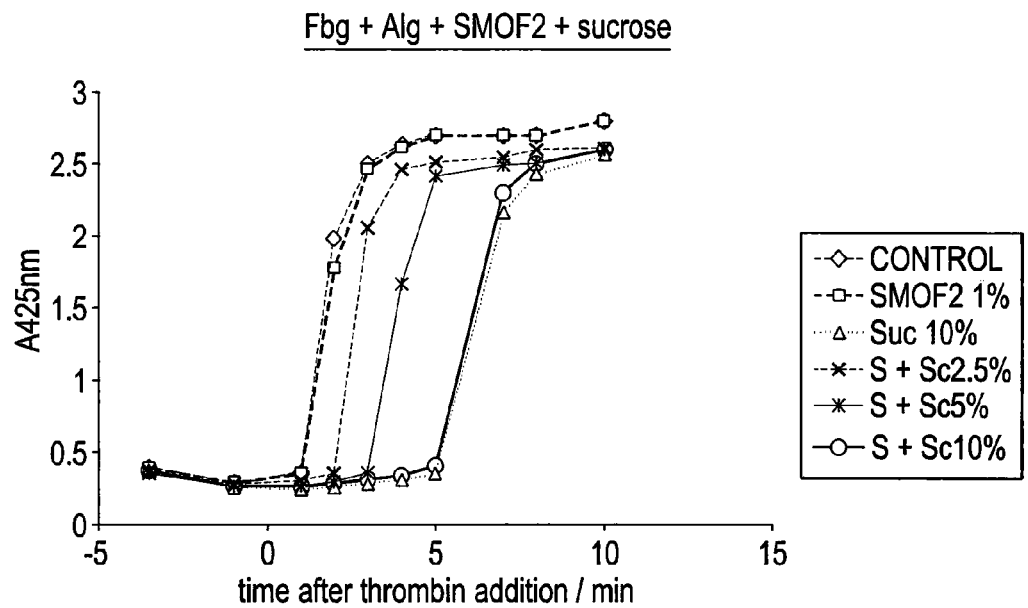
Figure 20B:
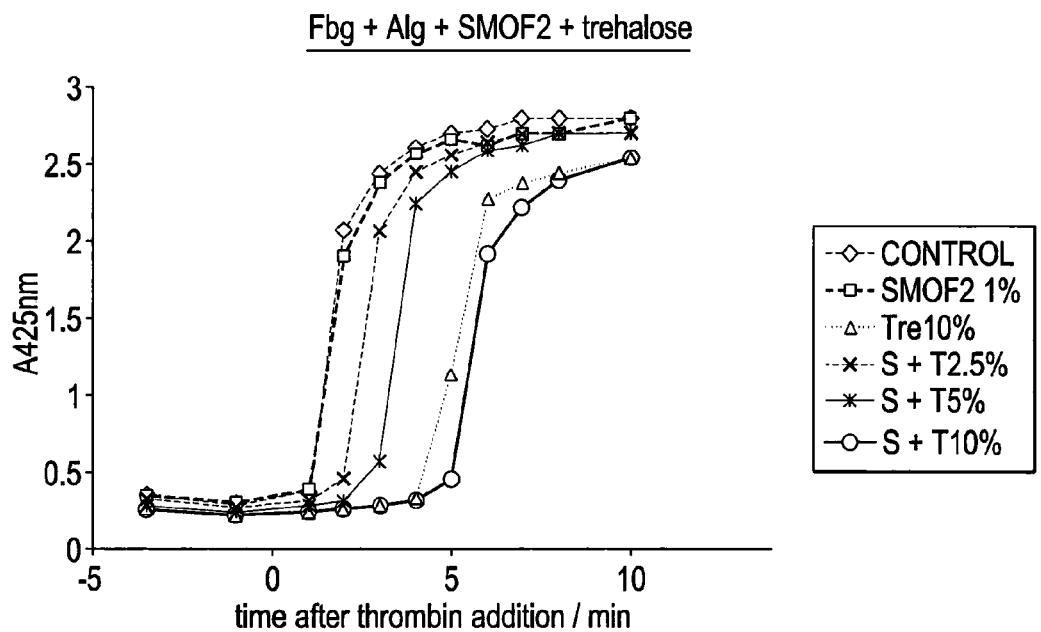
Figure 20C:
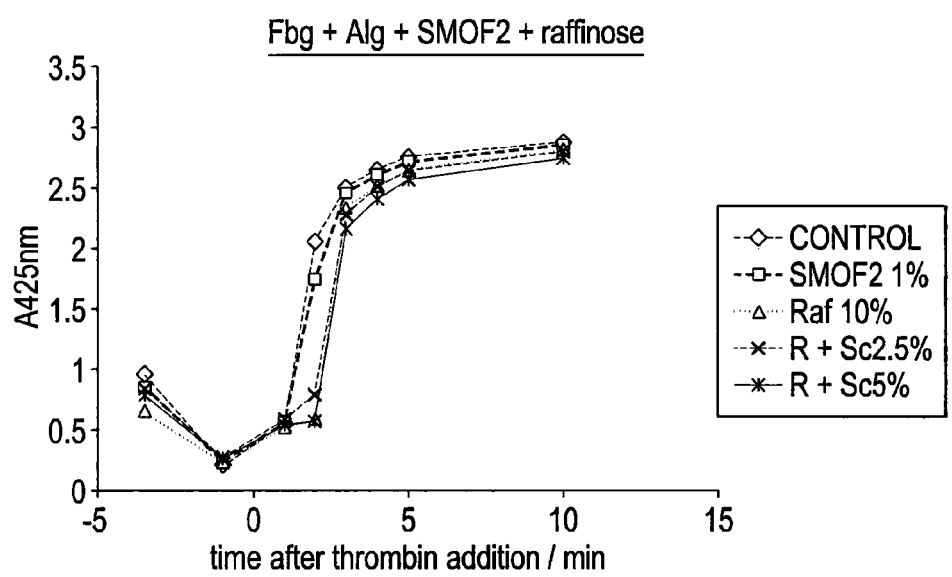

These results relate to the previous companion data sets derived from simpler assay mixtures, in which the effect of poly-ols on fibrinogen, or fibrinogen plus alginate was studied. These results are shown in FIG. 20, and indicate that the most useful poly-ols for the present study to be sucrose, trehalose and raffinose. The present results demonstrate that the addition surfactant mix SMOF2 increases the initial precipitation of the fibrinogen alginate solution, but has little effect on the coagulation kinetics. The effect of the candidate sugars is to influence the solution stability, delay the onset of coagulation and influence the strength and integrity of the resultant gel.

Of the candidate poly-ols, the sugar, sucrose, was selected on the basis of have little impact on the resultant gel strength of fibrinogen alginate. However, with the inclusion of surfactant into the coagulation mixture, sucrose did not confer any benefit. It had very little effect on the pre-coagulation turbidity of the solution, inhibited the onset of coagulation and reduced the gel strength and integrity. Raffinose gave rather similar result. Although it did show some initial stabilisation of the solution mixture, this differential effect was not maintained during the pre-coagulation incubation. It also showed a typical inhibition of coagulation onset. However, it caused a substantial weakening of the resultant gel, which is clearly undesirable.

As in the simpler assay systems, this data set demonstrates an advantage of trehalose in this coagulation mixture. It has a marked effect of lowering pre-coagulation turbidity in complex mixtures, together with the forming of a gel with at least the strength and integrity of controls. The previously identified caveat of this assay being the qualitative nature of the gel strength and integrity assessment is important. However, this limited evidence indicates that different sugars influence gel strength, and that trehalose is not deleterious to gellation, and may improve it.

These results collectively demonstrate the possibility of obtaining a selective stabilising effect of particular sugars and other small poly-ol molecules in the complex macromolecular mixture of fibrinogen protein, a polysaccharide such as alginate, and a surfactant. Trehalose emerges as a molecule with a particularly useful combination of effects in such a mixture.

Porosity & Pore Size Measurements

Aim

It is important to be able to measure parameters which relate to the principle structural characteristics of cross-linked fibrin scaffolds. The porosity characteristics of fibrin-based scaffolds are important for defining a manufactured material as well as for determining the biological function.

The porosity (volume per unit mass of scaffold protein) gives a useful parameter which is easily determined. The microscopic pore diameter is derived by measuring widest diameter across an internal void space. Although these parameters do not measure the microstructure, they are valid descriptors which can contribute to defining the characteristic of the material.

Methods

The scaffolds in this characterisation study were prepared using the close-to-optimal formula and method determined on the basis of physical characteristics, and results of evaluation of in vitro and in vivo bio-interactions. Particularly, the scaffolds have a close-to-homogeneous structure through the depth of the material, as determined by microscopic inspection of microtome sections. These scaffolds were manufactured using the formulation termed SM-OF1, SM-OF2 and DdSuc (in which a single surfactant, n-dodecylsucrose, is used in place of a mixture). Scaffolds in the last step of the manufacture process were washed 5 times in deionised water, then they were prepared for lyophilisation to yield a dry product, by either of the following methods.

(i) Scaffolds (SM-OF1) were soaked for 30 minutes in sorbitol 1M, as a lyophilisation excipient, drained and frozen at −80° C. for at least 2 hours, then lyophilised in a bench-top freeze drier for 16-24 hr.

(ii) Scaffolds were drained after the last wash in de-ionised water (diH2O) and transferred into a controllable pilot scale lyophiliser. A programmed lyophilisation sequence was used in which samples were frozen down to −40° C. and maintained at this temperature for the drying period (36 hr) at 100 mtor.

Yield

A yield parameter is calculated by the ratio of mass of fibrinogen plus alginate used to mass of product.

Porosity

Porosity was measured macroscopically by recording the weight and linear dimension of the product, to derive porosity=volume/mass.

Pore Size

Samples of scaffold were cut from the product using a scalpel, and processed in a Miles Scientific Tissue-Tek histological tissue processor by fixation in 10% formaldehyde, and embedding in paraffin wax. Sections were cut using a microtome set at 4 um. Sections were adhered onto a slide, de-waxed and stained with 0.5% w/v Eosin Y aqueous solution, followed by dehydration and mounting in DPX.

Sections were photographed at 10× (Axioskop microscope with achroplan 10×/0.25 lens, Zeiss, Watford UK) and DC200 digital camera with IM50 Image Manager software (Leica, Milton Keynes, UK). The images were electronically stitched using Microsoft ICE software. Pore diameter measurements from these montages were measured using image J (version 1.43u/Wayne Rasband, National Institute of Health, USA) calibrated using a stage graticule.

Figure 21:
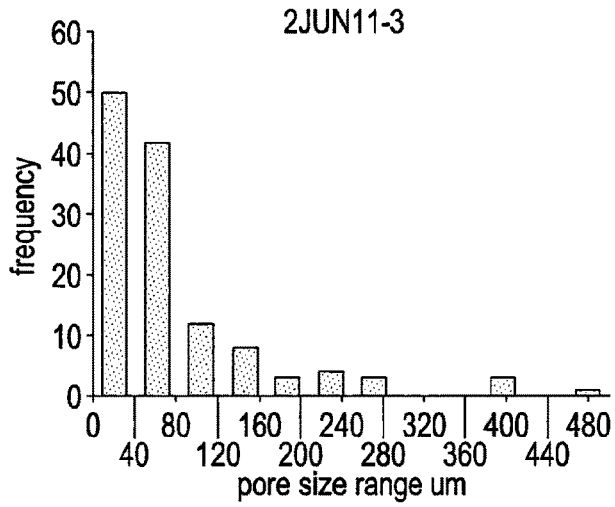
FIG. 21. Porosity and Pore Size results.
Figure 21:
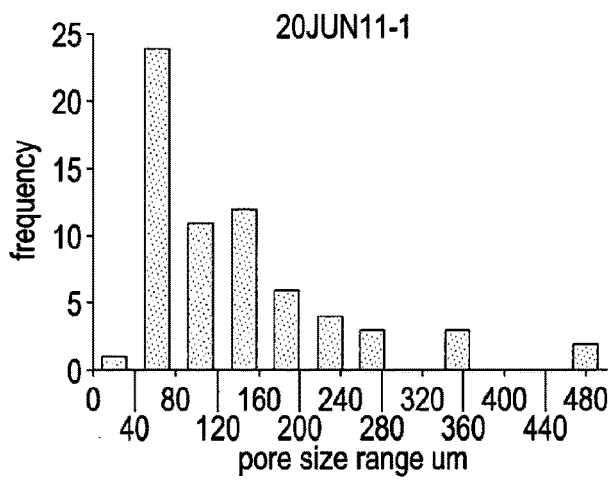
Figure 21:
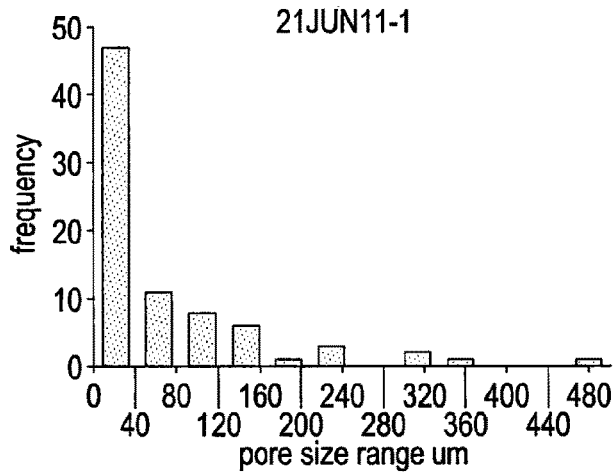
Figure 21:
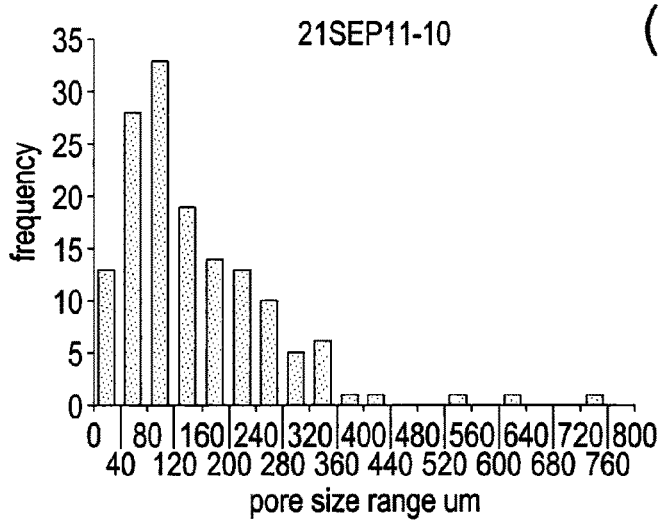
Figure 21:
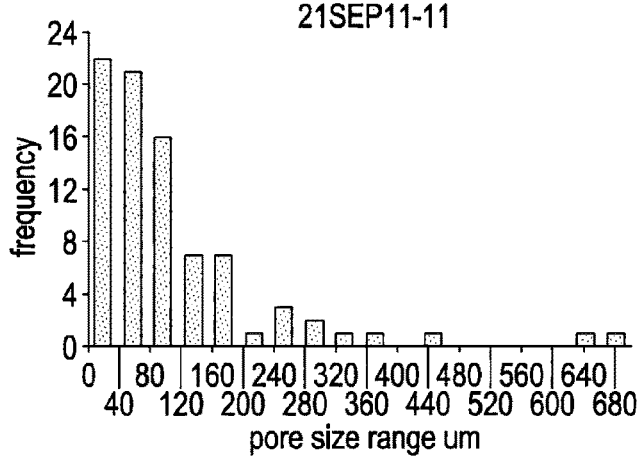
Figure 21:
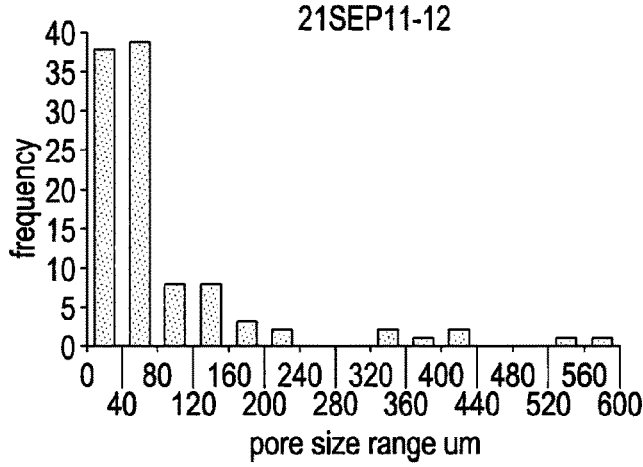
Figure 21:
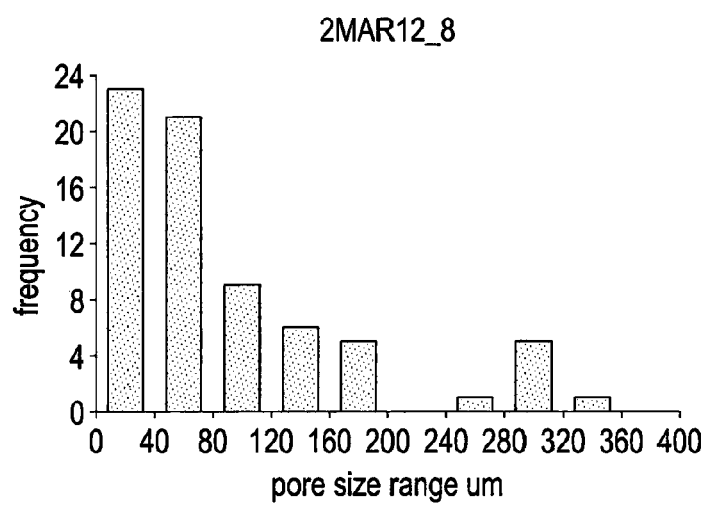

FIG. 21—Porosity and Pore Size results.

Results

| Scaffold formulation | Batch ID | Median pore diameter (μm) | Interquartile range (μm) |
|---|---|---|---|
| SM-OF1 | 2JUN11_3 | 53.1 | 32.3-93.0 |
|  | 20JUN11_1 | 123.2 | 72.1-197.2 |
|  | 21JUN11_1 | 33.8 | 22.3-84.4 |
|  | Average | 70 | 42.2-124.9 |
| SM-OF2 | 21SEP11_10 | 116.3 | 72.8-203.5 |
|  | 21SEP11_11 | 75.0 | 30.1-127.2 |
|  | 21SEP11_12 | 47.8 | 29.1-87.9 |
|  | 2MAR12_1 | 154.7 | 77.7-208.9 |
|  | FEB2013 | 65.9 | 36.9-125.9 |
|  | Average | 75.2 | 41.3-134.8 |
| DdSuc | 8FEB12_13 | 144.8 | 94.2-214.8 |
|  | 15FEB12_7 | 69.3 | 41.6-125.5 |
|  | 2MAR12_8 | 58.2 | 34.6-117.9 |
|  | Average | 90.8 | 56.8-152.7 |

Product Pore Size Data for Scaffolds

Discussion

In the samples included in this study, the yield was relatively constant and the porosity values varied with SD 13% for the SMOF2 set and 39% for the DdSuc set. The least accurate measurement parameter in deriving porosity is sample height, and this variation is reflected by the pore size variation.

Much of the investigative studies performed on scaffolds during the development of the scaffold formulations used sorbitol as a freeze-dry excipient, to prevent shrinkage and cracking of scaffolds in the drying conditions obtained with a bench top freeze-drier. This procedure meant that process yield and porosity data could not be obtained directly. However, use of a controllable pilot-scale lyophiliser allowed production of product in conditions which avoided product shrinkage and cracking without the use of an excipient such as sorbitol.

An interesting feature of the quantitative pore size data is that variation occurs in the range and distribution of pore sizes, as well as in mean and median values. The variation between individual samples is larger than differences between formulations (SMOF1, SMOF2 or Ddsuc). The source of the variation within and between manufacture batches has not been determined. One explanation is that the range of pore sizes arises from two processes with opposing effects: (1) Mixing energy generates voids or bubbles, breaking large voids into smaller voids. (2) Coalescence of small voids or bubbles in the initial coagulum, into larger

| Scaffold formulation | Batch ID | Vol 2% Fbg (ml) | Vol 2% AA (ml) | Mass reagents (mg) | Mass sample (mg) | Yield % | L (cm) | W (cm) | H (cm) | Vol (ml) | Porosity vol/mass |
|---|---|---|---|---|---|---|---|---|---|---|---|
| SMOF-2 | 8FEB12_20 | 3 | 1.5 | 90 | 56.5 | 62.8 | 5 | 5.1 | 0.7 | 17.85 | 0.316 |
|  | 21SEP11_10 | 3 | 1.5 | 90 | 54.6 | 60.67 | 4.9 | 4.9 | 0.6 | 14.406 | 0.264 |
|  | 21SEP11_11 | 3 | 1.5 | 90 | 56.6 | 62.89 | 5 | 5 | 0.6 | 15 | 0.265 |
|  | 21SEP11_12 | 3 | 1.5 | 90 | 50.7 | 56.33 | 5 | 5 | 0.7 | 17.5 | 0.345 |
|  | 2MAR12_1 | 6 | 3 | 180 | 117.5 | 65.28 | 9 | 9 | 0.5 | 40.5 | 0.345 |
| AVERAGE |  |  |  |  |  | 61.6 |  |  |  |  | 0.307 |
| SD |  |  |  |  |  | 3.36 |  |  |  |  | 0.0406 |
| % SD |  |  |  |  |  | 5.46% |  |  |  |  | 13.2% |
| DdSuc | 8FEB12_13 | 3 | 1.5 | 90 | 52.1 | 57.89 | 5 | 5 | 0.4 | 10 | 0.192 |
|  | 8FEB12_14 | 3 | 1.5 | 90 | 55.1 | 61.22 | 4.8 | 4.9 | 0.4 | 9.408 | 0.171 |
|  | 2MAR12_8 | 6 | 3 | 180 | 102.8 | 57.11 | 9.3 | 9.3 | 0.4 | 34.596 | 0.337 |
| AVERAGE |  |  |  |  |  | 58.7 |  |  |  |  | 0.233 |
| SD |  |  |  |  |  | 2.18 |  |  |  |  | 0.0902 |
| % SD |  |  |  |  |  | 3.72% |  |  |  |  | 38.7% |

Product mass yield dimensions and porosity for scaffolds lyophilised without lyophilisation excipients.

voids with greater stability. This could be by diffusion, gravity, coagulation rate and the dehydrating effect of cross-linking reagent. Additional factors, variations in mixing, and particularly edge effects, might operate.

There is also a theoretical challenge in measuring an intrinsically disordered structure. Although the microscopic pore diameter is perhaps an attractive theoretical parameter, it has to be derived by measuring widest diameter across an internal void space. However the definition of a pore becomes complicated if the void in a material is disordered or complex and tortuous, as in these fibrin-based scaffolds. Pore interconnectivity even in a geometrically regular theoretic porous structure becomes challenging to measure.

It is also recognised that the fine structure of the fibrin-based scaffold is an important biological determinant, tantamount to the micro/nanoscale level of material porosity.

Thus, the invention provides an extracellular matrix composition wherein the cross-linked fibrinogen is essentially free of dense micro-aggregates, or plates, of precipitated protein.

The invention also provides an extracellular matrix composition wherein the distribution of pore sizes in the cross-linked fibrinogen is in the following range:
(i) 25% quartile range=from 20 to 75 micron;
(ii) median range=from 30 to 125 micron;
(iii) 75% quartile range=from 50 to 200 micron.

The invention also provides an extracellular matrix composition wherein the bulk porosity of the cross-linked fibrinogen is in the range 0.08 to 0.4 ml/mg lyophilised product.

The invention also provides an extracellular matrix composition wherein both the distribution of pore sizes in the cross-linked fibrinogen and the bulk porosity are as stated above.

Comparison of Smart Matrix with Matriderm
Summary
Cell scaffolds can play a significant role in dermal reconstruction to improve the reconstruction of skin, reduce the rate of complications, accelerate recovery and prevent scar hypertrophy.

A major problem of current commercial biomaterial scaffolds for dermal reconstruction is that their rate of integration and vascularisation is relatively slow.

Smart Matrix aims to increase the growth of blood capillaries into the scaffold, accelerate the rate of integration, and promote a regenerative healing response. The overall benefits will be to reduce the complications and the time for wound healing.

Matriderm is a biomaterial based on collagen, and incorporates elastin, which is not cross-link stabilised (unlike Integra). We have found that Matriderm is largely resorbed within the first week of application to a wound. It is resorbed rapidly (although in some experimental wounds we have observed that the thicker collagen fibres can be retained). This appears to correlate with the successful integration of split thickness skin graft single stage over-grafts. As such, its function seems better described as a biological wound dressing rather more than as a tissue scaffold.

The experimental methods currently available to evaluate materials for scarring have important limitations. Scarring is a long-term response which is a particular response of healing in humans, distinct from almost all animal species. Currently, there are no readily available experimental models which predict whether a biomaterial will cause scarring in human subjects.

We have found that the integration responses to current commercial materials in a porcine wound model are similar to that found clinically in human subjects, and thus broadly predicative of the early phases. This has enabled a robust comparison and differentiation between Smart Matrix and Integra. We have important evidence that Smart Matrix does not cause a scar-like long-term healing response, in direct parallel comparisons with these current commercial materials.

The function of Smart Matrix is distinct from both Integra and Matriderm. However, in the case of Matriderm, which resorbs rapidly, it has not been possible to distinguish differences in the success of a single-stage skin reconstruction using split-thickness skin graft overlay onto either Matriderm or Smart Matrix, in a healthy porcine wound model. Differences in the histological process of tissue reorganisation are apparent in a direct comparisons of the two materials.

Figure 22:
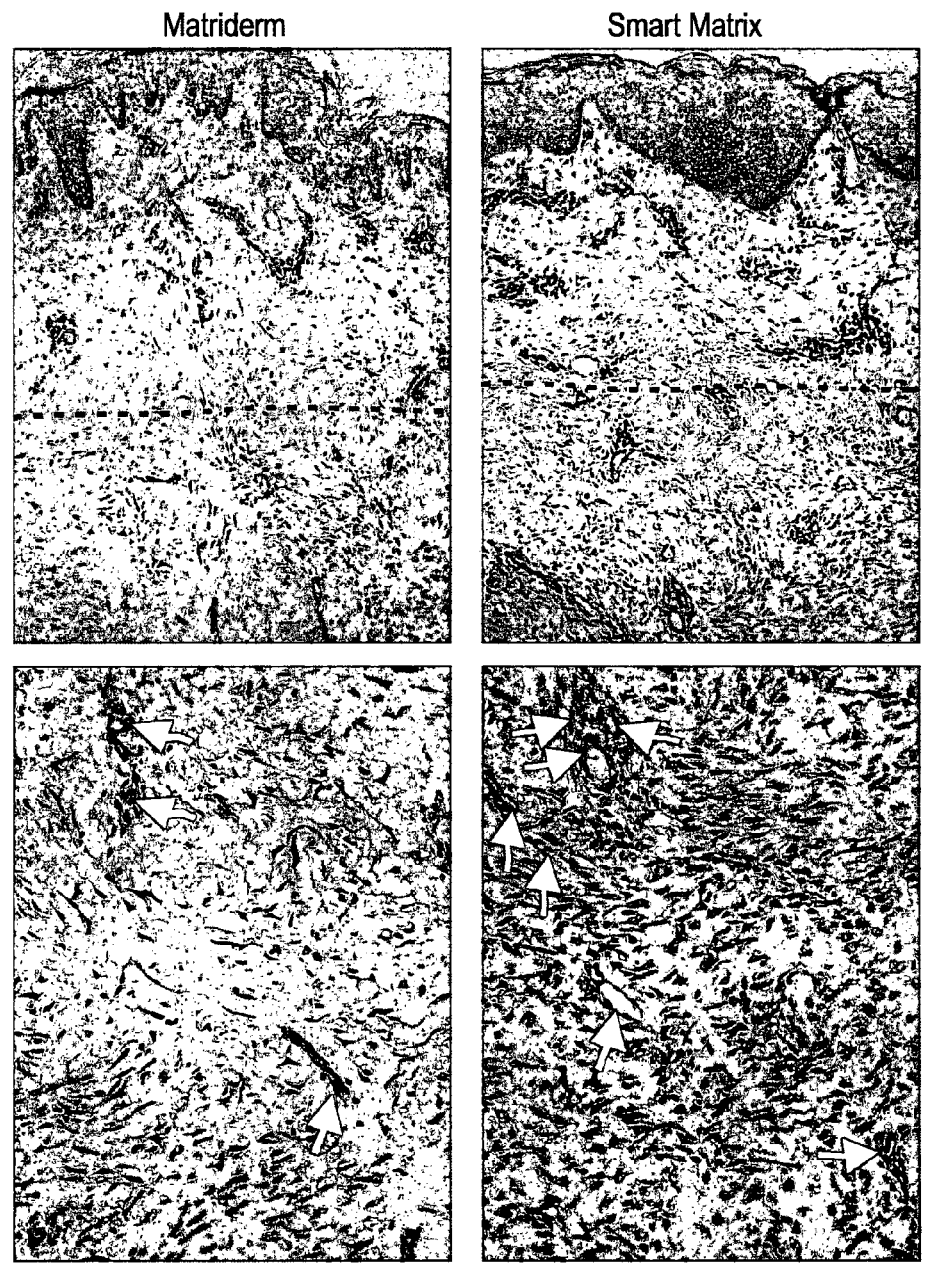
FIG. 22. Comparison of Smart Matrix with Matridenn.
Figure 22:
Figure 22:
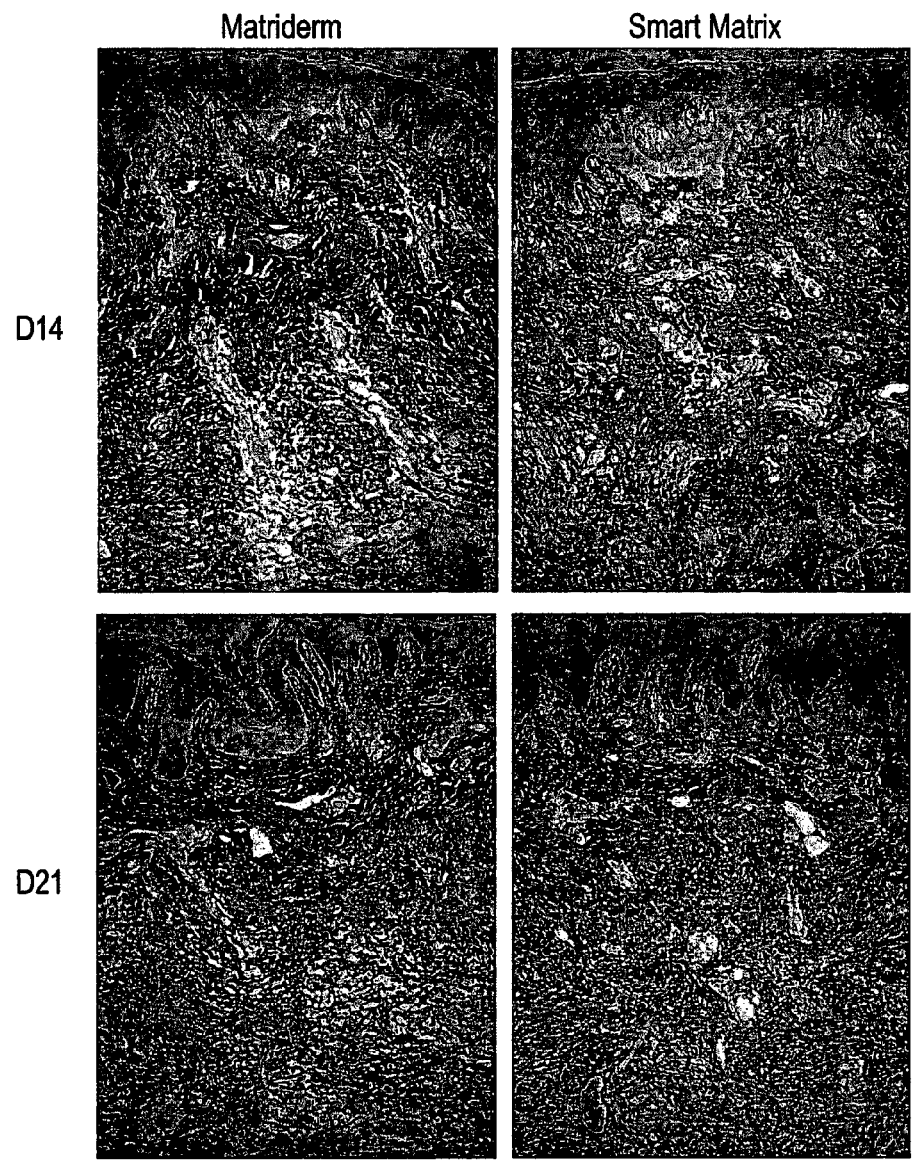

FIG. 22A shows the outcome of a split-thickness skin graft overlaid onto either Matriderm or Smart Matrix, after three weeks. Visual differences in the density of (Fibroblast) cells and blood capillaries are apparent. The figure shows the histological outcome of single stage reconstructions with Smart Matrix and Matriderm and STSG overlay at Day 21 (two parallel wounds in the same animal). Upper panels show the STSG interface with the new dermis (dashed lines show approximate base of the STSG). Lower panels show the dermal tissue at higher magnification (arrows show blood capillaries formed in the new dermis).

FIG. 22B shows the scaffold function of Smart Matrix is still present at week 3, although much of the structure has been resorbed, the scaffold remains dispersed as a residual framework within the new dermal tissue which has grown through it. Smart Matrix scaffold is fully infiltrated with fibroblasts and blood capillaries. The histology shows the resorption of the matrix at Day 21. Small arrows (black) show examples of areas of scaffold; large arrows (red) show blood capillary formation.

FIG. 22C shows differences in the pattern of collagen deposition, with a greater density of collagen in Smart Matrix wounds than Matriderm wounds. The functional significance of this has not been determined yet. It shows the histological outcome of single stage reconstructions with Smart Matrix and Matriderm and STSG overlay, at Days 14 and 21 (two parallel wounds in the same animal). Staining (red) marks fibrillar collagen, both pre-existing within the skin graft and newly deposited within the regenerating dermis. Dashed lines show approximate base of the STSG.

Mechanical Properties of Smart Matrix:
One of the current challenges in manufacturing fibrin based scaffolds is the fabrication of homogenous architectures. Although mechanically weak and structurally complex, the characterization of their mechanical properties may facilitate their manufacture and understanding their effects on cellular behavior.

We have evaluated the mechanical properties of fibrin/alginate-based scaffolds (Smart Matrix™) by incorporating variable amounts of a surfactant into the scaffolds.

Experimental Methods
Smart Matrix scaffolds were manufactured using varying the proportions of components including surfactant mix in order to create a series of 10 scaffolds, varying in porosity.

The collagen/elastin material Matriderm was used as a reference material.

SEM: Samples (0.5×1 cm) were washed, lyophilized and carbon coated (Belzer) for morphological characterization using routine SEM (FEI Inspect-F system).

Tensiometry:
a). 3×2 cm standard dumbbell shape samples were prepared from each specimen. Samples were loaded into the tensile machine (INSTROM 5565) tested to failure at the rate of 3 mm/min. Maximum elongation and ultimate tensile strength data were analyzed by ANOVA (Prism software).

b). 3×2 cm rectangular samples were prepared from each specimen. Samples were loaded into the Texture Analyser TA XTplus (Stable Microsystems, Godalming), with a 5 kg load cell tested to failure at the rate of 1 mm/s. The samples where cut to a size of 2×2.5 cm and the test size set to 2×2 cm. All samples where hydrated using Distilled water.

Rheology:

Dynamic viscoelasticty of Smart Matrix to deformation compared to the reference material was measured using a oscillation frequency ramp program (Bohlin CVO rheometer).

Results and Discussion

The scaffolds in this series of sequentially varying mixes were mostly seen to consist of a fine fibre mesh structure. Most formulations resulted in open pores on the micron scale (<250:). However, the relationship between scaffold formulation and resultant porosity was not simple or continuous. Rather, a porous structure was supported over a range of formulation variables, outside of which a denser structure was obtained.

The Smart Matrix material when hydrated is soft, extremely compliant and extendable. It also behaves as a non-classical elastic material under stress/strain analysis.

Figure 23A:
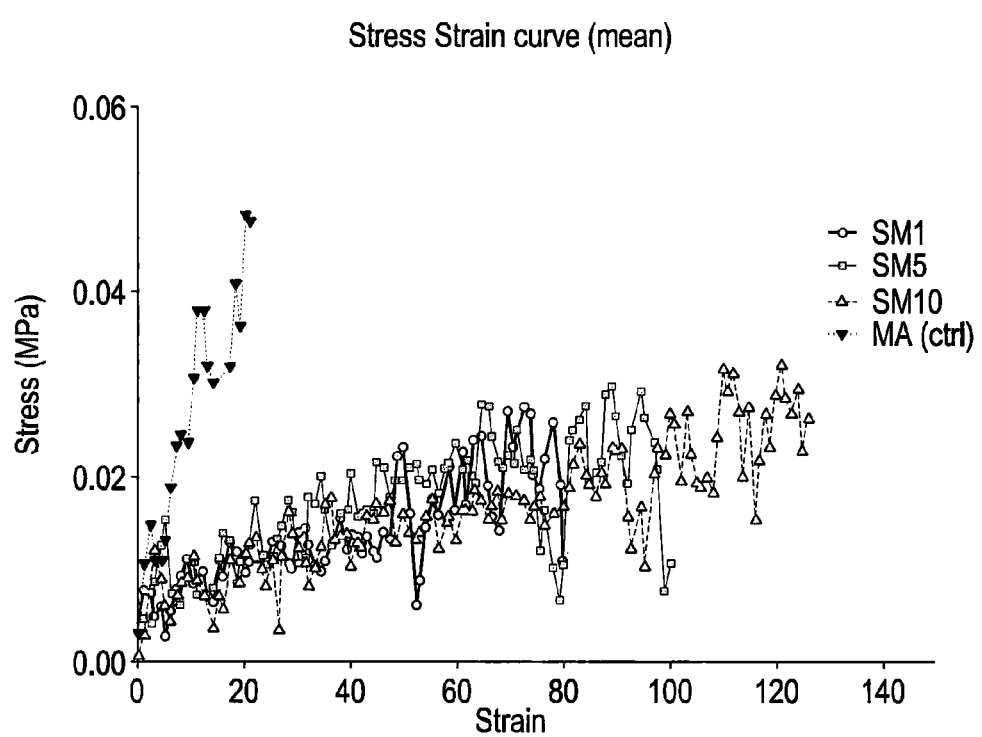
FIG. 23. Stress-Strain Curves for Smart Matrix SM-OF2 (4 batches), Matriderm and Integra.

Tensiometry measurements using an INSTROM 5565 were at the low end of the sensitivity range, and data obtained showed significant noise levels. At 3 mm/min rate, for standard dumbbell shaped samples, the ultimate tensile strength obtained of the series of scaffolds in the series (0.041±0.017) were all similar to the Matriderm (0.048±0.007) (MPa, MN±SEM, n=3). Interestingly, high porosity forms of Smart Matrix showed greater ultimate elongation values. FIG. 23a shows the analysis of three different Smart Matrix scaffold runs compared to Matriderm. The maximum elongation of the optimal structure for rapid integration on a full thickness wound in vivo reached approximately 100%, compared to around 30% for Matriderm. FIG. 23a shows Stress-strain curves for three Smart Matrix optimised formula 1 (SMOF #1) scaffold variants with different porosities compared to Matriderm. The surfact level used in the formulation was varied: SM 1—none; SM5—medium; SM10—high.

Figure 23B:
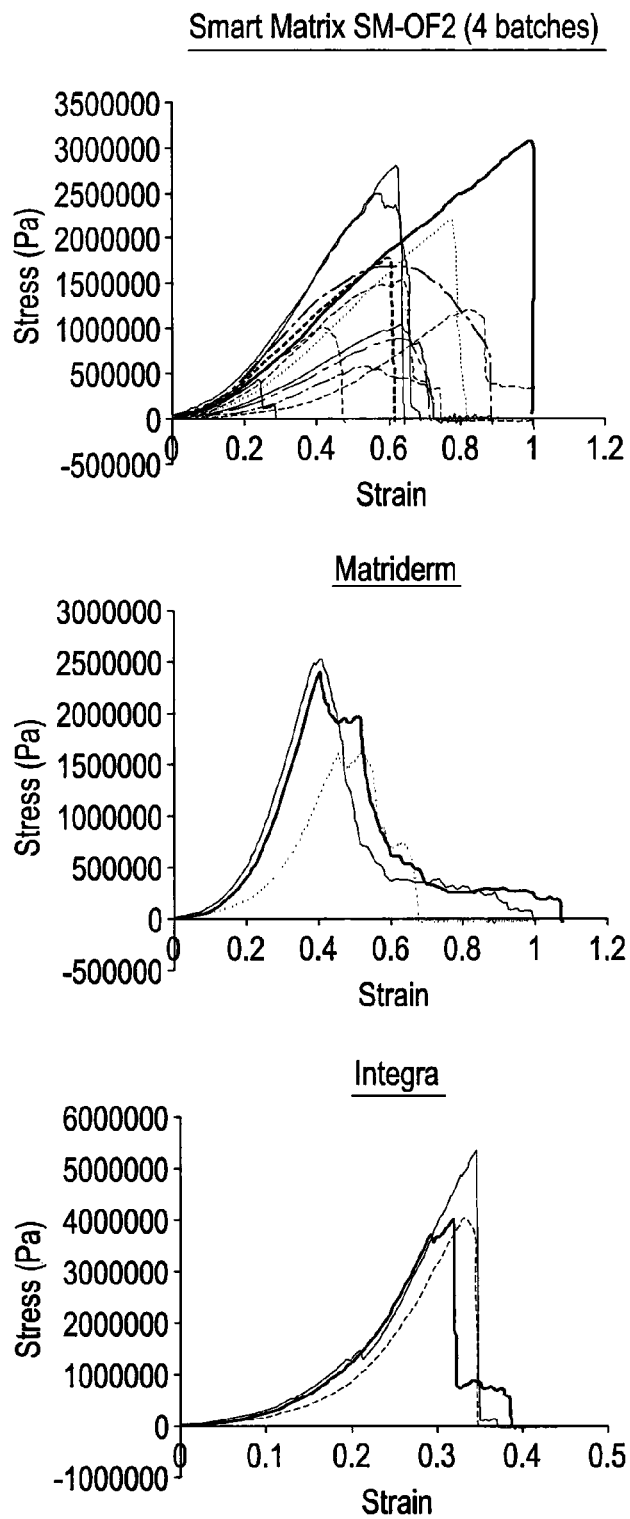

Further tensiometric measurements using a Stable Microsystems texture analyser had less noise, and fell within the sensitivity range. For rectangular samples at 1 mm/min rate, the apparent Young's modulus of Smart Matrix (SM-OF2) was 2.75±1.01 MPa (Mean±SD, n=12). The ultimate tensile strength of the series of scaffolds (1.61±0.54) were similar to the Matriderm (2.16±0.50) and less than Integra (4.46±0.76) (MPa, MN±SD, SM n=12, MD n=3, INT n=3). Interestingly, high porosity forms of Smart Matrix showed greater ultimate elongation values. FIG. 23b shows Stress-strain curves for 4 batches of Smart Matrix (SM-OF #2) scaffolds with triplicate samples from each scaffold compared to Matriderm and Integra.

Initial characterization of the viscoelastic properties of Smart Matrix scaffolds and Matriderm corroborate the tensiometry, and show that the elastic modulus is the dominant determinant.

Complex Modulus values (Pa, Mn±SEM, n=3), at the frequency of 1 Hz were: 3004 pa±327, Smart Matrix (SM-OF #1) (with optimal porosity), and 5766 pa±334, Matriderm.

Conclusion

This work establishes important mechanical properties of Smart Matrix type scaffolds, showing that it is softer than Matriderm. This may contribute to the beneficial wound healing outcome established for Smart Matrix.

Reagent Mix—Stability Results

Fibrinogen Solubility
   NaCl>20 mM for 'salting-in'
   NaCl>133 mM with 0.5% pluronic (RT)
   NaCl>150 mM with 1:1 alginate
   NaCl>200 mM with 0.5% pluronic+1:1 alginate
   Temp>20° C.
   Sub of $Na^+$ with $K^+$—precipitate formed
   Substitution of $Cl^-$ with $SO_4^{2-}$—precipitate formed
   Substitution of $Cl^-$ with Tris at pH7.4—precipitate formed
   Substitution of HEPES (pKa 7.55) with Tris (pKa 8.06)—no precipitate
   1:1 alginate+glycerol, 20%–<2% pluronic; at 5%–<1% pluronic
   1:1 alginate+sucrose, 30%–<2% pluronic; at 15%–<1% pluronic Coagulation Results 1. Fibrinogen
   accelerated by: $Ca^{2+}$ (max at 20 mM); Thrombin (too fast>10×); Pluronic (<0.5%); Alginate (1:1)
   Inhibited by NaCl (optimal NaCl approx 20-50 mM).
     150 to 75 mM NaCl decreases coagulation time from 10 to 3 mM.
   Partial substitution of Cl– by HEPES at 150 mM accelerates rate
   If precipitate is present prior to coagulation (A425>0.1), resulting gel is sub-optimal.

2. Reagent Mix coagulation:
   Fibrinogen+alginate 1:1+pluronic 0.5% gives satisfactory rate (<5 min) at 200 mM NaCl.

3. Ion/buffer substitutions: Substitute HEPES with Tris—no coagulation

4. Glycerol and sucrose protect against surfactant induced precipitate, but inhibit coagulation rate. Glycerol at 5% is acceptable, with 1:1 alginate and 1% pluronic. Sucrose at 15% may not be acceptable.

5. Alternative non-ionic surfactants to pluronic (Triton X100 & Tween 20) cause precipitate at similar concentrations—no obvious benefit.

Formulation—Solution Stability

Fibrinogen Stabilising:
   NaCl>50 mM
   Glycerol>5%
   Sucrose, glucose, sorbitol 2-20%, >10%
   Trehalose: before thrombin addition 10-11%; after thrombin/alginate/surfactant addition 4-7.5% (about 6.6%)
   Octyl-beta D-glucopyranoside>0.5%

Fibrinogen Precipitating:
   NaCl<50 mM
   Alginate>0.5%
   Pluronic F68>0.2%

Formulation—Coagulation

Coagulation Accelerating
   NaCl<50 mM
   Alginate>0.5%
   Pluronic F68>0.2%
   MES>HEPES Coagulation Inhibiting:
   NaCl>75 mM
   Glycerol>5%
   Sucrose, glucose, sorbitol>5%

Trehalose 4-7.5%%
Octyl-beta D-glucopyranoside>0.5%
Tris>HEPES
Formulation—Foam Stability
Foam Stabilising:
　NaCl<50 mM
　Glycerol>5%
　Trehalose 4-7.5%
　Octyl-beta D-glucopyranoside
Foam Destabilising:
　NaCl>50 mM
　Alginate>0.5%
　Pluronic F68<2%
Foam Forming Combinations with Fibrinogen:
　Alginate>0.5%+surfactant>2%
　Pluronic F68>0.2%
　MES>HEPES
Coagulation Inhibiting:
　NaCl>75 mM
　Glycerol>5%
　Sucrose, glucose, sorbitol
　Trehalose 4-7.5%
　Octyl-beta D-glucopyranoside
　Tris>HEPES
Stability/Coagulation Conclusions
　Reagent mix stability is critical.
　Some negative parameters have been identified for stability. Increased viscosity via H-bond agents (glycerol, sucrose) increases stability against surfactant (good) but inhibits coagulation (bad).
　Stability control can be obtained via NaCl, buffer salt, temperature, (polyols such as glycerol, sucrose, trehalose) surfactant and alginate components.
　Use sugar surfactant, or several surfactants, such as octyl gluco-pyranoside.
　Optimised formulation uses other factors, such as stabilising agent (trehalose).
Conclusions from the Experimental Results
1. It has been possible to create a consistent formulation of fibrin-alginate material using a strategy which combines trehalose as a stabilising agent, with sugar-based surfactants added to pluronic surfactant.
2. The first example of a sugar surfactant in combination with a Pluronic (F127 or F68) was OGP (SMOF-1). This yields a biomaterial structure with large open pores, which is compatible with promoting healing, but with some histological problems (material collapse and ensuing inflammatory reaction, cell breakthrough and envelopment in some cases). Interpretation of this in vivo behaviour has provided criteria against which scaffold structure can be improved.
3. Variation in the resulting structure is seen using different types of sugar-acyl surfactant. This variation allows selection of an optimal surfactant. The assessment of surfactants showed:
(i) SPAN series were mainly ineffective due to low aqueous solubility. It was only possible to obtain solutions by dissolving SPANs in Pluronic F68/OGP mix, with varying degrees of heat. The scaffold structures obtained did not improve on SMOF #1, although increased foam formation was found. Results were also inconsistent, possible due to the solubility difficulty.
(ii) Varying chain length of the glucopyranoside series (C6, C8, C10, C12) gave variations, which allowed some selectivity.
C6 (HGP) scaffolds had low foam formation, with poor histological structure. C10, DGP gave good foam and slightly better structure than SMOF #1. The solubility of DdGP was borderline and required warming to maintain the solution phase. It gave less foam but an improved lamellar structure, when incorporated into a mixture with DMP, ODM and F68.

(iii) Thioglucopyranoside, used as a more stable biochemical surfactant than OGP, showed a structure similar to SMOF #1, but did not seem to be advantageous.

(iv) The maltoside series ODM, DMP gave a greater foam stability than the glucosyl analogues. DDMP did not appear to be as effective as DMP. Another practical observation is the stability of the foam structure at the stage of cross-linking addition. ODM and DMP were found to reduce the degree of collapse of foam at this stage. The acyl sucrose series, [nDSuc and DdSuc . . . ], was similarly useful. DMP and DdSuc as single surfactants, substituted into the SMOF #2 formulation, give similar resultant structures.

(v) The combination of DMP with DdGP and ODM gives the best foam bulk, and stability of structure on cross-linking. This enabled formulation of SMOF #2.

The invention claimed is:

1. A process for preparing an extracellular matrix composition which has a reduced occurrence of dense plates or micro-aggregates of precipitated protein, the process comprising: (a) mixing an aqueous solution of fibrinogen with a coagulating agent, a bulking agent, and a foaming agent comprising more than one sugar surfactants; (b) causing the mixture to foam and coagulate; (c) incubating the mixture obtained in step (b) with a cross-linking agent; and (d) washing the cross-linked composition obtained in step (c) to remove the cross-linking agent, wherein said reduced occurrence of dense plates or micro-aggregates of precipitated protein is in comparison to a matrix composition produced according to the above process except that the foaming agent in step (a) is not a sugar surfactant.

2. The process according to claim 1 wherein the fibrinogen is present at a purity level of greater than one of 75%, 80%, 85%, 90%, 95%, 97% or 99%.

3. The process according to claim 1 wherein the aqueous solution of fibrinogen is essentially free of other protein.

4. The process according to claim 1 wherein fibrinogen is present as truncated forms of fibrinogen.

5. The process according to claim 4 wherein the truncated form of fibrinogen is fibrin E.

6. The process according to claim 1 wherein fibrinogen is present as an aqueous solution buffered to a pH of between 4 and 10.

7. The process according to claim 1 wherein the coagulating agent comprises an enzymatic or non-enzymatic coagulating agent.

8. The process according to claim 7 wherein the coagulating agent is thrombin.

9. The process according to claim 1 wherein the foaming agent consists of or comprises more than one surfactant agent(s) from the class of sugar-acyl surfactants.

10. The process according to claim 9 wherein the foaming agent is from the class of sugar-acyl surfactants having an acyl chain length between $C_8$ and $C_{12}$.

11. The process according to claim 9, wherein the sugar-acyl surfactants are selected from the class of pyranoside, maltoside, and acyl-sucrose surfactants.

12. The process according to claim 11 wherein the sugar-acyl surfactants are selected from the group consisting of octyl β-D-glucopyranoside (OGP), n-octyl β-D-maltoside (ODM), decyl-β-D-glucopyranoside (DGP) and dodecyl-β-D-glucopyranoside (DdGP), octyl β-D-1-thioglucopyranoside (TGP), hexyl β-D-glucopyranoside (HGP), decyl β-D-maltopyranoside (DMP), decyl sucrose (nDSuc), and dodecylsucrose (nDdS).

13. The process according to claim 12 wherein the sugar-acyl surfactants comprise or consist of DMP, DdGP and ODM.

14. The process according to claim 1 wherein the mixture of step (a) further comprises a non-ionic detergent, a thermo-sensitive gelling surfactant, a poloxamer or a poloxamine, a diphosphatydyl-glycerol type phospholipid, or a mixture of an immiscible phase with the aqueous fibrinogen solution phase.

15. The process according to claim 1 wherein the mixture of step (a) further comprises a non-ionic surfactant.

16. The process according to claim 1 wherein the bulking agent is an alginate.

17. The process according to claim 1 wherein the bulking agent is selected from hydroxyethylstarch, ethyl cellulose, xanthan gum and agarose.

18. The process according to claim 1 wherein the bulking agent is or includes a glycosaminoglycan (GAG).

19. The process according to claim 1 wherein the cross-linking agent is selected from: carbodiimide coupling agents N-hydroxysuccinimide (NHS), azide coupling agents, diisocyanate cross-linking agents, epoxide cross-linking agents, and aldehyde cross-linking agents.

20. The process according to claim 1 wherein the cross-linking agent comprises an aldehyde cross-linking agent.

21. The process according to claim 20 wherein the aldehyde cros s-linking agent is glutaraldehyde.

22. The process according to claim 20 which additionally comprises addition of a reducing agent or a toxicity reducing agent.

23. The process according to claim 1 wherein the foaming step (b) is achieved by mixing with aeration.

24. The process according to claim 1 for preparing an extracellular matrix composition having a predetermined shape, wherein either (i) the mixture of step (a) is cast in a mould of a predetermined shape, frozen and optionally lyophilised prior to the incubation step (c), or; (ii) the product of step (d) is produced in a mould of a predetermined shape, and the product is then frozen and optionally lyophilised.

25. The process according to claim 1 which additionally comprises addition of a divalent or multivalent metal ion.

26. An extracellular matrix composition comprising cross-linked fibrin, obtained by the process of claim 1.

27. The process according to claim 1, wherein the extracellular matrix composition produced by the process is essentially free of dense micro-aggregates, or plates, of precipitated protein.

28. The process according to claim 1, wherein said extracellular matrix composition produced by the process has a reduced occurrence of dense plates or micro-aggregates of precipitated protein compared to a matrix composition produced according to the process except that the foaming agent in step (a) comprises at least one surfactant that is a non-ionic block co-polymer of ethylene oxide and propylene oxide but which does not comprise more sugar surfactants.

29. The process according to claim 1, wherein said foaming agent comprises more than one sugar surfactants and a non-ionic block copolymer of ethylene oxide and propylene oxide.

30. The process according to claim 1, wherein the mixture of step (a) further comprises a sugar as a protein stabilizer, wherein the sugar is a small polyol or carbohydrate.

31. The process according to claim 30, wherein the sugar is trehalose.

32. The process according to claim 31, wherein said trehalose is an amount of 3-13% mass:vol.

33. The process according to claim 31, wherein said trehalose is in an amount of 7-7.5% mass:volume.

34. The process according to 30, wherein said sugar is glycerol, sorbitol, sucrose, or trehalose.

35. The process according to claim 1, wherein said foaming agent comprises one or more sugar surfactants selected from the group consisting of OGP, DMP, DdGP, ODM and nDSuc.

36. The process according to claim 1, wherein said foaming agent comprises a non-ionic poloxamer surfactant.

37. The process according to claim 1, wherein each surfactant of the foaming agent is present in a concentration of 0.1 to 5% wt./vol.

38. The process according to claim 1, wherein the foaming agent comprises DMP, DdGP, ODM and a non-ionic poloxamer surfactant.

* * * * *